(12) United States Patent
Gallatin et al.

(10) Patent No.: US 9,492,449 B2
(45) Date of Patent: Nov. 15, 2016

(54) THERAPIES FOR HEMATOLOGIC MALIGNANCIES

(75) Inventors: W. Michael Gallatin, Mercer Island, WA (US); Roger G. Ulrich, Foster City, CA (US); Neill A. Giese, San Francisco, CA (US); Brian Lannutti, Seattle, WA (US); Langdon Miller, Lebanon, NJ (US); Thomas M. Jahn, Seattle, WA (US)

(73) Assignee: Gilead Calistoga LLC, Foster City, CA (US)

( * ) Notice: Subject to any disclaimer, the term of this patent is extended or adjusted under 35 U.S.C. 154(b) by 118 days.

(21) Appl. No.: 13/417,185

(22) Filed: Mar. 9, 2012

(65) Prior Publication Data

US 2013/0071323 A1    Mar. 21, 2013

Related U.S. Application Data

(63) Continuation-in-part of application No. 12/618,612, filed on Nov. 13, 2009, now abandoned.

(60) Provisional application No. 61/245,196, filed on Sep. 23, 2009, provisional application No. 61/231,278, filed on Aug. 4, 2009, provisional application No. 61/180,768, filed on May 22, 2009, provisional application No. 61/155,057, filed on Feb. 24, 2009, provisional application No. 61/142,845, filed on Jan. 6, 2009, provisional application No. 61/114,434, filed on Nov. 13, 2008.

(51) Int. Cl.
| | | |
|---|---|---|
| *A61K 31/517* | (2006.01) | |
| *A61K 31/395* | (2006.01) | |
| *A61K 31/519* | (2006.01) | |
| *A61K 39/00* | (2006.01) | |

(52) U.S. Cl.
CPC ........... *A61K 31/517* (2013.01); *A61K 31/519* (2013.01); *A61K 2039/505* (2013.01)

(58) Field of Classification Search
CPC .............. C07D 473/34; C07D 403/14; A61K 31/517; A61K 31/513; A61K 31/52; A61K 41/05; A61K 31/519; A61K 31/395; A61K 2039/505; A61K 2300/00
USPC ...... 514/251, 266.2, 263.4, 19.3, 19.4, 19.6; 544/256
See application file for complete search history.

(56) References Cited

U.S. PATENT DOCUMENTS

| | | |
|---|---|---|
| 3,322,756 A | 5/1967 | Ruschig et al. |
| 3,691,016 A | 9/1972 | Patel |
| 3,897,432 A | 7/1975 | Shen et al. |
| 3,969,287 A | 7/1976 | Jaworek et al. |
| 3,984,555 A | 10/1976 | Amschler et al. |
| 4,179,337 A | 12/1979 | Davis et al. |
| 4,183,931 A | 1/1980 | Wolfe et al. |
| 4,195,128 A | 3/1980 | Hildebrand et al. |
| 4,225,489 A | 9/1980 | Rolf et al. |
| 4,229,537 A | 10/1980 | Hodgins et al. |
| 4,247,642 A | 1/1981 | Hirohara et al. |
| 4,289,872 A | 9/1981 | Denkewalter et al. |
| 4,301,144 A | 11/1981 | Iwashita et al. |
| 4,330,440 A | 5/1982 | Ayers et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |

(Continued)

FOREIGN PATENT DOCUMENTS

| | | |
|---|---|---|
| CN | 1824299 A | 8/2006 |
| EP | 0 525 960 A1 | 2/1993 |

(Continued)

OTHER PUBLICATIONS

Abbott, B.L. The Oncologist, 2006, vol. 11, pp. 21-30.*

(Continued)

*Primary Examiner* — Samira Jean-Louis

(74) *Attorney, Agent, or Firm* — Morrison & Foerster LLP

(57) ABSTRACT

The invention provides methods that relate to a novel therapeutic strategy for the treatment of hematological malignancies and inflammatory diseases. In particular, the method comprises administering a compound of formula A, (A)

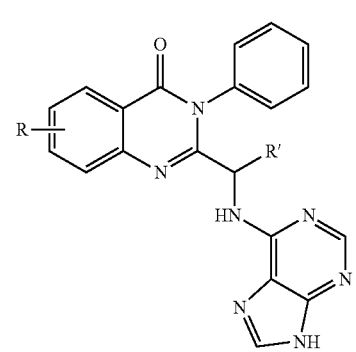

wherein R is H, halo, or C1-C6 alkyl;

R' is C1-C6 alkyl; or a pharmaceutically acceptable salt thereof; and optionally a pharmaceutically acceptable excipient;

and administering at least one additional therapeutic agent.

16 Claims, 44 Drawing Sheets

(56) References Cited

U.S. PATENT DOCUMENTS

| | | |
|---|---|---|
| 4,925,673 A | 5/1990 | Steiner et al. |
| 5,013,556 A | 5/1991 | Woodle et al. |
| 5,225,347 A | 7/1993 | Goldberg et al. |
| 5,229,490 A | 7/1993 | Tam |
| 5,378,725 A | 1/1995 | Bonjouklian et al. |
| 5,480,906 A | 1/1996 | Creemer et al. |
| RE35,862 E | 7/1998 | Steiner et al. |
| 5,858,753 A | 1/1999 | Chantry et al. |
| 5,882,910 A | 3/1999 | Chantry et al. |
| 5,948,664 A | 9/1999 | Williams et al. |
| 5,985,589 A | 11/1999 | Chantry et al. |
| 6,046,049 A | 4/2000 | Monia et al. |
| 6,048,970 A | 4/2000 | Lal et al. |
| 6,277,981 B1 | 8/2001 | Tu et al. |
| 6,291,220 B1 | 9/2001 | Williams et al. |
| 6,369,038 B1 | 4/2002 | Blumenfeld et al. |
| 6,410,224 B1 | 6/2002 | Stinchcomb et al. |
| 6,426,337 B1 | 7/2002 | Cox et al. |
| 6,482,623 B1 | 11/2002 | Vanhaesebroeck et al. |
| 6,518,277 B1 | 2/2003 | Sadhu et al. |
| 6,667,300 B2 | 12/2003 | Sadhu et al. |
| 6,696,250 B1 | 2/2004 | Cech et al. |
| 6,800,620 B2 | 10/2004 | Sadhu et al. |
| 6,949,535 B2 | 9/2005 | Sadhu et al. |
| 7,932,260 B2 | 4/2011 | Fowler et al. |
| 8,138,195 B2 | 3/2012 | Sadhu et al. |
| 8,207,153 B2 | 6/2012 | Fowler et al. |
| 8,492,389 B2 | 7/2013 | Sadhu et al. |
| RE44,599 E | 11/2013 | Fowler et al. |
| 8,586,597 B2 | 11/2013 | Fowler et al. |
| RE44,638 E | 12/2013 | Fowler et al. |
| 8,623,881 B2 | 1/2014 | Sadhu et al. |
| 8,637,533 B2 | 1/2014 | Sadhu et al. |
| 8,653,077 B2 | 2/2014 | Sadhu et al. |
| 8,779,131 B2 | 7/2014 | Kesicki et al. |
| 8,980,901 B2 | 3/2015 | Fowler et al. |
| 8,993,583 B2 | 3/2015 | Fowler et al. |
| 2004/0023390 A1 | 2/2004 | Davidson et al. |
| 2004/0092561 A1 | 5/2004 | Ruckle et al. |
| 2004/0121996 A1 | 6/2004 | Barvian et al. |
| 2004/0138199 A1 | 7/2004 | Goglietti et al. |
| 2004/0242631 A1 | 12/2004 | Garlich et al. |
| 2004/0248953 A1 | 12/2004 | Gogliotti et al. |
| 2004/0248954 A1 | 12/2004 | Gogliotti et al. |
| 2004/0259926 A1 | 12/2004 | Bruendle et al. |
| 2005/0004195 A1 | 1/2005 | Para et al. |
| 2005/0020630 A1 | 1/2005 | Connolly et al. |
| 2005/0020631 A1 | 1/2005 | Gogliotti et al. |
| 2005/0043239 A1 | 2/2005 | Douangpanya et al. |
| 2005/0054614 A1 | 3/2005 | Diacovo et al. |
| 2005/0239809 A1 | 10/2005 | Watts et al. |
| 2005/0261317 A1 | 11/2005 | Sadhu et al. |
| 2006/0079538 A1 | 4/2006 | Hallahan et al. |
| 2006/0084691 A1 | 4/2006 | Piperdi |
| 2006/0106038 A1 | 5/2006 | Bouscary et al. |
| 2008/0275067 A1 | 11/2008 | Fowler et al. |
| 2008/0287469 A1 | 11/2008 | Diacovo et al. |
| 2010/0029693 A1 | 2/2010 | Douangpanya et al. |
| 2010/0152211 A1 | 6/2010 | Sadhu et al. |
| 2010/0168139 A1 | 7/2010 | Sadhu et al. |
| 2010/0202963 A1 | 8/2010 | Gallatin et al. |
| 2010/0249155 A1 | 9/2010 | Evarts et al. |
| 2010/0256167 A1 | 10/2010 | Fowler et al. |
| 2010/0256168 A1 | 10/2010 | Fowler et al. |
| 2011/0044942 A1 | 2/2011 | Puri et al. |
| 2011/0230465 A1 | 9/2011 | Stammers et al. |
| 2012/0015964 A1 | 1/2012 | Fowler et al. |
| 2012/0040980 A1 | 2/2012 | Huggins et al. |
| 2012/0135994 A1 | 5/2012 | Sadhu et al. |
| 2012/0172591 A1 | 7/2012 | Sadhu et al. |
| 2013/0064812 A1 | 3/2013 | Gallatin et al. |
| 2013/0071323 A1 | 3/2013 | Gallatin et al. |
| 2013/0116266 A1 | 5/2013 | Fowler et al. |
| 2013/0231356 A1 | 9/2013 | Kesicki et al. |
| 2014/0066386 A1 | 3/2014 | Gallatin et al. |
| 2014/0121223 A1 | 5/2014 | Fowler et al. |
| 2014/0121224 A1 | 5/2014 | Fowler et al. |
| 2014/0154772 A1 | 6/2014 | Sadhu et al. |
| 2014/0323439 A1 | 10/2014 | Gallatin et al. |
| 2014/0378479 A1 | 12/2014 | Kesicki et al. |

FOREIGN PATENT DOCUMENTS

| | | |
|---|---|---|
| EP | 0 525 960 B1 | 2/1993 |
| EP | 0 675 124 A2 | 10/1995 |
| EP | 0 675 124 A3 | 10/1995 |
| EP | 0 716 857 A1 | 6/1996 |
| EP | 0 716 857 B1 | 6/1996 |
| EP | 0 884 310 A1 | 12/1998 |
| EP | 0 884 310 B1 | 12/1998 |
| EP | 0 900 568 A2 | 3/1999 |
| EP | 0 900 568 A3 | 3/1999 |
| EP | 1 949 912 A2 | 7/2008 |
| GB | 1356763 A | 6/1974 |
| GB | 2 017 097 A | 10/1979 |
| JP | S53-44581 A | 4/1978 |
| JP | 55 118917 A2 | 9/1980 |
| JP | 55 118918 A2 | 9/1980 |
| JP | 56 002322 A2 | 1/1981 |
| WO | WO-93/21259 A1 | 10/1993 |
| WO | WO-94/17090 A1 | 8/1994 |
| WO | WO-95/24379 A1 | 9/1995 |
| WO | WO-96/04923 A1 | 2/1996 |
| WO | WO-96/25488 A1 | 8/1996 |
| WO | WO-96/32478 A1 | 10/1996 |
| WO | WO-97/34631 A1 | 9/1997 |
| WO | WO-97/41097 A2 | 11/1997 |
| WO | WO-97/43276 A1 | 11/1997 |
| WO | WO-97/46688 A1 | 12/1997 |
| WO | WO-98/33802 A1 | 8/1998 |
| WO | WO-98/38173 A1 | 9/1998 |
| WO | WO-99/08501 A2 | 2/1999 |
| WO | WO-99/08501 A3 | 2/1999 |
| WO | WO-99/34804 A1 | 7/1999 |
| WO | WO-01/00881 A1 | 1/2001 |
| WO | WO-01/30768 A1 | 5/2001 |
| WO | WO-01/30768 C2 | 5/2001 |
| WO | WO-01/53266 A1 | 7/2001 |
| WO | WO-01/57034 A1 | 8/2001 |
| WO | WO-01/81346 A2 | 11/2001 |
| WO | WO-01/81346 A3 | 11/2001 |
| WO | WO-03/035075 A1 | 5/2003 |
| WO | WO-03/106622 A2 | 12/2003 |
| WO | WO-03/106622 A3 | 12/2003 |
| WO | WO-2004/007491 A1 | 1/2004 |
| WO | WO-2004/012768 A1 | 2/2004 |
| WO | WO-2004/026285 A2 | 4/2004 |
| WO | WO-2004/026285 A3 | 4/2004 |
| WO | WO-2004/029055 A1 | 4/2004 |
| WO | WO-2004/052373 A1 | 6/2004 |
| WO | WO-2004/056820 A1 | 7/2004 |
| WO | WO-2004/089925 A1 | 10/2004 |
| WO | WO-2004/108708 A1 | 12/2004 |
| WO | WO-2004/108709 A1 | 12/2004 |
| WO | WO-2004/108713 A1 | 12/2004 |
| WO | WO-2004/108713 C1 | 12/2004 |
| WO | WO-2004/108715 A1 | 12/2004 |
| WO | WO-2004/108715 C1 | 12/2004 |
| WO | WO-2005/016348 A1 | 2/2005 |
| WO | WO-2005/016349 A1 | 2/2005 |
| WO | WO-2005/067901 A2 | 7/2005 |
| WO | WO-2005/067901 A3 | 7/2005 |
| WO | WO-2005/112935 A1 | 12/2005 |
| WO | WO-2005/113556 A1 | 12/2005 |
| WO | WO-2005/117889 A1 | 12/2005 |
| WO | WO-2005/120511 A1 | 12/2005 |
| WO | WO-2006/089106 A1 | 8/2006 |
| WO | WO-2007/067976 A2 | 6/2007 |
| WO | WO-2007/067976 A3 | 6/2007 |
| WO | WO-2008/091620 A2 | 7/2008 |
| WO | WO-2008/091620 A3 | 7/2008 |
| WO | WO-2009/052467 A1 | 4/2009 |
| WO | WO-2009/058361 A1 | 5/2009 |
| WO | WO-2010/057048 A1 | 5/2010 |

(56) References Cited

FOREIGN PATENT DOCUMENTS

| WO | WO-2010/065923 A2 | 6/2010 |
|---|---|---|
| WO | WO-2010/065923 A3 | 6/2010 |
| WO | WO-2010/123931 A1 | 10/2010 |
| WO | WO-2011/1535514-A2 STET | 12/2011 |
| WO | WO-2011/1535514-A9 STET | 12/2011 |
| WO | WO-2011/1535514-C1 STET | 12/2011 |
| WO | WO-2012/125510 A1 | 9/2012 |

OTHER PUBLICATIONS

"Acute Congestive Heart Failure", Thomas N. Levin, Postgraduate Medicine, vol. 101, No. 1, 1997.
Sutton, A. (Jun. 9, 2006). "Baylor, St. Luke's study uses gene therapy as pancreatic cancer", located at <http://www.bcm.edu/news/item.cfm?newsID=640>, last visited on Sep. 2, 2006, 2 pages.
Anonymous (2006). "Cardiovascular Disease: Treatment for Stroke", Stanford Hospital & Clinics, located at <http://www.stanfordhospital.com/healthLib/atoz/cardiac/stktreat.html>, last visited on Sep. 19, 2006, 2 pages.
Marchione et al. (2006). "Drugs hold promise in kidney cancer fight", located at <http://www.ledger-enquirer.com/mid/ledgerenquirer/living/health/14744763.htm>, last visited on Sep. 2, 2006, 3 pages.
Anonymous (2006). "Heart Disease", WebMD, located at <http://www.webmd.com/content/pages/9/1675_57842.htm> as retrieved on Sep. 14, 2006, 1 page.
Anonymous, (2010). "Multiple Sclerosis", located at <http://health.nytimes.com/health/guides/disease/multiple-sclerosis/overview.html>, last visited Aug. 1, 2010, 4 pages.
Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous (2010). "Spinal Cord Injury", located at <http://www.medicinenet.com/spinal_cord_iniury/page.htm>, last visited on Aug. 1, 2010, 3 pages.
Anonymous (2010) "Systemic Lupus Erythematosus", located at <http://www.nlm.nih.gov/medlineplus/ency/article/000435.htm>, last visited Aug. 1, 2010, 4 pages.
Anonymous. "A Phase I Study to Investigate the Safety and Clinical Activity of CAL-101 in Combination with Bendamustine and Rituximab in Patients with Relapsed or Refractory Indolent B-Cell Non-Hodgkin's Lymphoma or Chronic Lymphocytic Leukemia," <http://clinicaltrials.gov/ct2/show/NCT01088048?TERM+cal-101 &rank+1>, last visited Jul. 24, 2012, 4 pages.
Anonymous. "A Phase 2 Single Arm Study to Investigate the Safety and Clinical Activity of CAL-101 in Combination with Rituximab in Elderly Patients with Previously Untreated Chronic Lymphocytic Leukemia or Small Lymphocytic Lymphoma," located at <http://clinicaltrials.gov/archive/NCT01203930/2010_09_16>, last visited Jul. 24, 2012, 8 pages.
Anonymous. (Jan. 2011). RITUXAN® Prescribing Information, 33 pages.
Abramson and Shipp, Blood (2005) 106(4):1164-1174.
"Chemia Lekow", ed. E. Pawelczyk, PZWL, Warszawa 1986, see, part 1.2.2.
"Preparatyka Organiczna", ed. A.I. Vogel, WNT, Warszawa 1984, p. e.g. 83.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, located at: <http://www.imt.uni-marburg.de/~adamkiew/mechanism.html>, 2 pages.
Advisory Action from U.S. Appl. No. 11/596,092, mailed on Jul. 27, 2010.
Ager et al., J. Med. Chem. (1977) 20:379-386.

Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, located at <http://www.weizmann.ac.il/Biolooy/open_day_2002/book/ronen_alon.pdf>, 2 pages.
Amendment from U.S. Appl. No. 09/841,341, filed Aug. 21, 2002.
Amendment from U.S. Appl. No. 10/027,591, filed Jun. 3, 2003.
Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.
Amendment in Response to Non-Final Office Action from U.S. Appl. No. 11/110,204, filed Jun. 4, 2010.
Amendment in Response to Non-Final Office Action from U.S. Appl. No. 11/596,092, filed Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.
Amin et al., Circ Res (2003) 93(4):321-329.
Amine, M.S. et al. (Nov. 1998). "Uses of Quinazolin-2-[(β-Propionoyl) Isothiocyanate]-4-One as a Building Block in Synthesis of Some Heterocyclic Compounds of Expected Biological Activity," *Indian Journal of Chemistry* 37B(11):1153-1156.
Angel, Activities of Phosphoinositide Kinase-3 (PI3K) (1999) retrieved from the internet on May 22, 2003, URL: http://www.chem.csustan.edu/chem4400/SJBR/angel99.htm.
Angio World, "How Angiogenesis Complicates Psoriasis" (2001) retrieved from the internet on Apr. 13, 2004, located at <http://www.angioworld.com/psoriasis.htm>,1 page.
Annabi et al., J. Cell. Biochem. (2004) 91:1146-1158.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Bader, A.G. et al. (2005). "Oncogenic PI3K Deregulates Transcription and Translation," *Nature Reviews Cancer* 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," *Az. J. Pharm. Sci.* 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Berge et al., J. Pharm. Sci. (1977) 66:1.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.

(56) References Cited

OTHER PUBLICATIONS

Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," *Haematologica* 95(s2):466, Abstract No. 1130.
Brunn et al., EMBO J. (1996) 15:5256-5267.
Burgering et al., Nature (1995) 376:599-602.
Butcher et al., Science (1996) 272:60-66.
Byrd et al. Blood, Published online 2004, vol. 105, pp. 49-53.
Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 112-118.
Castillo, J.J. et al. (Jan. 2012). "CAL-101: A Phosphatidylinositol-3-Kinase p110-Delta Inhibitor for the Treatment of Lymphoid Malignancies," *Expert Opinion on Investigational Drugs* 21(1): 15-22.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry, D. et al. (1997). "p110δ, a Novel Phosphatidylinositol 3-Kinase Catalytic Subunit That Associates with p85 and Is Expressed Predominantly in Leukocytes," *J. Biol. Chem.* 272(31):19236-19241.
Chen et al., Blood (2000) 96:3181-3187.
Chern et al., Chem. Pharm. Bull. (1998) 46(6):928-933.
Chern et al., Chemical Abstracts (1998) 129(16):676.
Cheson et al., The New England Journal of Medicine (2008) 359(6):613-626.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," *Curr. Oncol. Rep.* 12:87-94.
Coligan et al., Current Protocols in Protein Science (2002) 3:15-20.
Collins, R.J. et al. (1989). "Spontaneous Programmed Death (Apoptosis) of B-Chronic Lymphocytic Leukaemia Cells Following Their Culture in vitro," *British Journal of Haematology.* 71(3):343-350.
Computer Search Cart Navigator, retrieved from the internet on Mar. 22, 2001, URL: http://www.chemnavigator.com/members/CartNavigator.asp#sample1, 8 pages.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dania et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351 :95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.

Devos, S. et al. (Nov. 2011). "A Phase 1 Study of the Selective Phosphatidylinositol 3-Kinase-Delta (PI3K) Inhibitor, CAL-101 (GS-1101), in Combination with Rituximab and/or Bendamustine in Patients with Previously Treated, Indolent Non-Hodgkin Lymphoma (iNHL)," *Blood* 118(21):1160.
Doggett et al., Biophys. J. (2002) 83:194-205.
Domanig, R. (1981). "Chinazolinone, 2. Mitt: Synthese Und Einige Reaktionen Von 2-Azidomethyl-3-Aryl-4-Chinazolinonen," *Monatshefte fuer Chemie* 112(10):1195-1202. (English translation of abstract only).
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," *Bollettino Chimico Farmaceutico* 137(7):286-289.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.
Etzioni, Pediatr. Res. (1996) 39:191-198.
European Search Report mailed Mar. 29, 2011, for EP Patent Application No. 10163434.3, filed on Apr. 24, 2001, 9 pages.
Extended European Search Report dated Jun. 6, 2013 for EP Patent Application No. 13150110.8 , filed May 12, 2005, 6 pages.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action mailed on Nov. 7, 2012, for U.S. Appl. No. 12/618,612, filed Nov. 13, 2009, 19 pages.
Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Oct. 24, 2011, for U.S. Appl. No. 12/732,128, filed Mar. 25, 2010, 8 pages.
Final Office Action mailed on Feb. 15, 2012, for U.S. Appl. No. 12/732,124, filed Mar. 25, 2010, 12 pages.
Final Office Action mailed on Jun. 7, 2012, for U.S. Appl. No. 11/129,006, filed May 12, 2005, 14 pages.
Final Office Action mailed on Jul. 9, 2013, for U.S. Appl. No. 13/399,828, filed Feb. 17, 2012, 6 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (PI3K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 114(22):380, Abstract 922.

(56) References Cited

OTHER PUBLICATIONS

Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Flinn, I.W. et al. (Nov. 2010). "A Phase 1 Study of CAL-101, An Isoform-Selective Inhibitor of Phosphatidylinositol 3-Kinase P110 Delta, In Combination with Rituximab and/or Bendamustine in Patients with Relapsed or Refractory B-Cell Malignancies," Blood 116(21):1168.
Folkman, Curr. Mol. Med. (2003) 3:643-651.
Folkman, Nat. Med. (1995) 1:27-31.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," *Clinical Advances in Hematology & Oncology* 8(7):475-476.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov.nuccore/23270986>, last visited on Apr. 16, 2010, 5 pages.
GenBank Accession No. NM_005026, last updated Apr. 11, 2010, located at <http://www.ncbi.nlm.nih.gov.nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.nlm.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gokbuget et al. (2006). Hematology 2006(1):133-141.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," *Communicative and Integrative Biology* 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herman, S.E.M. et al. (Mar. 4, 2011). "The Role of Phosphatidylinositol 3-Kinase-Delta in the Immunomodulatory Effects of Lenalidomide in Chronic Lymphocytic Leukemia," *Blood* 117(16):4323-4327.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Hoellenriegel, J. et al. (Nov. 2010). "Phosphoinositide 3'-Kinase (PI3K) Delta Inhibition with CAL-101 Blocks B-Cell Receptor (BCR) Signaling and the Prosurvival Actions of Nurselike Cells (NLC), In Chronic Lymphocytic Leukemia," *Blood* 116(21):27-28.
Hoellenriegel, J. et al. (Jul. 29, 2011). "The Phosphoinositide 3'-Kinase Delta Inhibitor, CAL-101, Inhibits B-Cell Receptor Signaling and Chemokine Networks in Chronic Lymphocytic Leukemia," *Blood* 118(13): 3603-3612.
Horgan et al., Am. J. Physiol. (1991) 261:H1578-H1584.
Hsieh, S.N. (2003). "Identification of PI3Kγ in Endothelial Cells and Its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.
Hu et al., Science (1995) 268:100-102.
Hunter, Cell (1995) 83:1-4.
Hussong et al., Blood (2000) 95:309-313.
Ikeda, H. et al. (Feb. 2009). "CAL-101: A Selective Inhibitor of PI3K p110δ for the Treatment of Multiple Myeloma," *Clinical Lymphoma and Myeloma* 9(Supp. 1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110δ is a Novel Therapeutic Target in Multiple Myeloma," *Blood* 116(9):1460-1468.

(56) References Cited

OTHER PUBLICATIONS

International Preliminary Report on Patentability for PCT/US2006/005621, issued on Aug. 21, 2007, 8 pages.
International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial No. PCT/US2004/026834, dated Nov. 29, 2004.
International Search Report for International (PCT) Patent Application Serial No. PCT/US2004/037860, dated May 6, 2005.
International Search Report mailed on Aug. 29, 2005, for PCT Application No. PCT/US2005/016778, filed on May 12, 2005, 4 pages.
International Search Report mailed on Sep. 15, 2006 for PCT Application No. PCT/US2006/005621, filed on Feb. 16, 2006, 4 pages.
International Search Report for PCT/US2009/064471, mailed on Feb. 12, 2010, 4 pages.
International Search Report mailed on Jun. 14, 2012 for PCT Application No. PCT/US2012/028654, filed on Mar. 9, 2012, 7 pages.
Interview Summary from U.S. Appl. No. 10/918,825, mailed on Jun. 14, 2006.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Jares, P. et al. (Oct. 2007). "Genetic and Molecular Pathogenesis of Mantle Cell Lymphoma: Perspectives for New Targeted Therapeutics," *Nat. Rev. Cancer* 7:750-762.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Kurcharsky, D. DocGuide.com, Jun. 2005, pp. 1-2.
Kurtova, A.V. et al. (2009). "Diverse Marrow Stromal Cells Protect CLL Cells From Spontaneous and Drug-Induced Apoptosis: Development of a Reliable and Reproducible System to Assess Stromal Cell Adhesion-Mediated Drug Resistance," *Blood.* 114(20):4441-4450.
Lannutti, B.J. et al. (Apr. 2009). "CAL-101, a Specific PI3K p110δ Inhibitor for the Treatment of Hematological Maglignancies," *Proceedings of the American Association for Cancer Research* 50:1400, Abstract No. #SY32-2.

Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, An Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(52):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Morton et al., Blood (2006) 107(1):265-276.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non-Final Office Action mailed on May 22, 2012, for U.S. Appl. No. 12/618,612, filed Nov. 13, 2009, 19 pages.
Non Final Office Action from U.S. Appl. No. 11/596,092, mailed on Dec. 24, 2009.
Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.
Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.

(56) References Cited

OTHER PUBLICATIONS

Non-Final Office Action from U.S. Appl. No. 11/110,204, mailed on Jun. 17, 2009.
Non-Final Office Action from U.S. Appl. No. 11/129,006, mailed on Dec. 15, 2009.
Non-Final Office Action mailed on Jan. 20, 2012 for U.S. Appl. No. 13/163,597, filed Jun. 17, 2011, 14 pages.
Non-Final Office Action mailed on Oct. 17, 2011 for U.S. Appl. No. 12/732,124, filed Mar. 25, 2010, 8 pages.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed on Jun. 28, 2011, for U.S. Appl. No. 12/732,124, filed Mar. 25, 2010, 11 pages.
Non-Final Office Action mailed on Aug. 2, 2012 for U.S. Appl. No. 12/575,277, filed Oct. 7, 2009, 8 pages.
Non-Final Office Action mailed on Aug. 7, 2012 for U.S. Appl. No. 12/575,367, filed Oct. 7, 2009, 9 pages.
Non-Final Office Action mailed on Feb. 13, 2013 for U.S. Appl. No. 13/247,962, filed Sep. 28, 2011, 21 pages.
Non-Final Office Action mailed on Mar. 1, 2013 for U.S. Appl. No. 13/399,828, filed Feb. 17, 2012, 6 pages.
Non-Final Office Action mailed on Mar. 25, 2013 for U.S. Appl. No. 13/728,807, filed Dec. 27, 2012, 13 pages.
Non-Final Office Action mailed on Jun. 26, 2013 for U.S. Appl. No. 13/765,610, filed Feb. 12, 2013, 9 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.
Notice of Allowance from U.S. Appl. No. 10/697,912, mailed on Dec. 30, 2004.
Notice of Allowance mailed on Nov. 8, 2010, for U.S. Appl. No. 11/110,204, filed Apr. 20, 2005, 6 pages.
Notice of Allowance mailed on Jun. 26, 2012 for U.S. Appl. No. 12/732,124, filed Mar. 25, 2010, 11 pages.
Notice of Allowance mailed on Nov. 13, 2012 for U.S. Appl. No. 12/732,124, filed Mar. 25, 2010, 11 pages.
Notice of Allowance mailed on Feb. 21, 2013 for U.S. Appl. No. 12/575,367, filed Oct. 7, 2009, 5 pages.
Notice of Allowance mailed on May 20, 2013, for U.S. Appl. No. 13/730,276, filed Dec. 28, 2012, 7 pages.
Notice of Allowance mailed on Jul. 8, 2013 for U.S. Appl. No. 13/728,807, filed Dec. 27, 2012, 9 pages.
Notice of Allowance mailed on Jul. 8, 2013 for U.S. Appl. No. 13/730,256, filed Dec. 28, 2012, 9 pages.
Notice of Allowance mailed on Aug. 28, 2013, for U.S. Appl. No. 12/575,277, filed Oct. 7, 2009, 6 pages.
Notice of Allowance mailed on Sep. 19, 2013, for U.S. Appl. No. 13/399,828, filed Feb. 17, 2012, 6 pages.
Notice of Allowance mailed on Oct. 3, 2013, for U.S. Appl. No. 13/247,962, filed Sep. 28, 2011, 9 pages.
Notice of Allowance mailed on Oct. 18, 2013, for U.S. Appl. No. 13/765,610, filed Feb. 12, 2013, 10 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 04 816 855.3, mailed on Oct. 21, 2008, 4 pages.
Office Action for European Patent Application No. 01 928 855.4, mailed on Feb. 26, 2009, 3 pages.
Office Action for European Patent Application No. 01 928 855.4, mailed on Nov. 15, 2007, 4 pages.
Office Action for European Patent Application No. 01 928 855.4, mailed on Mar. 29, 2006, 6 pages.
Office Action for European Patent Application No. 01 928 855.4, mailed on Jul. 13, 2004, 5 pages.
Office Action for European Patent Application No. 02 757 407.8, mailed on Oct. 6, 2009, 3 pages.
Office Action for European Patent Application No. 02 757 407.8, mailed on Jul. 1, 2009, 2 pages.
Office Action for European Patent Application No. 02 757 407.8, mailed on Oct. 21, 2008, 3 pages.
Office Action for European Patent Application No. 02 757 407.8, mailed on Jun. 6, 2007, 2 pages.
Office Action for European Patent Application No. 02 757 407.8, mailed on Jan. 24, 2006, 3 pages.
Office Action for European Patent Application No. 04 816 855.3, mailed on Feb. 2, 2011, 4 pages.
Office Action for European Patent Application No. 05 752 122.1, mailed on Dec. 28, 2010, 4 pages.
Office Action for European Patent Application No. 04 810 878.1, mailed on Sep. 10, 2010, 4 pages.
Office Action for European Patent Application No. 05 752 122.1, mailed on Mar. 25, 2013, 4 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.
Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: A Rational Approach in Drug Design," *Chem Rev.* 96(8):3147-3176.
Pierce et al., J. Biol. Chem. (1997) 272:21096-21103.
Pietersz et al., Immunol. Rev. (1992) 129:57.
Plows et al., J. Immunol. (1999) 162(2):1018-1023.
Podsypanina et al., Proc. Natl. Acad. Sci. (USA) (2001) 98:10320-10325.
Prescott, (ed.), Methods in Cell Biology, vol. XIV, Academic Press, New York (1976) p. 33.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers *Presented at the 12th International Congress of Immunology and 4th Annual Conference of FOCIS Medimond International Proceedings* in Montreal, Canada on Jul. 18, 23, 2004, pp. 303-307.
Quirici et al., Br. J. Haematol. (2001) 115:186-194.
Rameh et al., Cell (1995) 83:821-830.
Rameh et al., J. Biol. Chem. (1999) 274:8347-8350.
Rathman et al., J. Org. Chem. (1980) 45:2169-2176.
Reeder, C.B. et al. (Feb. 2011, e-published Oct. 26, 2010). "Novel Therapeutic Agents for B-Cell Lymphoma: Developing Rational Combinations," *Blood* 117(5): 1453-1462.
Remington's Pharmaceutical Sciences (1990) 18th Ed., Chapter 89, pp. 1435-1712 Table of Contents Only.

(56) References Cited

OTHER PUBLICATIONS

Ren et al., Curr. Drug Targets Inflamm. Allergy (2003) 2(3):242-256.
Request for Continued Examination and Amendment Under 37 C.F.R. § 1.116 from U.S. Appl. No. 10/918,803, filed May 7, 2009.
Response to Election of Species Requirement from U.S. Appl. No. 10/918,803, filed Jun. 27, 2007.
Response to Non-Final Office Action from U.S. Appl. No. 10/918,803, filed Dec. 18, 2009.
Response to Non-Final Office Action filed on Sep. 16, 2010, for U.S. Appl. No. 10/918,803, filed Aug. 13, 2004, 25 pages.
Response to Non-Final Office Action filed on Aug. 22, 2012 for U.S. Appl. No. 12/618,612, filed Nov. 13, 2009, 13 pages.
Response to Restriction Requirement filed on Mar. 9, 2012 for U.S. Appl. No. 12/618,612, filed Nov. 13, 2009, 11 pages.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed on Feb. 6, 2008.
Response to Restriction Requirement from U.S. Appl. No. 11/596,092, filed May 27, 2009.
Response to Rule 312 Communication mailed on Oct. 4, 2012, for U.S. Appl. No. 12/732,124, filed Mar. 25, 2010, 7 pages.
Restriction Requirement mailed on Feb. 9, 2012 for U.S. Appl. No. 12/618,612, filed Nov. 13, 2009, 7 pages.
Restriction Requirement from U.S. Appl. No. 10/918,803, mailed on Jun. 12, 2009.
Restriction Requirement from U.S. Appl. No. 10/918,803, mailed on Mar. 13, 2007.
Restriction Requirement from U.S. Appl. No. 10/918,803, mailed on Sep. 7, 2007.
Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Oct. 14, 2010, for U.S. Appl. No. 12/732,124, filed Mar. 25, 2010, 9 pages.
Restriction Requirement mailed on Dec. 1, 2011, for U.S. Appl. No. 13/163,597, filed Jun. 17, 2011, 7 pages.
Restriction Requirement mailed on Jun. 7, 2012, for U.S. Appl. No. 13/399,828, filed Feb. 17, 2012, 5 pages.
Restriction Requirement mailed on Jul. 17, 2012, for U.S. Appl. No. 13/247,962, filed Sep. 28, 2011, 27 pages.
Restriction Requirement mailed on Sep. 11, 2012, for U.S. Appl. No. 13/399,828, filed Feb. 17, 2012, 7 pages.
Restriction Requirement mailed on Feb. 27, 2013 for U.S. Appl. No. 13/417,180, filed Mar. 9, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rowlinson-Busza, G. et al. (1992). "Targeted Delivery of Biologic and Other Antineoplastic Agents," Curr. Opin. Oncol. 4:1142-1148.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.
Second Preliminary Amendment and Response to Notice to File Missing Parts of Nonprovisional Application from U.S. Appl. No. 12/575,277, filed Jan. 20, 2010.
Second Preliminary Amendment and Response to Notice to File Missing Parts of Nonprovisional Application from U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Sharman J. et al. (Nov. 2011). "A Phase I Study of the Selective Phosphatidylinositol 3-Kinase-Delta (PI3K Delta) Inhibitor, CAL-101 (GS-1101), in Combination with Rituximab and/or Bendamustine in Patients with Relapsed or Refractory Chronic Lymphocytic Leukemia (CLL)," Blood 118(21):779-780.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sujobert et al., Blood (2005) 106(3):1063-1066.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, mailed on Jun. 29, 2004.
Suzuki, E. et al. (2007). "Rituximab Inhibits the Constitutively Activated PI3K-Akt Pathway on B-NHL Cell Lines: Involvement in Chemosensitization to Drug-Induced Apoptosis," Oncogene (26):6184-6193.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000) 238:59-68.
Tan, J. et al. (Sep. 1, 2004). "A Specific Antagonist of the p110-Delta Catalytic Component of P13 Kinase, IC486068, Enhances Radiation-Induced Tumor Vascular Destruction," International Journal of Radiation: Oncology Biology Physics 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
Trail et al., Science (1993) 261:212.
U.S. Appl. No. 13/762,238, filed Feb. 7, 2013, by Gallatin et al.
U.S. Appl. No. 14/049,154, filed Oct. 8, 2013, by Fowler et al.
U.S. Appl. No. 14/049,163, filed Oct. 8, 2013, by Fowler et al.
Vacca et al., Blood (1999) 9:3064-3073.
Van Dijk et al., Blood (2000) 96:3406-3413.
Vanhaesebroeck et al., FASEB J. (1996) 10:A1395, Abst. No. 2280.

(56) References Cited

OTHER PUBLICATIONS

Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," *Advanced Drug Delivery* 48:3-26.
Vivanco et al., Nat. Rev. Cancer (2002) 2:489-501.
Vlahos et al., J. Immunol. (1995) 154:2413-2422.
Vogler, M. et al. (Apr. 30, 2009). Concurrent Up-Regulation of BCL-XL and BCL2A1 Induces Approximately 1000-Fold Resistance to ABT-737 in Chronic Lymphocytic Leukemia. *Blood* 113(18):4403-4413.
Volinia et al., EMBO J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110δ: Preclinical Summary," *Proceedings of the American Association for Cancer Research* 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Wierda, W.G. (2006). "Current and Investigational Therapies for Patients with CLL," *Hematology* pp. 285-294.
Williams, D.A. et al. (2002). *Foye's Principles of Medicinal Chemistry* Lippincott, Williams & Wilkins, Baltimore MD, Fifth Edition, pp. 50 and 59-61.
Williams, Methods Mol. Med. (2004) 98:207-216.
Williams et al., Chem. Biol. (2010) 17:123-134.
Wolff, ed., Burger's Medicinal Chemistry and Drug Discovery, 5th edition (1996) vol. 1, New York: John Wiley & Sons, pp. 975-977.
Written Opinion of the International Searching Authority for PCT/US2009/064471, Mailed on Feb. 12, 2010, 5 pages.
Written Opinion mailed on Jun. 14, 2012 for PCT Application No. PCT/US2012/028654, filed on Mar. 9, 2012, 11 pages.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Non-Final Office Action mailed on May 31, 2013, for U.S. Appl. No. 13/417,180, filed Mar. 9, 2012, 25 pages.
Chinese Office Action mailed on May 31, 2013, for Chinese Patent Application No. 200980154097.9, 11 pages. (with English translation).
Anonymous. (Mar. 2008). TREANDA® Prescribing Information, 6 pages.
Azenabor, A.A. et al. (2006). "Macrophage Antioxidant Enyzmes Regulate *Chlamydia pneumoniae* Chronicity: Evidence of the Effect of Redox Balance on Host-Pathogen Relationship," *Immunobiology* 211(5):325-339.
Chapman-Kirkland, E.S. et al. (1991). "Superoxide Anion Production From Human Neutrophils Measured with an Improved Kinetic and Endpoint Microassay," *J Immunol Meth* 142(1):95-104.
Extended European Search Report mailed on Dec. 10, 2013, for EP Patent Application No. 13150110.8, filed May 12, 2005, 10 pages.
Final Office Action mailed on Dec. 20, 2013, for U.S. Appl. No. 13/417,180, filed Mar. 9, 2012, 34 pages.
Green, S.J. et al. (1994). "Oxidative Metabolism of Murine Macrophages," Chapter 14, Unit 14.5 in *Current Protocols in Immunology*, vol. 3, John Wiley & Sons, Inc., pp. 14.5.1-14.5.11.

Ishida-Okawara, A. et al. (Dec. 12, 1996). "Modulation of Degranulation and Superoxide Generation in Human Neutrophils by Unsaturated Fatty Acids of Odd Carbon Numbers," *BioChimica et Biophysica Acta* 1314(3):239-246.
Jin, F. et al. (2014). "Exposure-Response of Idelalisib, a Novel Pi3k67 Inhibitor, in the Treatment of Hematologic Malignancies," presented at American Society of Clinical Pharmacology and Therapeutics Meeting, Atlanta, GA, Mar. 18-22, 1 page.
Non-Final Office Action mailed on Jun. 25, 2014, for U.S. Appl. No. 14/049,154, filed Oct. 8, 2013, 15 pages.
Non-Final Office Action mailed on Jun. 25, 2014, for U.S. Appl. No. 14/049,163, filed Oct. 8, 2013, 15 pages.
Notice of Allowance mailed on Feb. 21, 2014, for U.S. Appl. No. 13/765,610, filed Feb. 12, 2013, 9 pages.
Notice of Allowance mailed on Oct. 9, 2014, for U.S. Appl. No. 14/049,154, filed Oct. 8, 2013, 8 pages.
Notice of Allowance mailed on Oct. 10, 2014, for U.S. Appl. No. 14/049,163, filed Oct. 8, 2013, 8 pages.
Rada, B.K. et al. (Nov. 1, 2004, e-published Jul. 13, 2004). "Dual Role of Phagocytic NADPH Oxidase in Bacterial Killing," *Blood* 104(9):2947-2953.
Restriction Requirement mailed on Oct. 24, 2014 for U.S. Appl. No. 13/762,238, filed Feb. 7, 2013, 6 pages.
Van Eeden, S.F. et al. (Dec. 17, 1999). "The Use of Flow Cytometry to Measure Neutrophil Function," *Journal Immunol Meth* 232:23-43.
Zu, Y-L et al. (1998). "p38 Mitogen-Activated Protein Kinase Activation is Required for Human Neutrophil Function Triggered by TNF-α or FMLP Stimulation", *J Immunol* 160:1982-1989.
U.S. Appl. No. 14/599,287, filed Jan. 16, 2015, by Gallatin et al.
Australian Re-Examination Report mailed Sep. 3, 2015, for Australian Patent No. 2001255667, filed Apr. 24, 2001, 9 pages.
Fuentes Pinzon, Fernando, La moral, la ética y la bioética como limitantes sociales a la protección de las invenciones por la vía de las patentes. Frónesis. [online]. Dic. 2006, vol. 13, No. 3 [cited on Dec. 7, 2011], p. 9-31.
Goodman & Gilman, The Pharmacological basis of therapeutic. 9th edition. Interamericana. 1996 Mexico, p. 47, 1 page.
Merck Index. 14th. N.J. USA 2006; No. 0001034, 0008239, 0005436, 3 pages.
Non-Final Office Action mailed on Mar. 26, 2015, for U.S. Appl. No. 13/762,238, filed Feb. 7, 2013, 9 pages.
Non-Final Office Action mailed on Feb. 3, 2015, for U.S. Appl. No. 14/284,331, filed May 21, 2014, 16 pages.
Non-Final Office Action mailed on Oct. 8, 2015, for U.S. Appl. No. 14/323,925, filed Jul. 3, 2014, 8 pages.
Non-Final Office Action mailed on Nov. 16, 2015, for U.S. Appl. No. 14/092,287, filed Nov. 27, 2013, 11 pages.
Non-Final Office Action mailed on Dec. 31, 2015, for U.S. Appl. No. 14/599,287, filed Jan. 16, 2015, 34 pages.
Notice of Allowance mailed on May 14, 2015, for U.S. Appl. No. 14/284,331, filed May 21, 2014, 9 pages.
Notice of Allowance mailed on Sep. 9, 2015, for U.S. Appl. No. 13/762,238, filed Feb. 7, 2013, 8 pages.
Office Action for Australian Patent Application No. 2009313878, mailed on Apr. 1, 2015, 6 pages.
Office Action for European Patent Application No. 09 760 383.1, mailed on Apr. 22, 2015, 6 pages.
Office Action for Israeli Patent Application No. 212851,mailed on Jan. 20, 2015, 2 pages.
Office Action for Chinese Patent Application No. 2014102460300, mailed on Oct. 26, 2015, 1 page.
Office Action for Australian Patent Application No. 2009313878, mailed on Dec. 8, 2015, 3 pages.
Office Action for Korean Patent Application No. 1020117013302, mailed on Dec. 16, 2015, 13 pages.
Otero José Manuel Prof., La Invencion y las excepciones a la patentabilidad en la Decisdión 486 del Acuerdo de Cartagena. Conferencia sobre Patentes. Quito, 2000. p. 31.
Restriction Requirement mailed on May 8, 2015, for U.S. Appl. No. 14/092,287, filed Nov. 27, 2013, 8 pages.
Restriction Requirement mailed on Jun. 12, 2015, for U.S. Appl. No. 14/599,287, filed Jan. 16, 2015, 7 pages.

(56) References Cited

OTHER PUBLICATIONS

Office Action for New Zealand Patent Application No. 715435, mailed on Feb. 2, 2016, 3 pages.
Office Action dated May 24, 2016 for Canadian Patent Application No. 2,743,642.
Office Action dated May 25, 2016 for Chinese Patent Application No. 201410246030.0.
Office Action dated Jun. 27, 2016 for Korean Patent Application No. 10-2011-7013302.
Office Action dated Aug. 16, 2016 for Korean Patent Application No. 10-2016-7019817.

* cited by examiner

| Cell Line | % reduction in cellular viability | % reduction in Akt (Ser473) Phosphorylation | Caspase 3 activation |
|---|---|---|---|
| MOLT-4 | 52% | 84% | Yes |
| CCRF-SB | 61% | 90% | Yes |
| CEM/C2 | 50% | 71% | Yes |
| CEM/C1 | 57% | 47% | Yes |
| SupB13* | 42% | 85% | No |
| SupB15* | 38% | 20% | No |

| Cell Line | Type | Constitutive Akt (Ser473) Phosphorylation | Reduction in Akt(Ser473) with Compound I |
|---|---|---|---|
| HT | B lymphoma | Yes | Yes |
| CCRF-CEM | T lymphoma | Yes | Yes |
| MOLT-4 | ALL | Yes | Yes |
| SupB13 | ALL | Yes | Yes |
| CEM/C2 | ALL | Yes | Yes |
| CEM/C1 | ALL | Yes | Yes |
| CCRF-SB | ALL | Yes | Yes |
| JURKAT | T lymphoma | Yes | Yes |
| DH82 | Malignant histiocytosis (dog) | Yes | Yes |
| SU-DHL-5 | DLBCL | Yes | Yes |
| SU-DHL-10 | DLBCL | Yes | Yes |
| OCI-LY-19 | DLBCL | Yes | Yes |
| MOLM-14 | AML | Yes | Yes |

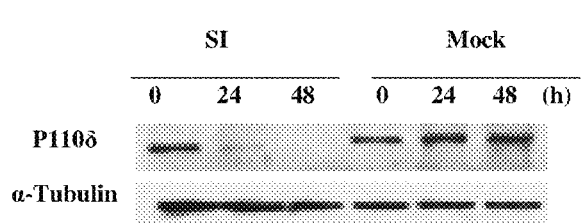
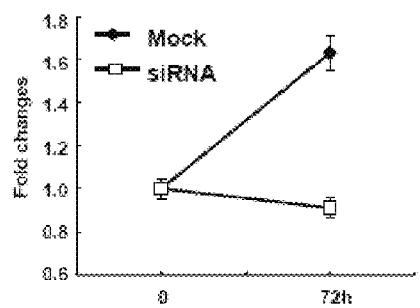
Figure 31A
Figure 31B
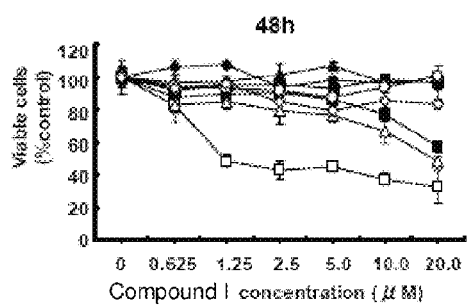
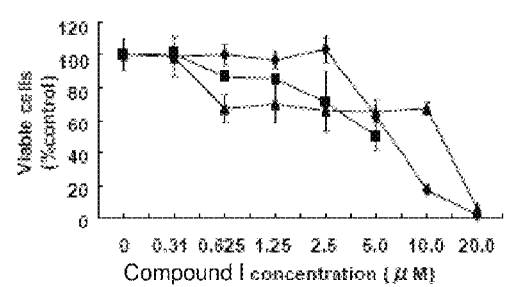
Figure 31C
Figure 31D
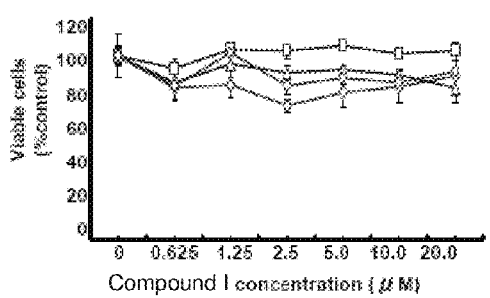
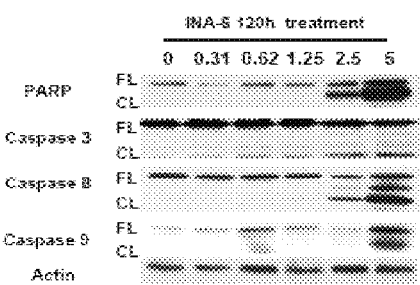
Figure 31E
Figure 31F

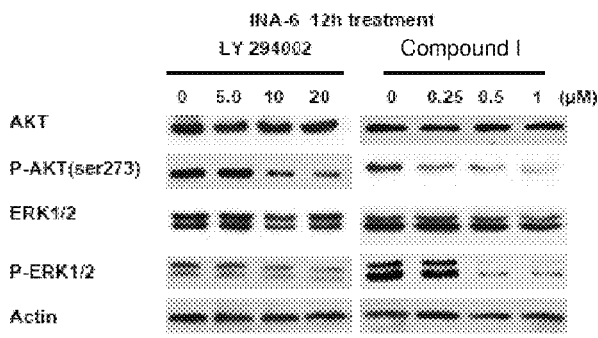
Figure 32A
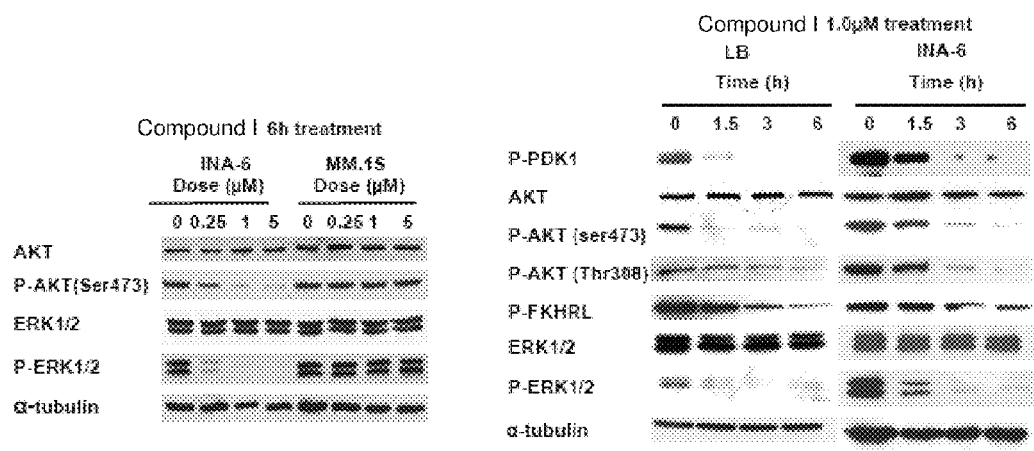
Figure 32B
Figure 32C
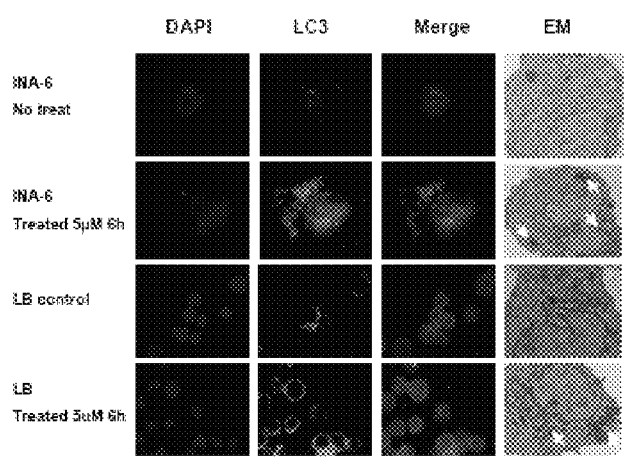
Figure 33A
Figure 33B

THERAPIES FOR HEMATOLOGIC MALIGNANCIES

CROSS-REFERENCE TO RELATED APPLICATIONS

This application is a continuation-in-part of U.S. patent application Ser. No. 12/618,612 filed Nov. 13, 2009, which claims priority from U.S. Provisional Patent Application Nos. 61/245,196 filed Sep. 23, 2009; 61/231,278 filed Aug. 4, 2009; 61/180,768 filed May 22, 2009; 61/155,057 filed Feb. 24, 2009; 61/142,845 filed Jan. 6, 2009; and 61/114,434 filed Nov. 13, 2008. The contents of these applications are incorporated by reference in their entirety.

TECHNICAL FIELD

The invention is in the field of therapeutics and medicinal chemistry. In particular, the invention concerns uses of certain quinazoline derivatives for the treatment of hematologic malignancies and certain other conditions.

BACKGROUND ART

Cell signaling via 3'-phosphorylated phosphoinositides has been implicated in a variety of cellular processes, e.g., malignant transformation, growth factor signaling, inflammation, and immunity. The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring.

PI 3-kinase activation, is believed to be involved in a range of cellular responses including cell growth, differentiation, and apoptosis.

The initial purification and molecular cloning of PI 3-kinase revealed that it was a heterodimer consisting of p85 and p110 subunits. Four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. The patterns of expression of each of these PI3Ks in human cells and tissues are also distinct.

Identification of the p110δ isoform of PI 3-kinase is described in Chantry et al., *J Biol Chem*, 272:19236-41 (1997). It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. The p110β isoform of PI3K may also play a role in PI3K-mediated signaling in certain cancers.

There is a need for a treatment relating to PI3K mediated disorders relating to cancers, inflammatory diseases, and autoimmune diseases.

SUMMARY

The present invention provides a class of quinazolinone type compounds and a method to use these compounds in the treatment of cancer, inflammatory, and autoimmune diseases. In particular, cancers that are hematologic malignancies, such as leukemia and lymphoma, are treated by the methods herein. Also provided are methods of using the quinazolinone compounds in combination with other therapeutic treatments in patients in need thereof.

In one aspect, the invention provides the use of a compound for the manufacture of a medicament for the treatment of a condition in a subject, wherein the condition is cancer or an autoimmune condition; wherein the compound is of formula A,

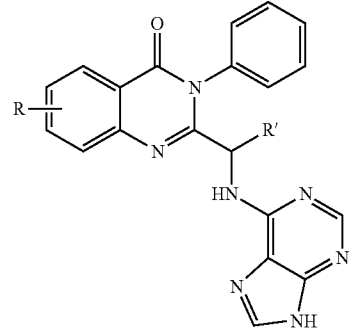

(A)

wherein R is H, halo, or C1-C6 alkyl; R' is C1-C6 alkyl; or a pharmaceutically acceptable salt thereof; and optionally a pharmaceutically acceptable excipient.

In one embodiment, the compound is predominantly the S-enantiomer.

In some of the foregoing embodiments, R is fluoro (F) and is attached to position 5 or 6 of the quinazolinyl ring.

In some of the foregoing embodiments, R is H or F; and R' is methyl, ethyl or propyl.

In some embodiments, the compound is

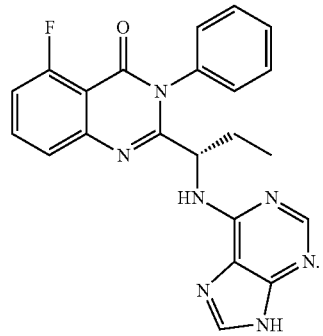

(I″)

In some embodiments, compound is

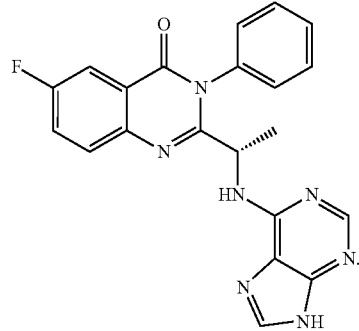

(II″)

In some of the foregoing embodiments, the autoimmune disease is allergic rhinitis, asthma, COPD, or rheumatoid arthritis.

In some of the foregoing embodiments, the condition is cancer.

In some of the foregoing embodiments, the cancer is a hematological malignancy.

In some of the foregoing embodiments, the hematological malignancy is leukemia.

In some of the foregoing embodiments, the hematological malignancy is lymphoma.

In some of the foregoing embodiments, the hematological malignancy is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma, Waldenstrom's macroglobulinemia (WM), B-cell lymphoma and diffuse large B-cell lymphoma (DLBCL).

In some of the foregoing embodiments, the cancer is acute lymphocytic leukemia (ALL).

In some of the foregoing embodiments, the cancer is acute myeloid leukemia (AML).

In some of the foregoing embodiments, the cancer is chronic lymphocytic leukemia (CLL).

In some of the foregoing embodiments, the cancer is multiple myeloma (MM).

In some of the foregoing embodiments, the cancer is B-cell lymphoma.

In some of the foregoing embodiments, the cancer is diffuse large B-cell lymphoma (DLBCL).

In some of the foregoing embodiments, the cancer is B-cell or T-cell ALL.

In some of the foregoing embodiments, the cancer is Hodgkin's lymphoma.

In some of the foregoing embodiments, the cancer is breast, lung, colon, prostate or ovarian cancer.

In some of the foregoing embodiments, the subject is refractory to chemotherapy treatment, or in relapse after treatment with chemotherapy.

In some of the foregoing embodiments, the compound is prepared for administration with at least one additional therapeutic agent.

In some of the foregoing embodiments, the additional therapeutic agent is a proteasome inhibitor.

In some of the foregoing embodiments, the additional therapeutic agent is combined with the compound of Formula A.

In some of the foregoing embodiments, the additional therapeutic agent is selected from the group consisting of ofatumumab, bortezomib (Velcade®), carfilzomib (PR-171), PR-047, disulfuram, lactacystin, PS-519, eponemycin, epoxomycin, aclacinomycin, CEP-1612, MG-132, CVT 63417, PS-341, vinyl sulfone tripeptide inhibitors, ritonavir, PI-083, (+/−) 7 methylomuralide, (−)-7-methylomuralide.

In some of the foregoing embodiments, the additional therapeutic agent is bortezomib.

In some of the foregoing embodiments, the compound is prepared for administration with at least a group of at least two agents, wherein said group of agents is selected from the groups consisting of a-q, a) CHOP (cyclophosphamide, doxorubicin, vincristine, prednisone);
b) R CHOP (rituximab CHOP);
c) hyperCVAD (hyperfractionated cyclophosphamide, vincristine, doxorubicin, dexamethasone, methotrexate, cytarabine);
d) R-hyperCVAD (rituximab-hyperCVAD);
e) FCM (fludarabine, cyclophosphamide, mitoxantrone);
f) R-FCM (rituximab, fludarabine, cyclophosphamide, mitoxantrone);
g) bortezomib and rituximab;
h) temsirolimus and rituximab;
i) temsirolimus and Velcade®;
j) Iodine-131 tositumomab (Bexxar®) and CHOP;
k) CVP (cyclophosphamide, vincristine, prednisone);
l) R-CVP (rituximab-CVP);
m) ICE (iphosphamide, carboplatin, etoposide);
n) R-ICE (rituximab-ICE);
o) FCR (fludarabine, cyclophosphamide, rituximab);
p) FR (fludarabine, rituximab); and
q) D.T. PACE (dexamethasone, thalidomide, cisplatin, Adriamycin®, cyclophosphamide, etoposide).

In some of the foregoing embodiments, the compound of formula A is present in a pharmaceutical composition comprising the compound of formula A and at least one pharmaceutically acceptable excipient.

In another aspect, the invention provides the use of a compound for the manufacture of a medicament for the treatment of a condition in a subject, wherein the condition is selected from the group consisting of multiple myeloma, acute lymphocytic leukemia (ALL), acute myeloid leukemia (AML), chronic lymphocytic leukemia (CLL), B-cell lymphoma, diffuse large B-cell lymphoma (DLBCL), B cell ALL, T cell ALL, Hodgkin's lymphoma, breast, and ovarian cancer, wherein the compound is a compound of formula I" or formula II":

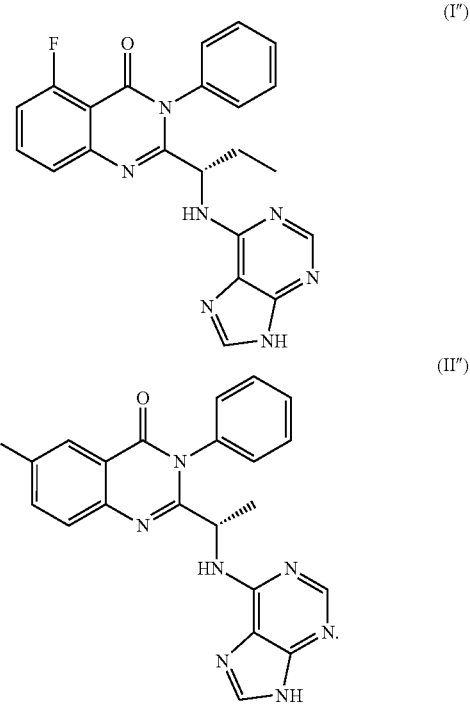

In some of the foregoing embodiments, the subject is refractory to chemotherapy treatment or in relapse after treatment with chemotherapy.

In some of the foregoing embodiments, the subject has a cancer that constitutively expresses Akt phosphorylation activity.

In some of the foregoing embodiments, the subject has a cancer with high p110δ activity and low p110α activity.

In some of the foregoing embodiments, the compound is used in combination with bortezomib.

In another aspect, the invention provides the use of a compound I" or II" in the manufacture of a medicament for treating a hematological cancer, wherein the medicament is prepared for administration with bortezomib or carfilzomib.

In some of the foregoing embodiments, the compound maintains an average blood concentration above the EC50 level for PI3Kδ activation and below the level for EC50 PI3Kγ activation in basophils over a period of at least 12 hours from compound administration.

In some of the foregoing embodiments, the compound maintains an average blood plasma concentration between 100 nM and 1100 nM over a period of at least 12 hours from compound administration.

In some of the foregoing embodiments, the subject is resistant to standard chemotherapeutic treatments.

In some of the foregoing embodiments, the subject has at least one enlarged lymph node.

In some of the foregoing embodiments, the subject is refractory to at least two standard or experimental chemotherapy treatments had at least two prior chemotherapy treatments.

In some of the foregoing embodiments, each chemotherapy treatment is selected from the group consisting of fludarabine, alkylating agents, rituximab, alemtuzumab, and the treatments a-q listed above.

BRIEF DESCRIPTION OF THE DRAWINGS

FIG. 8 shows a summary of the effect of compound I on Akt phosphorylation in many leukemia and lymphoma cell lines.

FIG. 26A shows the PI3K isoform expression in a panel of DLBCL cell lines.

FIG. 31A shows expression of p110 delta from LB and INA-6 cells transfected with p110 delta siRNA (Si) or control siRNA (mock).

FIG. 31B shows a graph of INA-6 cell growth after transfection with p110 delta siRNA (Si) or control siRNA (mock).

FIG. 31C shows the % of viable cells cultured with or without compound I for 48 hours.

FIG. 31D shows the % of viable MM cells after being cultured with compound I at concentrations from 0 to 20 μM for 48 hours.

FIG. 31E shows the % of viable peripheral blood mononuclear cells from healthy donors after being cultured with compound I at various concentrations for 72 hours.

FIG. 31F shows immunoblotting results of lysates from INA-6 cells cultured with compound I (0-5 μM) for 120 hours.

FIG. 32 shows immunoblot AKT and ERK expression profiles after culturing of A) INA-6 cells with compound I or LY294002 for 12 hours; B) INA-6 and MM.1S cells with compound I at various concentrations for 6 hours; C) LB and INA-6 cells with compound I for 0-6 hours.

FIG. 33A shows fluorescent and transmission electron microscopic images of INA-6 and LB MM cells treated with compound I for 6 hours and LC3 accumulation; arrows indicate autophagosomes.

FIG. 33B shows fluorescence microscopy images of INA-6 cells treated with 5 μM of compound I or serum starvation for 6 hours.

FIG. 34 E shows immunoblots of IL-6 in culture supernatants from BMSCs cultured with compound I or control media for 48 hours.

FIG. 35 D shows decreasing Akt and ERK expression of HuVEC cell lysates after being cultured with compound I for 8 hours.

MODES OF CARRYING OUT THE INVENTION

Figure 1:
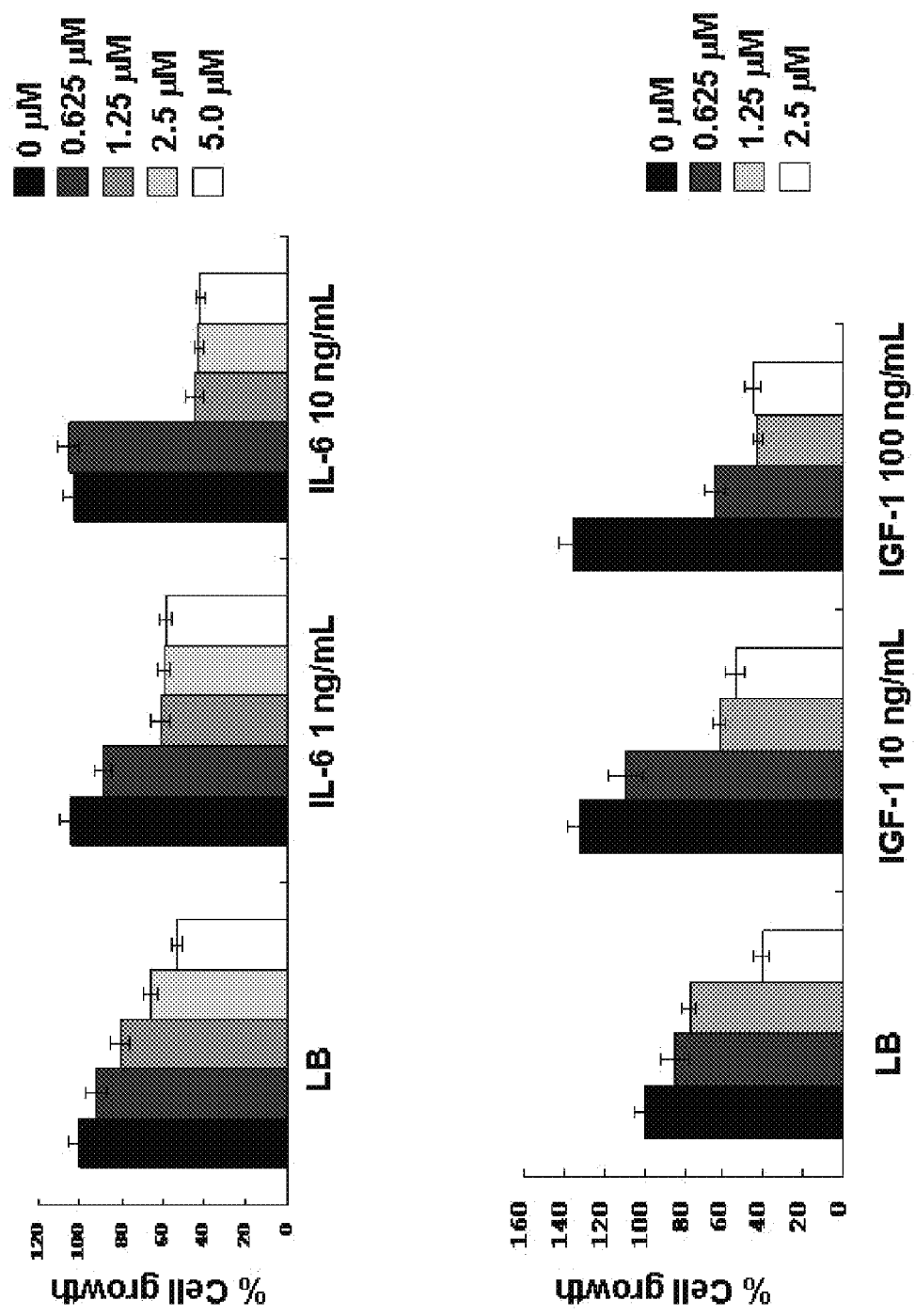
FIG. 1 shows a graphical summary of multiple myeloma (MM) cell growth as a function of varying concentrations of cytokines IGF-1 and IL-6 in combination with compound I, using LB cells.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

The discussion of the general methods given herein is intended for illustrative purposes only. Other alternative methods and embodiments will be apparent to those of skill in the art upon review of this disclosure.

A group of items linked with the conjunction "or" should not be read as requiring mutual exclusivity among that group, but rather should also be read as "and/or" unless expressly stated otherwise. Although items, elements, or components of the invention may be described or claimed in the singular, the plural is contemplated to be within the scope thereof unless limitation to the singular is explicitly stated.

The invention provides methods that relate to a novel therapeutic strategy for the treatment of cancer and inflammatory diseases. In one aspect, the invention provides a method of treating cancer or an autoimmune disease in a subject comprising administering to said subject a compound of formula A wherein R is H, halo, or C1-C6 alkyl; R' is C1-C6 alkyl; or a pharmaceutically acceptable salt thereof; and optionally a pharmaceutically acceptable excipient.

In a particular embodiment, halo is F; and R' is methyl, ethyl or propyl.

In a particular embodiment, R is attached to position 5 of the quinazolinyl ring, having

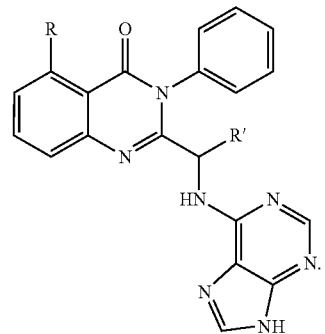

In a particular embodiment, R is attached to position 6 of the quinazolinyl ring, having the structure

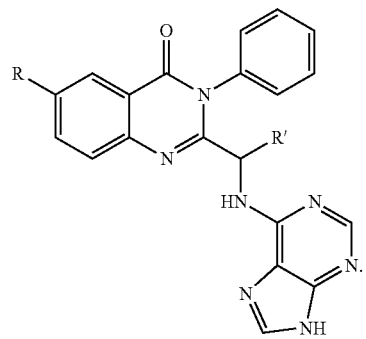

The term 'compound' used herein, unless otherwise specified, refers to a compound of formula A, such as compound I, compound II, or an enantiomer, such as I'' or II'', or an enantiomeric mixture.

The "compound of formula I" or "compound I" refers to the chemical compound 5-fluoro-3-phenyl-2-[1-(9H-purin-6-ylamino)-propyl]-3H-quinazolin-4-one, structure of formula I:

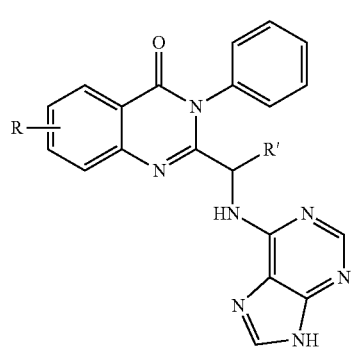

(A)

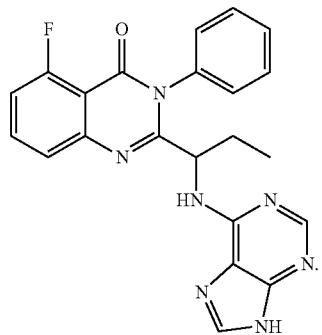

(I)

The S-enantiomer of compound I is shown here, designated I″:

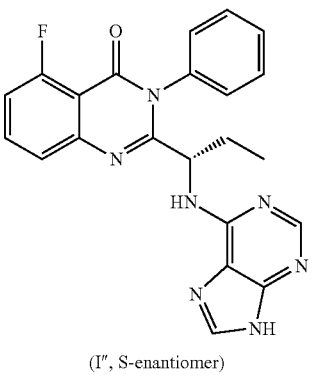 [SMILES: CC[C@H](Nc1ncnc2[nH]cnc12)c1nc2cccc(F)c2c(=O)n1-c1ccccc1]

(I″, S-enantiomer)

The "compound of formula II" or "compound II" refers to the chemical compound 2-(1-(9H-purin-6-ylamino)ethyl)-6-fluoro-3-phenylquinazolin-4(3H)-one, structure of formula II:

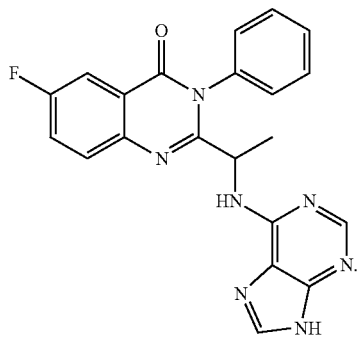

(II)

The S-enantiomer of compound II is shown here, designated II″:

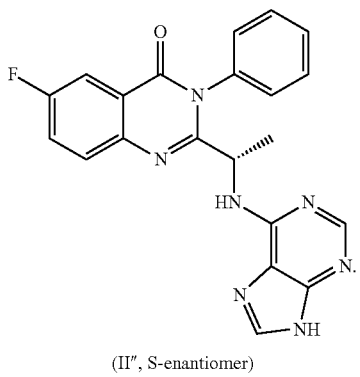 [SMILES: C[C@H](Nc1ncnc2[nH]cnc12)c1nc2ccc(F)cc2c(=O)n1-c1ccccc1]

(II″, S-enantiomer)

In one embodiment, the compound of formula A is a compound of formula I. In another embodiment, the compound of formula A is a compound of formula II. In certain embodiments, the compound is a racemic mixture of R- and S-enantiomers. In certain embodiments, the compound is used as a mixture of enantiomers, and is often enriched with the S-enantiomer. In some embodiments, the compound is predominantly the S-enantiomer. In some embodiments, the compound of formula A, used in the methods described herein is at least 80% S-enantiomer. In certain embodiments, the compound is primarily composed of the S-enantiomer, wherein the compound comprises at least 66-95%, or 85-99% of the S-enantiomer. In some embodiments the compound has an enantiomeric excess (e.e.) of at least 90% or at least 95% of S-enantiomer. In some embodiments the compound has an S-enantiomeric excess (e.e.) of at least 98% or at least 99%. In certain embodiments, the compound comprises at least 95% of the S-enantiomer. In the cellular and patient experiments provided in the Example section, the sample of compound I used was over 95% S-enantiomer.

In specific embodiments, the compound of formula I or II, used in the methods described herein is at least 80% S-enantiomer. In certain embodiments, the compound of formula I or II is primarily composed of the S-enantiomer, wherein the compound comprises at least 66-95%, or 85-99% of the S-enantiomer. In some embodiments the compound of formula I or II has an enantiomeric excess (e.e.) of at least 90% or at least 95% of S-enantiomer. In some embodiments the compound of formula I or II has an S-enantiomeric excess (e.e.) of at least 98% or at least 99%. In certain embodiments, the compound of formula I or II comprises at least 95% of the S-enantiomer. In the cellular and patient experiments provided in the Example section, the sample of compound I used was over 95% S-enantiomer.

In a particular embodiment, the compound selectively inhibits PI3K p110δ compared to other PI3K isoforms.

In a particular embodiment, the autoimmune disease is allergic rhinitis, asthma, COPD, or rheumatoid arthritis.

In a particular embodiment, the cancer is a hematological malignancy and/or solid tumor. In another particular embodiment, the hematological malignancy is leukemia or lymphoma.

In some embodiments, lymphoma is a mature (peripheral) B-cell neoplasm. In specific embodiments, the mature B-cell neoplasm is selected from the group consisting of B-cell chronic lymphocytic leukemia/small lymphocytic lymphoma; B-cell prolymphocytic leukemia; Lymphoplasmacytic lymphoma; Marginal zone lymphoma, such as Splenic marginal zone B-cell lymphoma (+/-villous lymphocytes), Nodal marginal zone lymphoma (+/-monocytoid B-cells), and Extranodal marginal zone B-cell lymphoma of mucosa-associated lymphoid tissue (MALT) type; Hairy cell leukemia; Plasma cell myeloma/plasmacytoma; Follicular lymphoma, follicle center; Mantle cell lymphoma; Diffuse large cell B-cell lymphoma (including Mediastinal large B-cell lymphoma, Intravascular large B-cell lymphoma, and Primary effusion lymphoma); and Burkitt's lymphoma/Burkitt's cell leukemia.

In some embodiments, lymphoma is selected from the group consisting of multiple myeloma (MM) and non-Hodgkin's lymphoma (NHL), mantle cell lymphoma (MCL), follicular lymphoma, Waldenstrom's macroglobulinemia (WM) or B-cell lymphoma and diffuse large B-cell lymphoma (DLBCL).

In a further particular embodiment, leukemia is selected from the group consisting of acute lymphocytic leukemia (ALL), acute myeloid leukemia (AML), chronic lymphocytic leukemia (CLL), and small lymphocytic lymphoma (SLL). Acute lymphocytic leukemia is also known as acute lymphoblastic leukemia and may be used interchangeably herein. Both terms describe a type of cancer that starts from the white blood cells, lymphocytes, in the bone marrow.

In some embodiments, Non-Hodgkin's Lymphoma (NHL) falls into one of two categories, aggressive NHL or indolent NHL. Aggressive NHL is fast growing and may lead to a patient's death relatively quickly. Untreated survival may be measured in months or even weeks. Examples of aggressive NHL includes B-cell neoplasms, diffuse large B-cell lymphoma, T/NK cell neoplasms, anaplastic large cell lymphoma, peripheral T-cell lymphomas, precursor B-lymphoblastic leukemia/lymphoma, precursor T-lymphoblastic leukemia/lymphoma, Burkitt's lymphoma, Adult T-cell lymphoma/leukemia (HTLV1+), primary CNS lymphoma, mantle cell lymphoma, polymorphic post-transplantation lymphoproliferative disorder (PTLD), AIDS-related lymphoma, true histiocytic lymphoma, and blastic NK-cell lymphoma. The most common type of aggressive NHL is diffuse large cell lymphoma.

Indolent NHL is slow growing and does not display obvious symptoms for most patients until the disease has progressed to an advanced stage. Untreated survival of patients with indolent NHL may be measured in years. Non-limiting examples include follicular lymphoma, small lymphocytic lymphoma, marginal zone lymphoma (such as extranodal marginal zone lymphoma (also called mucosa associated lymphoid tissue—MALT lymphoma), nodal marginal zone B-cell lymphoma (monocytoid B-cell lymphoma), splenic marginal zone lymphoma), and lymphoplasmacytic lymphoma (Waldenstrom's macroglobulinemia).

In some cases, histologic transformation may occur, e.g., indolent NHL in patients may convert to aggressive NHL.

In some embodiments, the invention provides methods of treating a patient with aggressive NHL or indolent NHL.

In some embodiments, the invention provides methods of treating a patient with a condition selected from the group consisting of mantle cell lymphoma (MCL), diffuse large B cell lymphoma (DLBCL), follicular lymphoma (FL), acute lymphocytic leukemia (ALL), acute myeloid leukemia (AML), chronic lymphocytic leukemia (CLL), and small lymphocytic lymphoma (SLL), multiple myeloma (MM), and marginal zone lymphoma.

In some embodiments, the methods of the invention are administered to patients with relapsed or refractory conditions.

In another embodiment, the cancer is breast, lung, colon or prostate cancer.

In a particular embodiment, the cancer or autoimmune disease is associated with abnormal PI3K activity compared to PI3K activity in a subject without cancer or without an autoimmune disease.

In a particular embodiment, the preferred subject is refractory to chemotherapy treatment, or in relapse after treatment with chemotherapy. In an alternative embodiment, the subject is a de novo patient.

In a particular embodiment, the method comprises reducing the level of PI3Kδ activity in said patient.

In a particular embodiment, the subject is a human subject.

Subjects that undergo treatment with known therapeutic agents may experience resistance to treatment. For example, although bortezomib was FDA approved for relapsed/refractory, relapsed, and newly diagnosed MM, some patients do not respond and others acquire resistance to bortezomib. In some embodiments, the quinazolinone compound described herein synergistically augments efficacy of a known therapeutic agent. In some embodiments, the compounds described herein can augment any of the therapeutic agents described herein. In more specific embodiments, the compounds described herein synergistically augment proteasome inhibitors. In some of the foregoing embodiments, the subject is resistant to chemotherapeutic treatment. In some of the foregoing embodiments, the subject is resistant to proteasome inhibitors. In some of the foregoing embodiments, the subject is resistant bortezomib or carfilzomib. In one example, the compounds described herein synergistically augment bortezomib-induced MM cytotoxicity. Without being bound by theory, in some embodiments, the compounds discussed herein inhibit bortezomib-induced phosphorylation of AKT. In some embodiments, the methods described herein are used to overcome resistance to proteasome inhibitor treatment. In some embodiments, the invention provides a method to treat a subject that is resistant or has developed a resistance to therapeutic agents.

While not being bound by theory, the synergistic effects between a compound of formula A and conventional therapies may be attributed to the ability of the compound of the invention to induce tumor cell mobilization into peripheral circulation. Inducing the peripheral circulation of the tumor cells increases the ability of conventional therapy to act upon and more effectively neutralize the tumor. This synergy has been demonstrated in CLL patients.

Accordingly, the method comprises administering in addition to a compound of formula A to a patient, a therapeutically effective amount of at least one additional therapeutic agent and/or a therapeutic procedure selected to treat said cancer or autoimmune disease in said patient. "Therapeutic agent" may refer to one or more compounds, as used herein. The therapeutic agent may be a standard or experimental chemotherapy drug. The therapeutic agent may comprise a combination of more than one chemotherapy drug. Typical chemotherapy drug combinations are listed a-q herein. A particular therapeutic agent may be chosen depending on the type of disease being treated. Non-limiting examples of conventional chemotherapeutic treatments for particular hematologic disease are described in later sections. In a particular embodiment, the invention provides a method to treat a hematopoietic cancer patient, e.g., a CLL patient, with bortezomib and a compound of formula A (e.g., formula I, II, I", or II"), wherein the combination provides a synergistic effect.

In a particular embodiment, said therapeutic agent is selected from the following group consisting of bortezomib) (Velcade®, carfilzomib (PR-171), PR-047, disulfuram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, perifosine, rituximab, sildenafil citrate (Viagra®), CC-5103, thalidomide, epratuzumab (hLL2-anti-CD 22 humanized antibody), simvastatin, enzastaurin, Campath-1H®, dexamethasone, DT PACE, oblimersen, antineoplaston A10, antineoplaston AS2-1, alemtuzumab, beta alethine, cyclophosphamide, doxorubicin hydrochloride, PEGylated liposomal doxorubicin hydrochloride, prednisone, prednisolone, cladribine, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I 131 tositumomab, motexafin gadolinium, arsenic trioxide, tipifarnib, autologous human tumor-derived HSPPC-96, veltuzumab, bryostatin 1, anti-CD20 monoclonal antibodies, chlorambucil, pentostatin, lumiliximab, apolizumab, Anti-CD40, and ofatumumab, or a combination thereof. Combinations of therapeutic agents are used in current and experimental therapies such as those combinations a-q listed above.

In some embodiments, the therapeutic agent is preferably a proteasome inhibitor. In some embodiments, the methods comprise administering a compound with a proteasome inhibitor. Proteasome inhibitors include natural and synthetic compounds. Non-limiting examples of proteasome inhibitors include bortezomib, ([(1R)-3-methyl-1-({(2S)-3-phenyl-2-[(pyrazin-2-ylcarbonyl)amino]propanoyl}amino) butyl]boronic acid), which is marketed as 'Velcade®' by Millennium pharmaceuticals; carfilzomib (PR-171) and the oral analog, PR-047, both of which are developed by Proteolix, Inc. Other examples of proteasome inhibitors include disulfuram; lactacystin; synthetic compounds such as PS-519, eponemycin, epoxomycin, and aclacinomycin; calpain inhibitors, such as CEP-1612, MG-132, CVT-63417, PS-341; vinyl sulfone tripeptide inhibitors; ritonavir; PI-083; (+/−)-7-methylomuralide; and (−)-7-methylomuralide. In particular embodiments, the compound of formula A is administered in combination with bortezomib or carfilzomib. In more particular embodiments, the compound of formula I is administered in combination with bortezomib or carfilzomib. In other particular embodiments, the compound of formula II is administered in combination with bortezomib or carfilzomib. In particular embodiments, the compound of formula A is administered in combination with rituximab or ofatumumab. In more particular embodiments, the compound of formula I is administered in combination with rituximab or ofatumumab. In other particular embodiments, the compound of formula II is administered in combination with rituximab or ofatumumab.

In one aspect, the invention provides a pharmaceutical composition comprising a compound of Formula I:

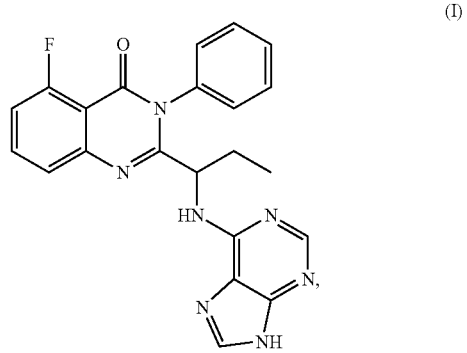 [SMILES: CCC(Nc1ncnc2[nH]cnc12)c1nc2cccc(F)c2c(=O)n1-c1ccccc1]

(I)

or a pharmaceutically acceptable salt thereof; and at least one pharmaceutically acceptable excipient. In one embodiment, the composition is enriched with the S-enantiomer.

In another aspect, the invention provides a pharmaceutical composition comprising a compound of Formula II:

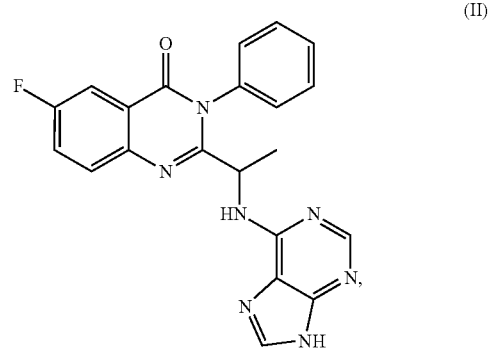 [SMILES: CC(Nc1ncnc2[nH]cnc12)c1nc2ccc(F)cc2c(=O)n1-c1ccccc1]

(II)

or a pharmaceutically acceptable salt thereof; and at least one pharmaceutically acceptable excipient. In one embodiment, the composition is enriched with the S-enantiomer.

In one aspect, the invention provides a method of treating multiple myeloma (MM) in a patient comprising administering a combination of a compound of formula A and an additional therapeutic agent. In some embodiments, formula A is compound I or II. In specific embodiments, formula A is compound I". In other embodiments, formula A is compound II". In some of the foregoing embodiments the additional therapeutic agent is a proteasome inhibitor. In specific embodiments the additional therapeutic agent is bortezomib. In a specific embodiment, the method of treating multiple myeloma in a patient comprises administering compound I" with bortezomib. In a specific embodiment, the method of treating multiple myeloma in a patient comprises administering compound II" with bortezomib. In some of the foregoing embodiments, compound I" or II" has an enantiomeric excess of at least 60%. In some of the foregoing embodiments, compound I" or II" has an enantiomeric excess of at least 70%. In some of the foregoing embodiments, compound I" or II" has an enantiomeric excess of at least 80%. In some of the foregoing embodiments, compound I" or II" has an enantiomeric excess of at least 90%. In some of the foregoing embodiments, compound I" or II" has an enantiomeric excess of at least 95%. In some of the foregoing embodiments, compound I" or II" has an enantiomeric excess of at least 98%. In some of the foregoing embodiments, compound I" or II" has an enantiomeric excess of at least 99%.

In a particular embodiment, a combination of therapeutic agents is administered with a compound of Formula A, wherein said combination is selected from the group consisting of
a) CHOP (cyclophosphamide, doxorubicin, vincristine, prednisone);
b) R-CHOP (rituximab-CHOP);
c) hyperCVAD (hyperfractionated cyclophosphamide, vincristine, doxorubicin, dexamethasone, methotrexate, cytarabine);
d) R-hyperCVAD (rituximab-hyperCVAD);
e) FCM (fludarabine, cyclophosphamide, mitoxantrone);
f) R-FCM (rituximab, fludarabine, cyclophosphamide, mitoxantrone);
g) bortezomib and rituximab;
h) temsirolimus and rituximab;
i) temsirolimus and Velcade®;
j) Iodine-131 tositumomab (Bexxar®) and CHOP;

k) CVP (cyclophosphamide, vincristine, prednisone);
l) R-CVP (rituximab-CVP);
m) ICE (iphosphamide, carboplatin, etoposide);
n) R-ICE (rituximab-ICE);
o) FCR (fludarabine, cyclophosphamide, rituximab);
p) FR (fludarabine, rituximab); and
q) D.T. PACE (dexamethasone, thalidomide, cisplatin, Adriamycin®, cyclophosphamide, etoposide).

In alternative embodiments, the compound is used in combination with a therapeutic procedure. In a particular embodiment, the therapeutic procedure is selected from the group consisting of peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, immunohistochemistry staining method, pharmacological study, low-LET cobalt-60 gamma ray therapy, bleomycin, conventional surgery, radiation therapy, high-dose chemotherapy and nonmyeloablative allogeneic hematopoietic stem cell transplantation.

In a particular embodiment, the method further comprises obtaining a biological sample from said patient; and analyzing said biological sample with an analytical procedure selected from the group consisting of blood chemistry analysis, chromosomal translocation analysis, needle biopsy, fluorescence in situ hybridization, laboratory biomarker analysis, immunohistochemistry staining method, flow cytometry or a combination thereof.

For nomenclature purposes, the quinazolinyl and purinyl components of the compound are numbered accordingly:

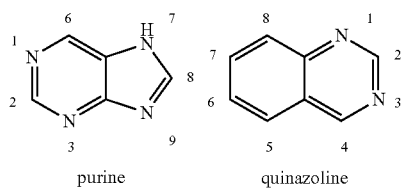 [SMILES: c1ncc2[nH]cnc2n1 ; c1ccc2ncncc2c1]

purine            quinazoline

As used herein, the term "alkyl," includes straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, and the like. The total number of carbon atoms in each such group is sometimes described herein, e.g., when the group can contain up to ten carbon atoms it can be represented as 1-10C or as C1-C10 or C1-10.

"Halo", as used herein, includes fluoro, chloro, bromo and iodo. Fluoro and chloro are often preferred.

The term "selective PI3Kδ inhibitor" or "selective PI3Kβ inhibitor", etc., as used herein, refers to a compound that inhibits the PI3Kδ or PI3Kβ isozyme, respectively, more effectively than at least one other isozymes of the PI3K family. The selective inhibitor may also be active against other isozymes of PI3K, but requires higher concentrations to achieve the same degree of inhibition of the other isozymes. "Selective" can also be used to describe a compound that inhibits a particular PI3-kinase more so than a comparable compound. A "selective PI3Kδ inhibitor" compound is understood to be more selective for PI3Kδ than compounds conventionally and generically designated PI3K inhibitors, e.g., wortmannin or LY294002. Concomitantly, wortmannin and LY294002 are deemed "nonselective PI3K inhibitors." In certain embodiments, compounds of any type that selectively negatively regulate PI3Kδ expression or activity can be used as selective PI3Kδ inhibitors in the methods of the invention. Moreover, compounds of any type that selectively negatively regulate PI3Kδ expression or activity and that possess acceptable pharmacological properties can be used as selective PI3Kδ inhibitors in the therapeutic methods of the invention. Without being bound by theory, targeting p110 delta inhibition with a compound of the invention provides a novel approach for the treatment of hematological malignancies because this method inhibits constitutive signaling resulting in direct destruction of the tumor cell. In addition, without being bound by theory, p110 delta inhibition represses microenvironmental signals which are crucial for tumor cell homing, survival and proliferation.

In an alternative embodiment, compounds of any type that selectively negatively regulate PI3Kβ expression or activity can be used as selective PI3Kβ inhibitors in the methods of the invention. Moreover, compounds of any type that selectively negatively regulate PI3Kβ expression or activity and that possess acceptable pharmacological properties can be used as selective PI3Kβ inhibitors in the therapeutic methods of the invention.

"Treating" as used herein refers to inhibiting a disorder, i.e., arresting its development; relieving the disorder, i.e., causing its regression; or ameliorating the disorder, i.e., reducing the severity of at least one of the symptoms associated with the disorder. In some embodiments, "treating" refers to preventing a disorder from occurring in an animal that can be predisposed to the disorder, but has not yet been diagnosed as having it. "Disorder" is intended to encompass medical disorders, diseases, conditions, syndromes, and the like, without limitation.

"Autoimmune disease" as used herein refers to any group of disorders in which tissue injury is associated with humoral or cell-mediated responses to the body's own constituents.

In another aspect, the invention includes a method for suppressing a function of basophils and/or mast cells, and thereby enabling treatment of diseases or disorders characterized by excessive or undesirable basophil and/or mast cell activity. According to the method, a compound of the invention can be used that selectively inhibits the expression or activity of phosphatidylinositol 3-kinase delta (PI3Kδ) in the basophils and/or mast cells. Preferably, the method employs a PI3Kδ inhibitor in an amount sufficient to inhibit stimulated histamine release by the basophils and/or mast cells. Accordingly, the use of such compounds and other PI3Kδ selective inhibitors can be of value in treating diseases characterized by histamine release, i.e., allergic disorders, including disorders such as chronic obstructive pulmonary disease (COPD), asthma, ARDS, emphysema, and related disorders.

The present invention enables methods of treating such diseases as arthritic diseases, such as rheumatoid arthritis, psoriatic arthritis, monoarticular arthritis, osteoarthritis, gouty arthritis, spondylitis; Behçet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as graft-versus-host disease (GVHD) and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The method can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3Kδ activity will result in reduced amounts of reperfusion injury in such situations.

In certain embodiments, the invention provides methods to treat a solid tumor. In specific embodiments, the cancer is breast, lung, colon, or prostate cancer. In certain embodiments, the invention provides methods to treat a solid tumor that is associated with abnormal or undesirable cellular signaling activity mediated by PI3Kβ. In certain embodiments, a solid tumor is selected from the group consisting of pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Genetic ablation of p110δ has been found to result in mild phenotype restricted to immune system. General observations include organisms that are fertile with no gross anatomical or behavioral abnormalities. A histological examination revealed major organs to appear normal. The total class I PI3K activity was reduced 30-50% in B and T cells. In addition, no increase in susceptibility to infections was observed. Furthermore, the effect on the hematopoietic system includes normal peripheral blood cell counts, the occurrence of lymphoid hypoplasia and the lack of germinal centers in spleen and lymph nodes, a reduced number of B220+IgM+B cell progenitors in bone marrow, a reduced level of serum immunoglobulin, and normal T cell development in the thymus.

Genetic ablation of p110δ affects myeloid and B cell signaling, which is important for oncogenesis. In particular, tyrosine kinase signaling, development, proliferation and survival are affected in myeloid cells. B cell function is most affected and includes proliferation, differentiation, apoptosis, and response to B cell survival factors (BCR, CD40, IL-4, chemokines). Thus, the invention includes methods of treating disease states in which one or more of these myeloid and B cell functions are abnormal or undesirable.

A pan PI3K inhibitor that targets on a molecular level p110α, p110β, p110δ, p110γ, (hvPS34, mTOR, DNA-PK, and others), in turn targets all tissues. The potential clinical indication includes cancer but clinical adverse events include hyperinsulinemia in cancer patients. The advantage of a p110δ selective inhibitor which targets cells mediating inflammation and cancer cells, wherein potential clinical indication include cancer, rheumatoid arthritis, asthma, allergies and COPD, is that treatment is well tolerated, and side effects like hyperinsulinemia are avoided. Thus in one aspect the invention provides a method to treat patients having insulin resistance, or type 2 diabetes, for cancer, rheumatoid arthritis, asthma, allergies, COPD, or other conditions treatable with the compounds of the invention. For patients needing such treatment who have excessive insulin conditions or tendencies, the compounds of the invention are particularly advantageous over pan-PI3K inhibitors. In certain embodiments, a compound of formula I or I" is preferred because it provides therapeutic benefits to treating hematologic malignancies without adversely affecting insulin signaling.

In one embodiment, the invention relates to methods of inhibiting PI3K p110δ. In another embodiment, the invention relates to methods of inhibiting PI3K p110β or p110γ.

In certain embodiments, the method described herein has little or no off target activity. In particular, compound of formula I used in the method show little activity against over 300 protein kinases including those summarized in Table 3 of Example 16. In certain embodiments, the method described herein has no or minimal hyperinsulinemia effects in cancer patients compared to methods comprising the administration of pan-PI3K inhibitors. In certain embodiments, the method described herein is useful in targeting cells mediating Akt phosphorylation, because the compounds of Formula A inhibit Akt phosphorylation. Suitable patients for treatment with the compounds of the invention can thus be selected, in one embodiment, by selecting a patient exhibiting elevated Akt phosphorylation associated with a hematopoietic cancer such as lymphoma, leukemia or multiple myeloma.

The methods herein avoid off-target liabilities and are characterized by negative results in receptor gram screens, having no hERG inhibition and no significant P450 inhibition.

Another advantage of the inventive method is the absence of adverse cardiovascular, respiratory, or central nervous system effects as demonstrated in safety pharmacology studies. In addition, a 28-day toxicity study in rats and dogs demonstrated a high therapeutic index, e.g., a NOAEL (no observable adverse effect level)>>10 μM. This is the highest experimental dose of a chemical at which there is no statistically or biologically significant increase in frequency or severity of a toxicological effect between an exposed group and its appropriate control. Adverse effects are defined as any effects that result in functional impairment and/or pathological lesions that may affect the performance of the whole organism or that reduce an organism's ability to respond to an additional challenge.

In another embodiment, the inventive methods are non-genotoxic in a standard battery of tests.

Another advantage of the invention is that compound selectivity for one or two PI3K isoforms results in an improved safety profile over compounds having pan-PI3K inhibition. In yet another advantage, compound I has a favorable pharmacokinetic profile with good target coverage, and no adverse effects on glucose or insulin levels, and is well tolerated at doses above commonly used therapeutic doses by normal healthy volunteers. Another advantage of the invention includes the ability to treat a wide range of hematological malignancies as demonstrated by the examples herein.

In certain embodiments, the methods of the invention are directed towards treating a cancer or an autoimmune disease. In certain embodiments, the cancer is a hematological malignancy. In specific embodiments, the hematological malignancy is selected from the group consisting of acute lymphocytic leukemia (ALL), acute myeloid leukemia (AML), chronic lymphocytic leukemia (CLL), multiple myeloma (MM), and non-Hodgkin lymphoma (NHL). In certain embodiments, the non-Hodgkin lymphoma is selected from the group consisting of large diffuse B-cell lymphoma (LDBCL), mantle cell lymphoma (MCL), Waldenstrom's macroglobulinemia (WM) and lymphoplasmacytic lymphoma.

PI3K is implicated in many hematological malignancies and preclinical proof of concept relating to treatment with compound I has been established. The table below summarizes particular hematological malignancies and the method of action on the primary patient cell or disease cell line.

| Indication | Effects of compounds of formula A |
| --- | --- |
| Chronic Lymphocytic Leukemia (CLL) | Primary patient cells<br>Induces apoptosis<br>Blocks survival factors |
| Acute Myelogenous Leukemia (AML) | Primary patient cells<br>Blocks PI3K signaling<br>Inhibits proliferation |
| Acute Lymphocytic Leukemia (ALL) | Cell Lines<br>Blocks PI3K signaling<br>Induces apoptosis |
| Non-Hodgkin's Lymphomas (NHL) (MCL, DLBCL, FL) | Cell Lines<br>Blocks PI3K signaling<br>Induces apoptosis |
| Multiple Myeloma (MM) | Primary patient cells<br>P110 δ overexpressed in 24/24 samples<br>Induces apoptosis |

Figure 9:
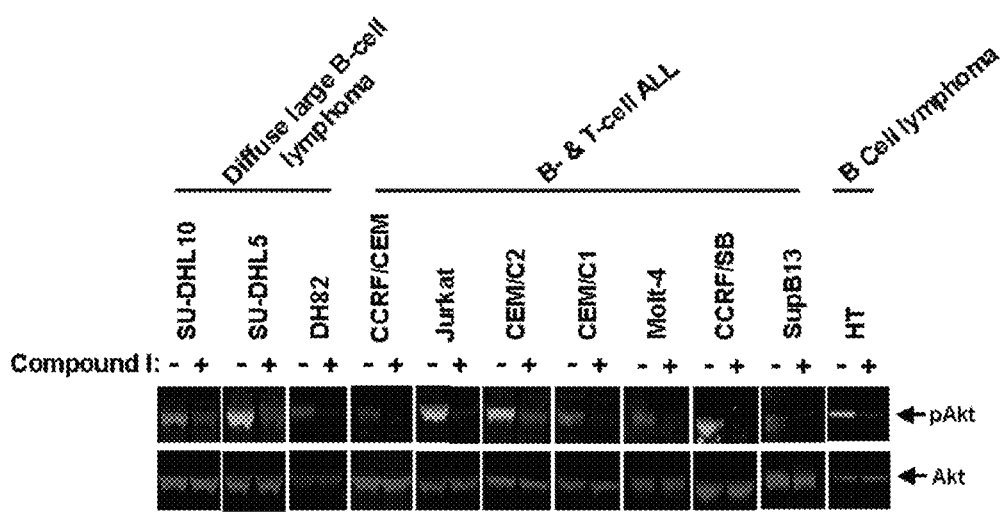
FIG. 9 shows SDS-PAGE images and displays of Akt and pAkt in various hematopoietic cancer cell lines as a function of the presence or absence of compound I, showing compound I inhibits Akt phosphorylation.

Data provided herein demonstrates that the compounds of the invention are useful to treat lymphomas and leukemias. Lymphomas and leukemias generally express the delta isoform of p110 selectively, e.g., FIG. 15 demonstrates that p110δ is prevalent in most lymphoma cell lines, while p110α is not generally observed. Moreover, data presented in FIG. 16A shows that cell cultures from six different leukemia cell lines were sensitive to Compound I, and were strongly affected by 5-10 micromolar concentrations of this compound. FIGS. 8 and 9 support compound I as reducing Akt (Ser473) production in several cell lines.

Figure 13:
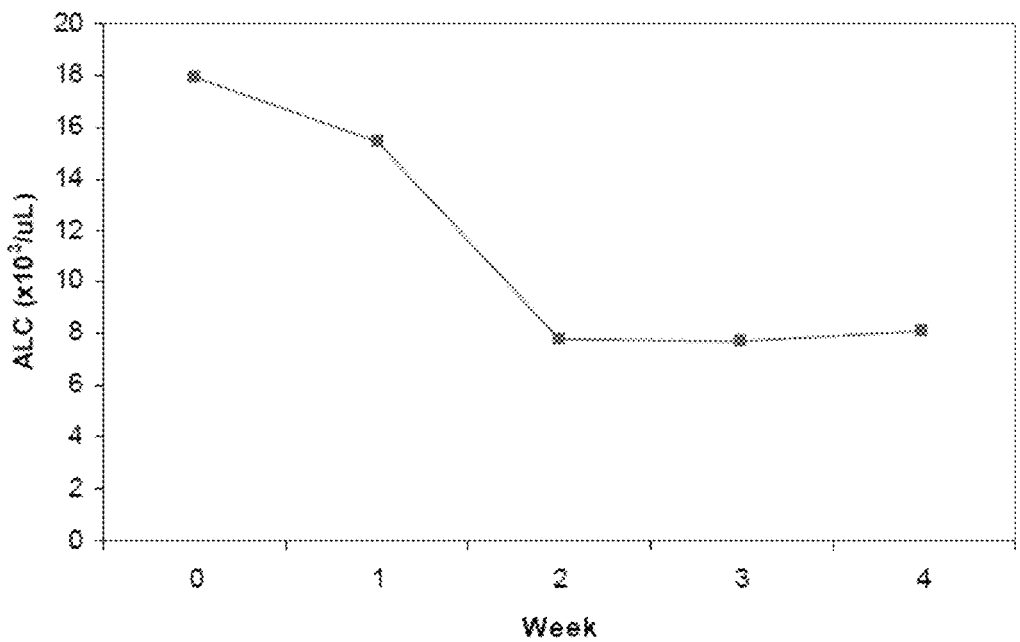
FIG. 13 shows the ALC (absolute lymphocyte count) in the blood of a patient over a period of 4 weeks after 28 days (1 cycle) of treatment with the compound of formula I.

CLL, for example, produces mainly p110δ and to a lesser extent p110γ for signaling purposes, thus compounds that inhibit p110δ and/or p110γ are expected to exhibit selective cytotoxicity towards these cells. In Example 3, for example, shows dose-dependent cytotoxicity for compound I (FIG. 3), in CLL cells, including cells taken from poor prognosis patients (FIG. 19), and cells from patients shown to be resistant to other CLL treatments (FIG. 20). In addition, Example 13 and FIG. 13 demonstrate that compound I administered to a CLL patient at a rate of 50 mg BID for a 28-day cycle provides a significant therapeutic effect. An ALC concentration percent decrease in lymphocytes is observed. Thus in one aspect, the invention provides methods for treating CLL patients with drug-resistant CLL using compounds of Formula A. On the other hand, Example 17 suggests that a fibroblast cell line relying mainly on p110α for signaling was not sensitive to Compound I. Thus in one aspect, patient selection can include excluding patients having a cancer that relies mainly on p110α for signaling.

The compounds of Formula A are also useful to treat lymphoma, including both B-cell and T-cell lymphomas. Data in FIG. 4 demonstrates that six different ALL cell lines were sensitive to Compound I, which caused a significant reduction in cell viability in all six cell lines.

Figure 12:
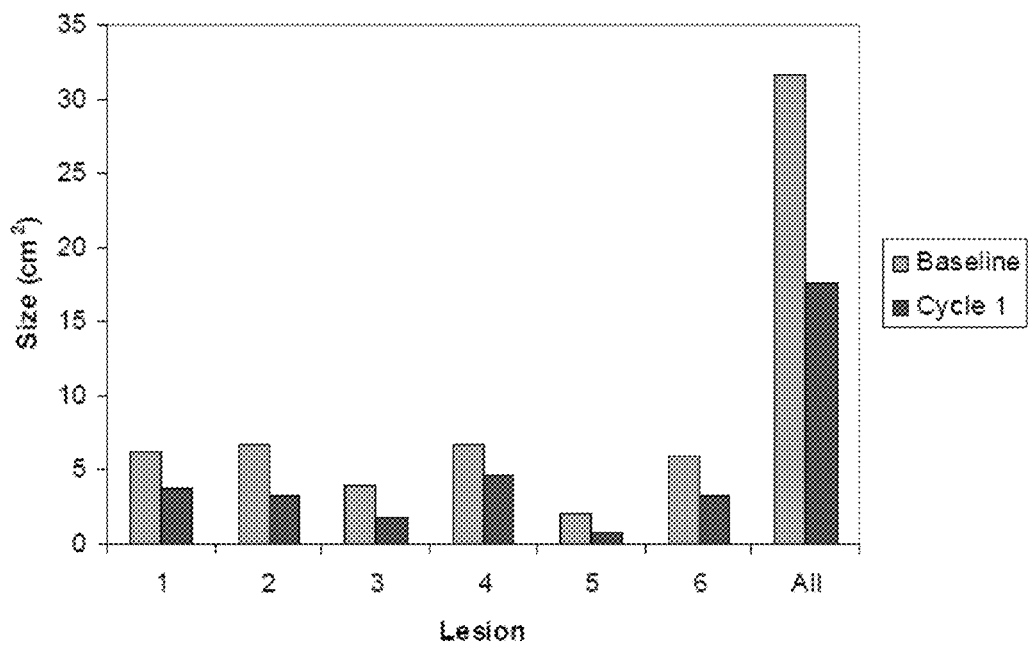
FIG. 12 shows the comparison of lesion areas in a human patient diagnosed with mantle cell lymphoma after 28 days (1 cycle) of treatment with compound I and lesion areas prior to treatment.
Figure 14:
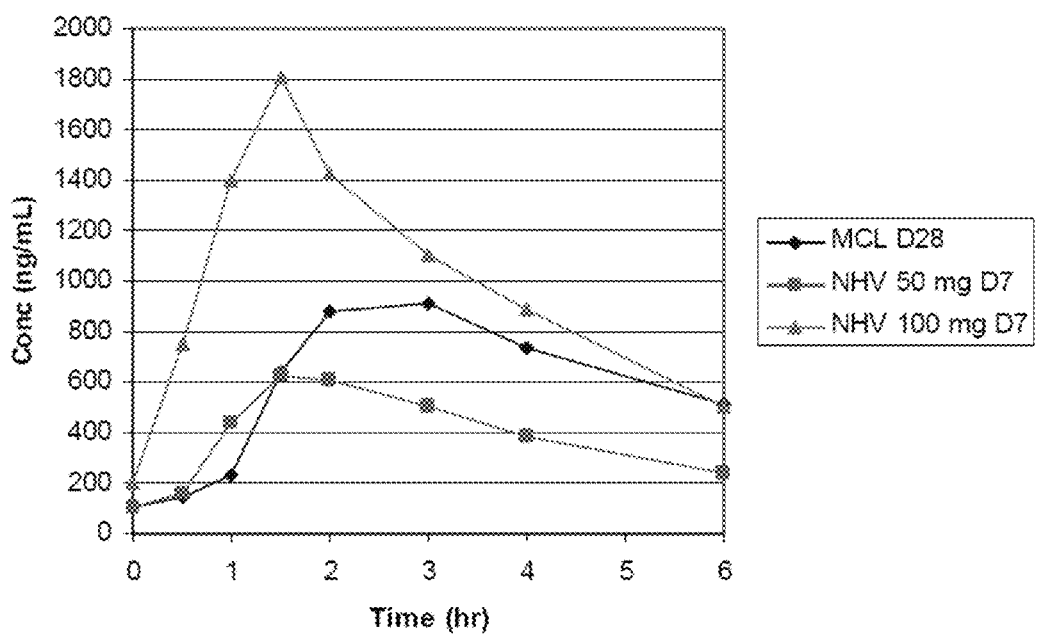
FIG. 14 shows the concentration of compound I in the blood of patients with and without mantle cell lymphoma (MCL) over 6 hours after administration (50 mg BID) at day 28, compared to the concentration in the blood of a normal healthy volunteer at day 7 (D7) using the same dosing schedule or dosing with 100 mg BID of Compound I.

FIG. 12 and Example 12 demonstrate that mantle cell lymphoma patients treated with 50 mg BID of Compound I for 28 days experienced on average a 44% decrease in tumor burden. Moreover, FIG. 14 demonstrates that an MCL patient at the end of the 28 day cycle experienced similar plasma levels of Compound I following administration of a 50 mg dose to that observed in a normal healthy volunteer (NHV); thus the compound does not build up excessively over the course of a cycle of treatment, nor does the patient become tolerant by increased metabolism over the course of a treatment cycle.

In addition, the compounds of Formula A, or Formula I, are useful to treat hematopoietic cancers that constitutively express Akt phosphorylation activity. Example 8, and FIGS. 8 and 9 list cancer cell lines that demonstrate constitutive Akt phosphorylation, including B-cell lymphomas, T-cell lymphomas, ALL, malignant histiocytosis, DLBCL and AML. Exposure of the cell to compound I results in the reduction of Akt phosphorylation. See also Example 19, which shows that constitutive Akt phosphorylation was inhibited by Compound I in 13 of 13 cell lines.

Figure 6:
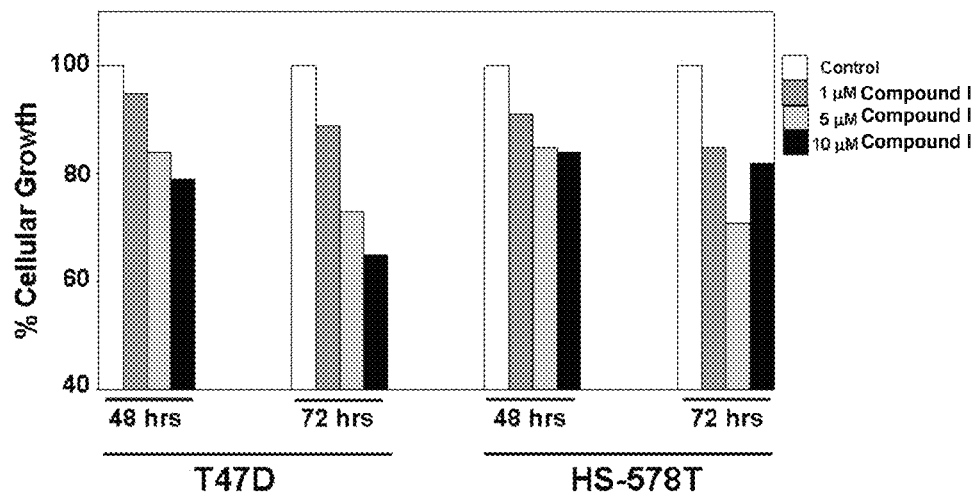
FIG. 6 shows a graphical summary of the effect of varying concentration of compound I on cellular growth in breast cancer T47D and HS-578T cell lines at 48 hrs and 72 hrs.
Figure 10:
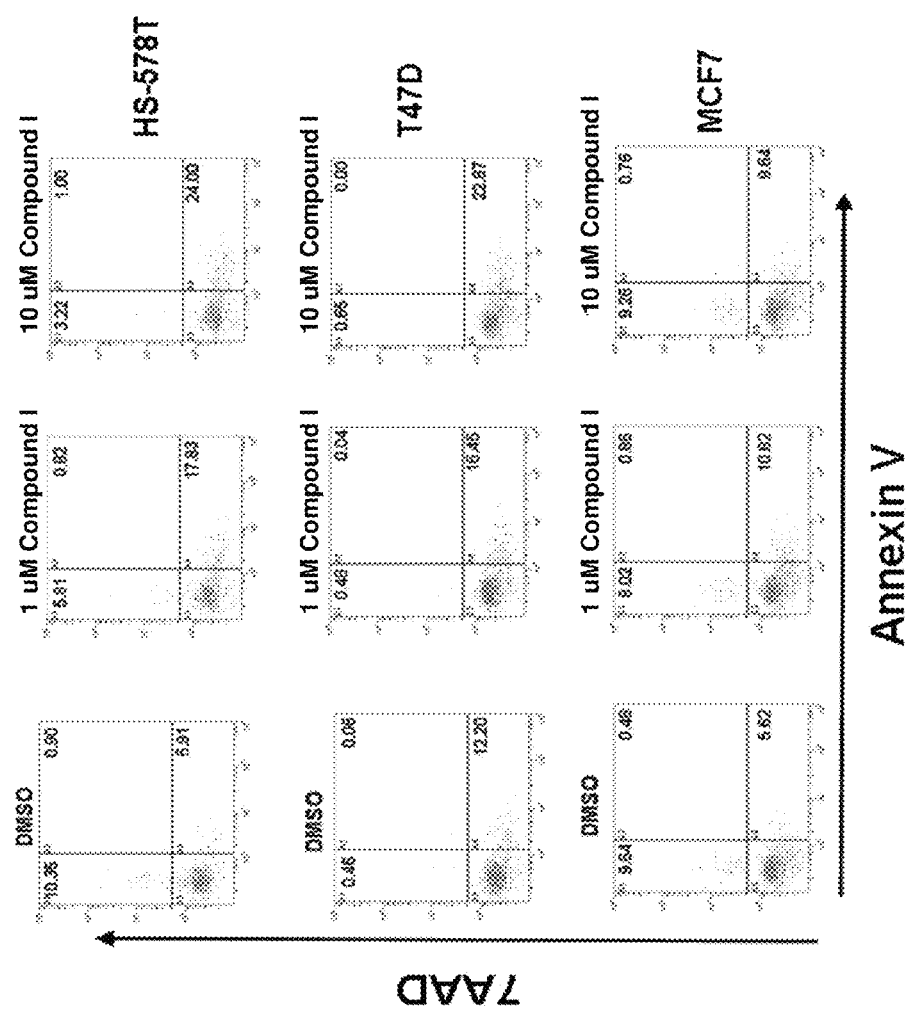
FIG. 10 shows graphical summaries of apoptotic and viable cell populations in breast cancer cell lines as a function of varying concentrations of compound formula I, demonstrating that the compound induces apoptosis.

In certain embodiments, the cancer is a solid tumor. In specific embodiments, the cancer is breast, ovarian, lung, colon, or prostate cancer. FIG. 6, for example, shows that Compound I reduces cellular proliferation of two breast cancer cell lines, and FIG. 10 illustrates cytotoxicity to three different breast cancer cell lines. Similarly, FIG. 7 demonstrates that Compound I is cytotoxic to two ovarian cancer cell lines.

For the treatment of a solid tumor, it is advantageous to use a compound of Formula A that expresses good activity (e.g., $IC_{50}$ less than about 1 μM, and preferably less than about 250 nM—see Example 15) against p110β, since solid tumors often utilize this isozyme rather than or more than p110δ. Thus a compound of formula A that has an $IC_{50}$ less than about 250 nM is preferred for treatment of a solid tumor; compound I, I", II, or II" is suitable for this use, as demonstrated herein.

In some embodiments, the subject for treatments described herein as one who has been diagnosed with at least one of the conditions described herein as treatable by the use of a compound of Formula A. In some embodiments, the subject has been diagnosed with a cancer named herein, and has proven refractory to treatment with at least one conventional chemotherapeutic agent. For instance, patients who have failed to respond to treatments such as proteasome inhibitors, autologous stem cell transplant, CHOP regimens, rituximab, fludarabine, alemtuzumab, conventional anticancer nucleoside analogues and alkylating agents frequently respond to the methods of treatment described herein. Thus, in one embodiment, the treatments of the invention are directed to patients who have received one or more than one such treatment.

In certain embodiments, the autoimmune disease is allergic rhinitis, asthma, chronic obstructive pulmonary disease (COPD), or rheumatoid arthritis.

In certain embodiments, the methods of the invention are directed to B-cell, or B lymphocyte, related diseases. B-cells play a role in the pathogenesis of autoimmune diseases.

The compounds of Formula A (particularly Formulas I, I", II and II") are suitable for treating a variety of subjects having the conditions described herein, especially hematological cancers in humans. In some embodiments, the subject selected for treatment of a hematological malignancy that is a subject experiencing relapse after other treatments or is refractory to other treatments. In some embodiments, the subject is selected for treatment of a hematological malignancy that is resistant to other cancer drugs. In some embodiments, the subject is selected for treatment of a hematological malignancy that exhibits a high level of p110δ activity. In some embodiments, the subject is selected for treatment of a hematological malignancy that exhibits a relatively low level of p110α activity. In some embodiments, the subject is selected for treatment of a hematological malignancy that constitutively expresses Akt phosphorylation activity.

In one embodiment, the method described herein comprises administering to a subject a compound of formula A described herein, in combination with a therapy used to treat cancer or an autoimmune disease. "Therapy" or "treatment", as used herein, is a treatment of cancer or an autoimmune disease by any well-known conventional or experimental form of treatment used to treat cancer or an autoimmune disease that does not include the use of a compound of formula A. In certain embodiments, the combination of a compound of formula A with a conventional or experimental therapy used to treat cancer or an autoimmune disease provides beneficial and/or desirable treatment results superior to results obtained by treatment without the combination. In certain embodiments, therapies used to treat cancer or an autoimmune disease are well-known to a person having ordinary skill in the art and are described in the literature. Therapies include, but are not limited to, chemotherapy, combinations of chemotherapy, biological therapies, immunotherapy, radioimmunotherapy, and the use of monoclonal antibodies, and vaccines.

In some of the foregoing embodiments, the combination method provides for a compound of formula A administered simultaneously with or during the period of administration of the therapy. In some of the foregoing embodiments the compound of formula A is administered simultaneously with the other chemotherapeutic treatment. In certain embodiments, the combination method provides for a compound of formula A administered prior to or after the administration of the therapy.

In some of the foregoing embodiments, the subject is refractory to at least one standard or experimental chemotherapy. In some of the foregoing embodiments, the subject is refractory to at least two standard or experimental chemotherapies. In some of the foregoing embodiments, the subject is refractory to at least three standard or experimental chemotherapies. In some of the foregoing embodiments, the subject is refractory to at least four standard or experimental chemotherapies.

In some of the foregoing embodiments, the subject is refractory to at least one standard or experimental chemotherapy selected from the group consisting of fludarabine, rituximab, alkylating agents, alemtuzumab and the chemotherapy treatments a-q listed above.

In some of the foregoing embodiments, the subject is refractory to at least two standard or experimental chemotherapies selected from the group consisting of fludarabine, rituximab, alkylating agents, alemtuzumab and the chemotherapy treatments a-q listed above.

In some of the foregoing embodiments, the subject is refractory to at least three standard or experimental chemotherapies selected from the group consisting of fludarabine, rituximab, alkylating agents, alemtuzumab and the chemotherapy treatments a-q listed above.

In some of the foregoing embodiments, the subject is refractory to at least four standard or experimental chemotherapies selected from the group consisting of fludarabine, rituximab, alkylating agents, alemtuzumab and the chemotherapy treatments a-q listed above.

The exact details regarding the administration of the combination may be determined experimentally. The refinement of sequence and timing of administering a compound of formula A with a selected therapy will be tailored to the individual subject, the nature of the condition to be treated in the subject, and generally, the judgment of the attending practitioner.

Non-limiting examples of experimental or standard therapy are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Treatment of non-Hodgkin's lymphomas, especially of B cell origin, include, but are not limited to use of monoclonal antibodies, standard chemotherapy approaches (e.g., CHOP, CVP, FCM, MCP, and the like), radioimmunotherapy, and combinations thereof, especially integration of an antibody therapy with chemotherapy.

Non-limiting examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD 74. Non-limiting examples of experimental antibody agents used in treatment of Non-Hodgkin's lymphoma/B-cell cancers include ofatumumab, ha20, PRO131921, alemtuzumab, galiximab, SGN- 40, CHIR-12.12, epratuzumab, lumiliximab, apolizumab, milatuzumab, and bevacizumab. Any of the monoclonal antibodies can be combined with rituximab, fludarabine, or a chemotherapy agent/regimen.

Non-limiting examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP).

Non-limiting examples of radioimmunotherapy for Non-Hodgkin's lymphoma/B-cell cancers include yttrium-90-labeled ibritumomab tiuxetan, and iodine-131-labeled tositumomab. These therapeutic agents are approved for use in subjects with relapsed or refractory follicular or low-grade lymphoma.

Therapeutic treatments for mantle cell lymphoma include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide).

Another approach to treating mantle cell lymphoma includes immunotherapy such as using monoclonal antibodies like Rituximab (Rituxan). Rituximab is also effective against other indolent B-cell cancers, including marginal-zone lymphoma, WM, CLL and small lymphocytic lymphoma. A combination of Rituximab and chemotherapy agents is especially effective. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual patient's tumor. A lymphoma vaccine example is GTOP-99 (MyVax®).

Another approach to treating mantle cell lymphoma includes autologous stem cell transplantation coupled with high-dose chemotherapy.

Another approach to treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews; Jares, P.* 2007). Non-limiting examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CCI-779), Everolimus (RAD001), BMS-345541, Curcumin, Vorinostat (SAHA), Thalidomide, lenalidomide (Revlimid®, CC-5013), and Geldanamycin (17-AAG).

Non-limiting examples of other therapeutic agents used to treat Waldenstrom's Macroglobulinemia include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Non-limiting examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Non-limiting examples of therapeutic procedures used to treat Waldenstrom's Macroglobulinemia include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Non-limiting examples of other therapeutic agents used to treat Chronic Lymphocytic Leukemia (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In certain embodiments, the method comprises administering in addition to a compound of I or II to said patient, a therapeutically effective amount of at least one therapeutic agent and/or therapeutic procedure selected to treat said cancer or autoimmune disease in said patient. In certain embodiments, the method comprises administering in addition to a compound of I or II to said patient, a therapeutically effective amount of a combination of therapeutic agents selected from the group consisting of a) CHOP (cyclophosphamide, doxorubicin, vincristine, prednisone); b) R-CHOP (rituximab-CHOP); c) hyperCVAD (hyperfractionated cyclophosphamide, vincristine, doxorubicin, dexamethasone, methotrexate, cytarabine); d) R-hyperCVAD (rituximab-hyperCVAD); e) FCM (fludarabine, cyclophosphamide, mitoxantrone); f) R-FCM (rituximab, fludarabine, cyclophosphamide, mitoxantrone); g) bortezomib and rituximab; h) temsirolimus and rituximab; i) temsirolimus and Velcade®; j) Iodine-131 tositumomab (Bexxar®) and CHOP; k) CVP (cyclophosphamide, vincristine, prednisone); l) R-CVP (rituximab-CVP); m) ICE (iphosphamide, carboplatin, etoposide); n) R-ICE (rituximab-ICE); o) FCR (fludarabine, cyclophosphamide, rituximab); and p) FR (fludarabine, rituximab).

The compounds of the invention may be formulated for administration to animal subject using commonly understood formulation techniques well known in the art. Formulations which are suitable for particular modes of administration and for the compounds of formula A may be found in *Remington's Pharmaceutical Sciences*, latest edition, Mack Publishing Company, Easton, Pa.

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, $2^{nd}$ ed., London (1988).

A compound of the present invention can be administered as the neat chemical, but it is typically preferable to administer the compound in the form of a pharmaceutical composition or formulation. Accordingly, the present invention also provides pharmaceutical compositions that comprise a compound of formula A and a biocompatible pharmaceutical carrier, adjuvant, or vehicle. The composition can include the compound of Formula A as the only active moiety or in combination with other agents, such as oligo- or polynucleotides, oligo- or polypeptides, drugs, or hormones mixed with excipient(s) or other pharmaceutically acceptable carriers. Carriers and other ingredients can be deemed pharmaceutically acceptable insofar as they are compatible with other ingredients of the formulation and not deleterious to the recipient thereof.

The pharmaceutical compositions are formulated to contain suitable pharmaceutically acceptable carriers, and can optionally comprise excipients and auxiliaries that facilitate processing of the active compounds into preparations that can be used pharmaceutically. The administration modality will generally determine the nature of the carrier. For example, formulations for parenteral administration can comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants), and the like.

Alternatively, formulations for parenteral use can comprise dispersions or suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxy-methylcellulose, sorbitol, or dextran. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the Eudragit® series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing the active compound of Formula A also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See., e.g., Prescott (Ed.), *Methods in Cell Biology*, Vol. XIV, p. 33, Academic Press, New York (1976).

The pharmaceutical compositions comprising the compound of Formula A in dosages suitable for oral administration can be formulated using pharmaceutically acceptable carriers well known in the art. The preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragée cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or excipients, which include, without limitation:

a) diluents, such as sugars, including lactose, dextrose, sucrose, mannitol, or sorbitol;

b) binders, such as magnesium aluminum silicate, starch from corn, wheat, rice, potato, etc.;
c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;
d) disintegrating or solubilizing agents such as cross-linked polyvinyl pyrrolidone, starches, agar, alginic acid or a salt thereof, such as sodium alginate, or effervescent compositions;
e) lubricants, such as silica, talc, stearic acid or its magnesium or calcium salt, and polyethylene glycol;
f) flavorants and sweeteners;
g) colorants or pigments, e.g., to identify the product or to characterize the quantity (dosage) of active compound; and
h) other ingredients, such as preservatives, stabilizers, swelling agents, emulsifying agents, solution promoters, salts for regulating osmotic pressure, and buffers.

In some preferred oral formulations, the pharmaceutical composition comprises at least one of the materials from group (a) above, or at least one material from group (b) above, or at least one material from group (c) above, or at least one material from group (d) above, or at least one material from group (e) above. Preferably, the composition comprises at least one material from each of two groups selected from groups (a)-(e) above.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragée cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The pharmaceutical composition can be provided as a salt of the active compound. Salts tend to be more soluble in aqueous or other protonic solvents than the corresponding free acid or base forms. Pharmaceutically acceptable salts are well known in the art. Compounds that contain acidic moieties can form pharmaceutically acceptable salts with suitable cations. Suitable pharmaceutically acceptable cations include, for example, alkali metal (e.g., sodium or potassium) and alkaline earth (e.g., calcium or magnesium) cations.

Compounds of structural formula (A) that contain basic moieties can form pharmaceutically acceptable acid addition salts with suitable acids. For example, Berge, et al., describe pharmaceutically acceptable salts in detail in *J Pharm Sci*, 66:1 (1977). The salts can be prepared in situ during the final isolation and purification of the compounds of the invention or separately by reacting a free base function with a suitable acid.

Representative acid addition salts include, but are not limited to, acetate, adipate, alginate, citrate, aspartate, benzoate, benzenesulfonate, bisulfate, butyrate, camphorate, camphorolsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate or sulfate, nicotinate, 2-naphthalenesulfonate, oxalate, pamoate, pectinate, persulfate, 3-phenylpropionate, picrate, pivalate, propionate, succinate, tartrate, thiocyanate, phosphate or hydrogen phosphate, glutamate, bicarbonate, p-toluenesulfonate, and undecanoate. Examples of acids that can be employed to form pharmaceutically acceptable acid addition salts include, without limitation, such inorganic acids as hydrochloric acid, hydrobromic acid, sulfuric acid, and phosphoric acid, and such organic acids as oxalic acid, maleic acid, succinic acid, and citric acid.

Basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain alkyl halides such as decyl, lauryl, myristyl, and stearyl chlorides, bromides, and iodides; arylalkyl halides such as benzyl and phenethyl bromides; and others. Products having modified solubility or dispersibility are thereby obtained.

Compositions comprising a compound of the invention formulated in a pharmaceutical acceptable carrier can be prepared, placed in an appropriate container, and labeled for treatment of an indicated condition. Accordingly, there also is contemplated an article of manufacture, such as a container comprising a dosage form of a compound of the invention and a label containing instructions for use of the compound. Kits are also contemplated under the invention. For example, the kit can comprise a dosage form of a pharmaceutical composition and a package insert containing instructions for use of the composition in treatment of a medical condition. In either case, conditions indicated on the label can include treatment of inflammatory disorders, cancer, etc.

Methods of Administration

Pharmaceutical compositions comprising a compound of formula A can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullarly, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT™.

Surgical techniques include implantation of depot (reservoir) compositions, osmotic pumps, and the like. A preferred route of administration for treatment of inflammation can be local or topical delivery for localized disorders such as arthritis, or systemic delivery for distributed disorders, e.g., intravenous delivery for reperfusion injury or for systemic conditions such as septicemia. For other diseases, including those involving the respiratory tract, e.g., chronic obstructive pulmonary disease, asthma, and emphysema, administration can be accomplished by inhalation or deep lung administration of sprays, aerosols, powders, and the like.

In some foregoing embodiments, the compound of formula A is administered before, during, or after administration of chemotherapy, radiotherapy, and/or surgery. The formulation and route of administration chosen will be tailored to the individual subject, the nature of the condition to be treated in the subject, and generally, the judgment of the attending practitioner.

The therapeutic index of the compound of formula A can be enhanced by modifying or derivatizing the compounds for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described (see for example, Pietersz, et al., *Immunol Rev,* 129:57 (1992); Trail, et al., *Science,* 261:212 (1993); and Rowlinson-Busza, et al., *Curr Opin Oncol,* 4:1142 (1992)). Tumor-directed delivery of these compounds enhances the therapeutic benefit by, inter alia, minimizing potential nonspecific toxicities that can result from radiation treatment or chemotherapy. In another aspect, the compound of formula A and radioisotopes or chemotherapeutic agents can be conjugated to the same anti-tumor antibody.

The characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Thus, for any compound used in the method of the invention, a therapeutically effective dose can be estimated initially from biochemical and/or cell-based assays. Then, dosage can be formulated in animal models to achieve a desirable circulating concentration range that modulates expression or activity of a particular PI3K isoform or combination of isoforms. As human studies are conducted, further information will emerge regarding the appropriate dosage levels and duration of treatment for various diseases and conditions.

Although compounds of the invention are well tolerated, an example of a limit to the treatment dosage is elevated liver function tests (LFT). LFT involve standard clinical biochemistry tests on the patient's serum or plasma to provide information about the state of a patient's liver. Levels, such as alanine transaminase, aspartate transaminase, alkaline phosphatase, bilirubin, and gamma glutamyl transpeptidase, that are outside the normal range can signal possible liver toxicity. Dosing of the therapeutic compound can be adjusted to avoid or reduce elevated liver function test values and subsequent potential for liver toxicity. For instance, a subject may be administered escalating doses of a compound. At a certain dose amount, the subject begins to develop elevated LFT levels outside a normal range, signaling potential liver toxicity at that dosage. In response, the dosage may be reduced to an amount such that LFT levels are reduced to an acceptable range as judged by the treating physician, e.g. a level that is in the range normal for the subject being treated, or within about 25% to 50% of normal. Therefore, liver function tests can be used to titrate the administration dosage of a compound.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which typically is expressed as the ratio LD50/ED50. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the $ED_{50}$ with little or no toxicity.

Dosage may be limited by treatment-related toxicity symptoms. Such symptoms besides elevated liver function tests include anemia, vision blurring, diarrhea, vomiting, fatigue, mucositis, peripheral edema, pyrexia, peripheral neuropathy, pleural effusion, night sweats, and orthopnea, or a combination thereof. At a certain dose amount, if the subject develops intolerable levels of such symptoms, the dosage may be reduced such that the adverse event is eliminated and no longer adverse or reduced to an acceptable level as judged by a treating physician.

Another consideration in determining the appropriate dose of compound for a patient is the desired concentration circulating in the blood plasma. In a particular embodiment, the concentration of compound in the blood is between 40-3,000 ng/mL over a 12 hour period from the time of administration. In another particular embodiment, the concentration of compound in the blood is between 75-2,000 ng/mL over a 12 hour period from the time of administration. In another particular embodiment, the concentration of compound in the blood is between 500-2,000 ng/mL over a 12 hour period from the time of administration. In a preferred embodiment, the concentration of compound in the blood is between 40-3,000 ng/mL over a 12 hour period from the time of administration, wherein the compound is a formula of I, I", II, or II" and is orally administered in an amount of about 50 mg, 100 mg, 150 mg, or 200 mg. In a preferred embodiment, the concentration of compound in the blood is between 40-3,000 ng/mL over a 12 hour period from the time of administration, wherein the compound is a formula of I and is orally administered in an amount of about 50 mg, 100 mg, 150 mg, or 200 mg. In a preferred embodiment, the concentration of compound in the blood is between 40-3,000 ng/mL over a 12 hour period from the time of administration, wherein the compound is a formula of II and is orally administered in an amount of about 50 mg, 100 mg, 150 mg, or 200 mg. In some of the foregoing embodiments, the maximum concentration in the blood plasma is achieved within two hours of administration.

In certain embodiments, the dosage of the compound of Formula I or II is selected to produce a plasma concentration of drug of about 10 nM or higher over a period of 8 to 12 hours, on average, and to provide a peak plasma concentration of about 500 nM or higher, preferably about 1000 nM or higher. In certain embodiments, the dosage of the compound of Formula I or II is selected to produce a plasma concentration of drug of about 100 nM or higher over a period of 8 to 12 hours, on average, and to provide a peak plasma concentration of about 500 nM or higher, preferably about 1000 nM or higher. In certain embodiments, the dosage of the compound of Formula I or II is selected to produce a plasma concentration of drug of about 200 nM or higher over a period of 8 to 12 hours, on average, and to provide a peak plasma concentration of about 500 nM or higher, preferably about 1000 nM or higher.

In certain embodiments, the dosage of the compound of formula I or II is selected to produce a plasma concentration wherein the trough concentration of the compound is in the range where a therapeutic effect, such as apoptosis of cancer cells, is observed. In certain embodiments, the dosage of the compound of formula I or II is selected to produce a trough plasma concentration at or higher than the $EC_{50}$ PI3Kδ isoform activation in blood plasma. In certain embodiments, the dosage of the compound of formula I or II is selected to produce an trough blood concentration above the $EC_{50}$ level for PI3Kδ activation and below the level for $EC_{50}$ PI3Kγ activation in a cell during a period of at least 12 hours from compound administration. For instance, if the $EC_{50}$ value for PI3K δ basophil activation is 65 nM and the $EC_{50}$ value for PI3K γ basophil activation is 1100 nM in whole blood plasma, then the dosage of the compound selected provides a trough plasma concentration of the compound between 60 nM and 1100 nM during a period of 8-12 hours from compound administration. Similarly, a dosage can be selected to produce an trough blood concentration above the $EC_{50}$ level for PI3Kδ basophil activation and below the $EC_{50}$ level for PI3K -α, -β or -γ basophil activation. The $EC_{50}$ values for the PI3K isoform activation or inhibition in vivo can be determined by a person having ordinary skill in the art. In alternative embodiments, the upper range of the trough concentration of the drug may exceed and is not limited by the $EC_{50}$ value of the PI3K -γ, -α, or -β isoform in blood plasma. Moreover, the blood concentration range of the drug is at a level which is therapeutically beneficial in treating the hematologic malignancy, while minimizing undesirable side effects.

For instance, while being delta-selective, the compounds can exhibit sufficient activity on p110γ to be clinically useful, i.e., to be effective on a cancer that relies upon p110γ for signaling, because a plasma level above the effective dosage for inhibition of p110γ can be achieved while still being selective relative to other isoforms, particularly the alpha isoform. Thus, in some embodiments, the dosage of the compound is selected to produce a blood concentration effective for selectively inhibiting p110δ and p110γ.

In some embodiments, the dosage of the compound provides a trough blood plasma concentration between 65 nM and 1100 nM during a period of 8 to 12 hours from compound administration. In some foregoing embodiments, the period is at least 12 hours from compound administration.

In a particular embodiment, the compound is administered in a therapeutically effective amount.

In a particular embodiment, the compound is administered at a dose of 20-500 mg/day. In a particular embodiment, the compound is administered at a dose of 50-250 mg/day.

In a particular embodiment, the compound is administered at a dose of 25 to 150 mg per dose, and two doses are administered per day (e.g., BID dosing with 25 to 150 mg doses). In a preferred embodiment, a subject is treated with 50 mg to 100 mg of a compound of formula A twice per day. In another preferred embodiment, a subject is treated with 50 mg to 150 mg of a compound of formula A twice per day.

In a particular embodiment, the method comprises administering to said patient an initial daily dose of 20-500 mg of the compound and increasing said dose by increments until clinical efficacy is achieved. Increments of about 25, 50, or 100 mg can be used to increase the dose. The dosage can be increased daily, every other day, twice per week, or once per week.

In a particular embodiment, the method comprises continuing to treat said patient by administering the same dose of the compound at which clinical efficacy is achieved or reducing said dose by increments to a level at which efficacy can be maintained.

In a particular embodiment, the method comprises administering to said patient an initial daily dose of 20-500 mg of the compound and increasing said dose to a total dosage of 50-400 mg per day over at least 6 days. Optionally, the dosage can be further increased to about 750 mg/day.

In a particular embodiment, the compound is administered at least twice daily.

In a particular embodiment, the compound is administered orally, intravenously or by inhalation. Preferably, the compound is administered orally. In some embodiments, it is administered orally at a dosage of about 50 mg BID or at a dosage of about 100 mg BID. In other embodiments, it is administered orally at a dosage of about 150 mg BID.

For the methods of the invention, any effective administration regimen regulating the timing and sequence of doses can be used. Doses of the agent preferably include pharmaceutical dosage units comprising an effective amount of the agent. As used herein, "effective amount" refers to an amount sufficient to modulate PI3Kδ expression or activity and/or derive a measurable change in a physiological parameter of the subject through administration of one or more of the pharmaceutical dosage units. "Effective amount" can also refer to the amount required to ameliorate a disease or disorder in a subject.

Suitable dosage ranges for the compounds of formula A vary according to these considerations, but in general, the compounds are administered in the range of 10.0 μg/kg-15 mg/kg of body weight; 1.0 μg/kg-10 mg/kg of body weight, or 0.5 mg/kg-5 mg/kg of body weight. For a typical 70-kg human subject, thus, the dosage range is from 700 μg-1050 mg; 70 μg-700 mg; or 35 mg-350 mg per dose, and two or more doses may be administered per day. Dosages may be higher when the compounds are administered orally or transdermally as compared to, for example, i.v. administration. The reduced toxicity of a compound of formula A, permits the therapeutic administration of relatively high doses. In some of the foregoing embodiments, oral administration of up to 750 mg/day of a compound of the invention is suitable. In some of the foregoing embodiments, a compound of formula A is administered at a dose of 50 mg BID. In some of the foregoing embodiments, a compound of formula A is administered at a dose of 100 mg BID. In some of the foregoing embodiments, a compound of formula A is administered at a dosage of 150 mg BID. In some of the foregoing embodiments, a compound of formula A is administered at a dose of 200 mg BID. In some of the foregoing embodiments, a compound of formula A is administered at a dose of 350 mg BID. In specific embodiments, for treatment of leukemias, lymphomas and multiple myeloma, a dosage of about 50-350 mg per dose, administered orally once or preferably twice per day, is often suitable.

In some of the foregoing embodiments, oral administration of up to 750 mg/day of compound I" or II" is suitable. In some of the foregoing embodiments, a compound of formula I" or II" is administered at a dose of 50 mg BID. In some of the foregoing embodiments, a compound of formula I" or II" is administered at a dose of 100 mg BID. In some of the foregoing embodiments, a compound of formula I" or II" is administered at a dose of 150 mg BID. In some of the foregoing embodiments, a compound of formula I" or II" is administered at a dose of 200 mg BID. In some of the foregoing embodiments, a compound of formula I" or II" is administered at a dose of 350 mg BID. In some of the foregoing embodiments, for treatment of leukemias, lymphomas and multiple myeloma, a dosage of about 50-350 mg per dose of a compound of formula I" or II", administered orally once or preferably twice per day, is often suitable.

The compounds may be administered as a single bolus dose, a dose over time, as in i.v. or transdermal administration, or in multiple dosages.

Dosing may be continued for at least seven days. In some embodiments, daily dosing is continued for about 28 days. In some embodiments, dosing is continued for about 28 days and is then discontinued for at least 7 days. In some embodiments, a complete cycle is continuous daily dosing for 28 days. Evaluation of a clinical response in the patient can be measured after each cycle. The clinical results can be used to make a decision to increase, decrease, discontinue or maintain the dosage.

Depending on the route of administration, a suitable dose can be calculated according to body weight, body surface area, or organ size. The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the compound of Formula A and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the compound. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Subjects that will respond favorably to the method of the invention include medical and veterinary subjects generally, including human patients. Among other subjects for whom the methods of the invention is useful are cats, dogs, large animals, avians such as chickens, and the like. In general, any subject who would benefit from a compound of formula A is appropriate for administration of the invention method. In some foregoing embodiments, the patient has a cytogenetic characteristic of del(17p) or del(11q). In some foregoing, embodiments, the patient has a lymphadenopathy. In some foregoing embodiments, the use of compound I, I", II, or II" reduces the size of a lymphadenopathy in a patient. In some foregoing embodiments, the use of compound I, I", II, or II" reduces the size of a lymphadenopathy after one cycle of treatment. In some foregoing embodiments, the use of compound I, I", II, or II" reduces the size of a lymphadenopathy by at least 10% after one cycle of treatment. In some foregoing embodiments, the use of compound I, I", II, or II" reduces the size of a lymphadenopathy by at least 25% after one cycle of treatment. In some foregoing embodiments, the use of compound I, I", II, or II" reduces the size of a lymphadenopathy by at least 30% after one cycle of treatment. In some foregoing embodiments, the use of compound I, I", II, or II" reduces the size of a lymphadenopathy by at least 40% after one cycle of treatment. In some foregoing embodiments, the use of compound I, I", II, or II" reduces the size of a lymphadenopathy by at least 50% after one cycle of treatment. In some foregoing embodiments, the use of compound I, I", II, or II" reduces the size of a lymphadenopathy by at least 75% after one cycle of treatment.

In one aspect, the invention provides a method of treating a condition, comprising administering a compound of formula I, II or a pharmaceutically acceptable salt thereof and one or more therapeutic agents to a subject in need of such treatment, wherein the condition is a cancer or an autoimmune condition. In preferred embodiments, the therapeutic agent is a proteasome inhibitor. In more specific embodiments, the therapeutic agent is bortezomib. In some of the foregoing embodiments, the condition is a hematologic malignancy. In preferred embodiments, the condition is selected from the group consisting of multiple myeloma, acute lymphocytic leukemia, acute myeloid leukemia, chronic lymphocytic leukemia, B-cell lymphoma, diffuse large B-cell lymphoma, B-cell ALL, T-cell ALL and Hodgkin's lymphoma. In preferred embodiments, the compound is substantially comprised of the S-enantiomer. In specific embodiments, the compound comprises at least 95% of the S-enantiomer. In some of the foregoing embodiments, the administration of said compound and therapeutic agent provides a synergistic benefit superior to results obtained without the combination of the compound and therapeutic agent.

The following examples are offered to illustrate but not to limit the invention. In the examples below, references to the 'compound of formula I' or 'compound I' refer to the S-enantiomer shown here, and samples used for these Examples exhibited a 98.2% ee as measured by chiral HPLC methods:

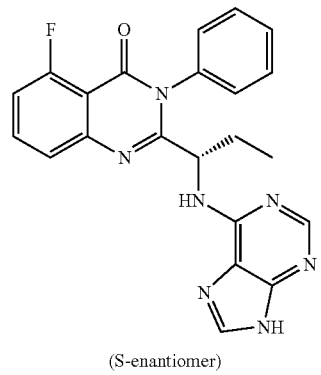 [SMILES: CC[C@H](Nc1ncnc2[nH]cnc12)c1nc2cccc(F)c2c(=O)n1-c1ccccc1]

(S-enantiomer)

In addition, an analysis of this compound reveals the following characteristics of the material:

| Test | Test Result |
|---|---|
| Appearance | Slightly off-white powder |
| 1H-NMR | Spectrum conforms to the reference |

37
-continued

| Test | Test Result |
|---|---|
| HPLC Assay | 98.1% (Anhydrous, solvent-free basis) |
| Chiral Purity (HPLC) | 98.2% ee |

| Test | Test Result |
|---|---|
| Residual on Ignition | 0.11% |
| Infrared Spectroscopy (FTIR) | Spectrum in agreement with the reference |
| 13C-NMR | Spectrum conforms to the reference |
| Particle Size Analysis | Median diameter: 11.3 μm |
| Water (Coulometric Karl Fischer) | 0.56% |

| | | Test Result | |
|---|---|---|---|
| Property or Test | | Expected | Found |
| Elemental Analysis | %C | 63.3 | 63.5 |
| % C, H, F, N | %H | 4.4 | 4.4 |
| | %N | 23.5 | 23.1 |
| | %F | 4.5 | 4.5 |

EXAMPLE 1

Inhibition of Cell Growth in MM Cells

This example demonstrates the compound of formula I inhibits the cellular growth stimulatory effects of cytokines (IGF-1 and IL-6) in multiple myeloma (MM) cells. LB cells (Myelomonocytic myeloma cell line) were cultured for 48 h with control media; with the compound of formula I, in the presence or absence of either IL-6 or IGF-1. The inhibitory effect of the compound of formula I on MM cell growth was assessed by measuring 3-(4,5-dimethylthiazol-2-yl)-2,5-diphenyl tetrasodium bromide (MTT; Chemicon International) dye absorbance. Cells were pulsed with 10 μL of 5 mg/mL MTT to each well for the last 4 hours of 48-hour cultures, followed by 100 μL isopropanol containing 0.04 N HCl. Absorbance was measured at 570/630 nm using a spectrophotometer (Molecular Devices). A summary of the results is shown in FIG. 1. Exposure of 0.625 μM-2.5 μM of Compound I inhibits MM cell growth even in the presence of cell growth stimulatory cytokines.

EXAMPLE 2

Effect of BMSC on Cytotoxicity

Figure 2:
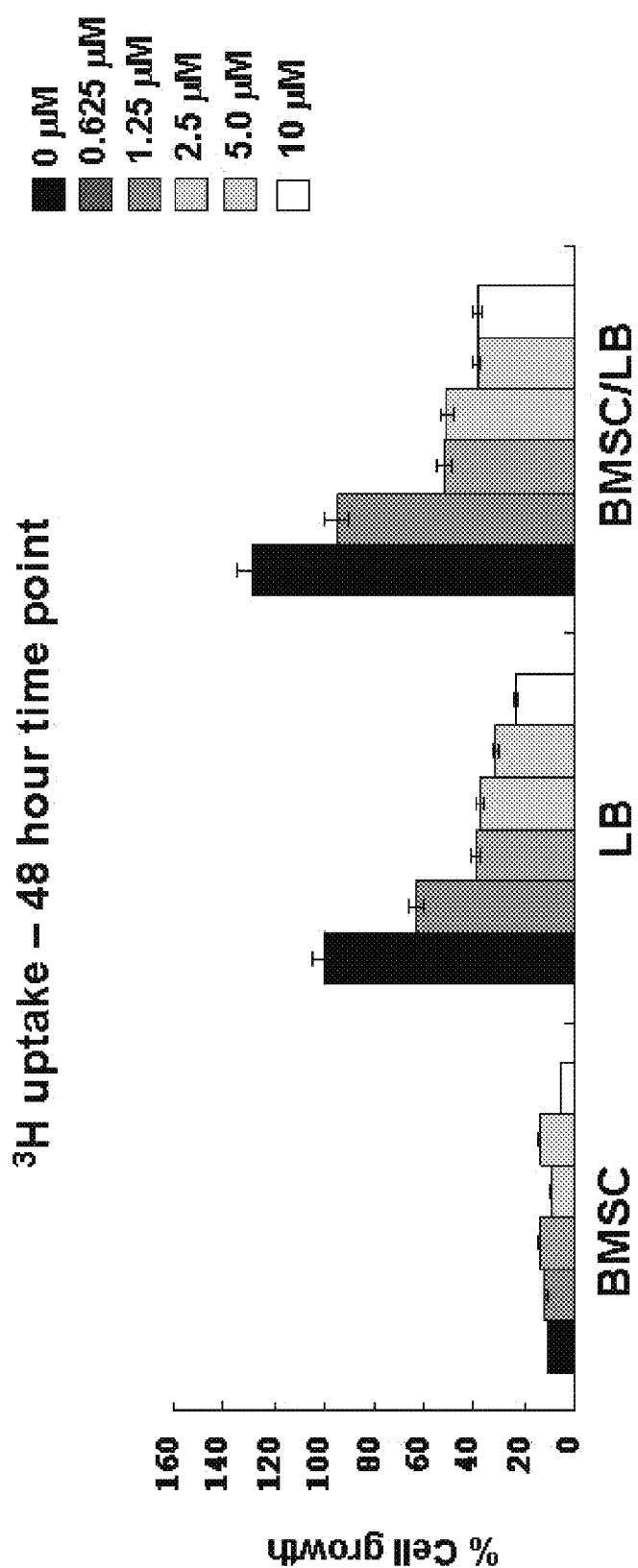
FIG. 2 shows a graphical summary of cell growth of multiple myeloma (MM) cells as a function of varying concentrations of compound I and the presence or absence of bone marrow stromal cells (BMSC) after 48 hours.

This example demonstrates Bone Marrow Stromal Cells (BMSCs) do not protect against compound I-induced LB cell cytotoxicity. LB cells were cultured with control media, and with the compound of formula I for 48 hours, in the presence or absence of BMSCs. Cell proliferation was assessed using [$^3$H]'-thymidine uptake assay. All data represent mean (±SD) of triplicate experiment. A summary of the results is shown in FIG. 2. LB cell growth is reduced after exposure to 0.625 μM-10 μM of compound I even in the presence of BMSC.

EXAMPLE 3

Effect of Compound on Apoptosis of CLL Cells

This example demonstrates the compound of formula I induces apoptosis in patient chronic lymphocytic leukemia (CLL) cells. Peripheral blood was obtained from patients with B-CLL through the CLL Research Consortium from Ohio State University. Primary CD19-positive cells were isolated using Rosette-Sep (StemCell Technologies). Cells were maintained in RPMI 1640 (Invitrogen) supplemented with 10% heat-inactivated fetal bovine serum, 2 mmol/L L-glutamine, and penicillin (100 units/mL)/streptomycin (100 μg/mL; Invitrogen) at 37° C., 5% $CO_2$, and high humidity. After incubation with the compound of formula I or medium for 96 hours, 5×10$^5$ cells were washed with PBS and then resuspended in binding buffer (10 mmol/L HEPES/NaOH, pH 7.4, 150 mmol/L NaCl 5 mmol/L KCl, 1 mmol/L $MgCl_2$, 1.8 mmol/L $CaCl_2$) containing 2 μL of Annexin V-FITC stock (BioWhittaker, Inc) and 10 μL of 20 μg/mL PI (Sigma). After incubation for 10 minutes at room temperature in a light-protected area, the specimens were quantified by flow cytometry on a FACScan™ (Becton Dickinson).

Figures 3, 4:
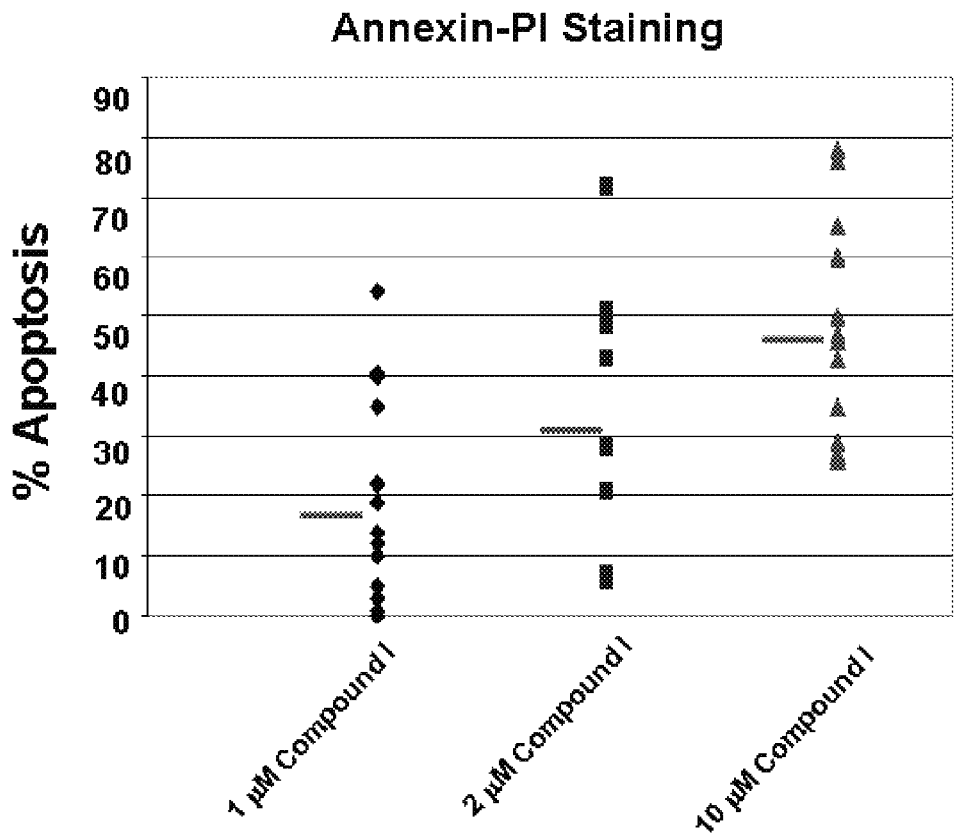
FIG. 3 shows a graphical summary of apoptosis of Chronic Lymphocytic Leukemia (CLL) cells as a function of varying concentrations of compound of formula I.
FIG. 4 shows a summary chart of the effect of compound I on cell viability, reduction in Akt (Ser473) phosphorylation, and caspase 3 activation in several different Acute Lymphoblastic Leukemia (ALL) cell lines.

Treatment of CLL patient cells with compound I results in apoptosis and the result appears to be dose-dependent, as seen in FIG. 3.

Figure 19:
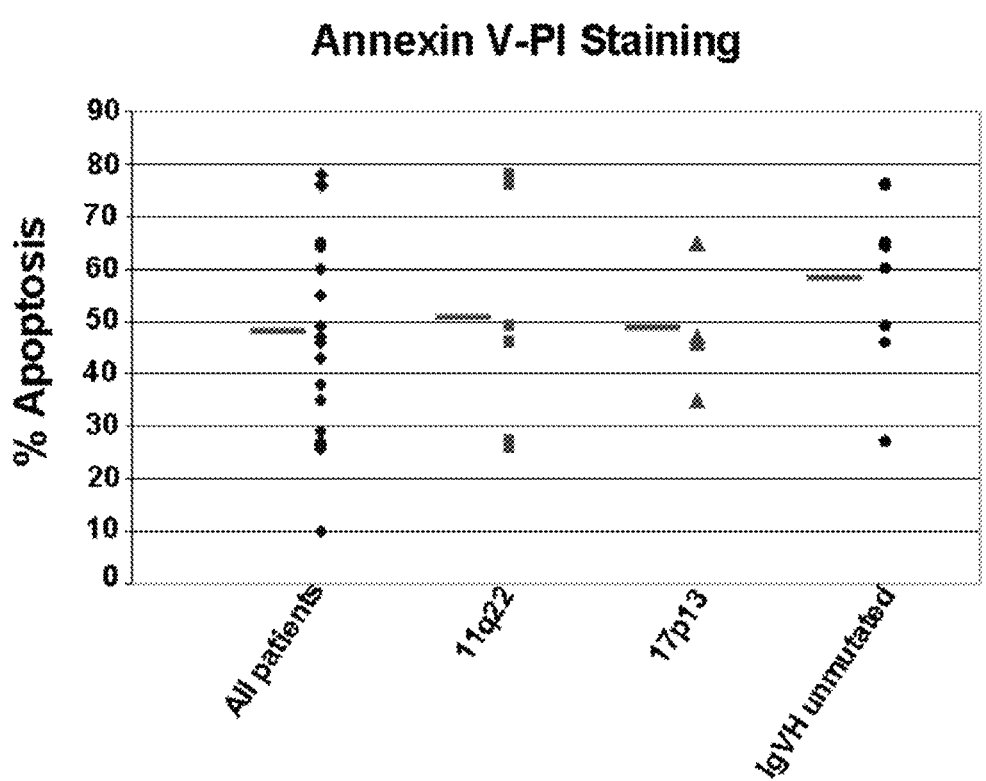
FIG. 19 shows increased apoptosis of Chronic Lymphocytic Leukemia (CLL) cells from poor prognosis patients caused by exposure to compound I, demonstrating that compound I is effective in drug resistant patients.
Figure 20:
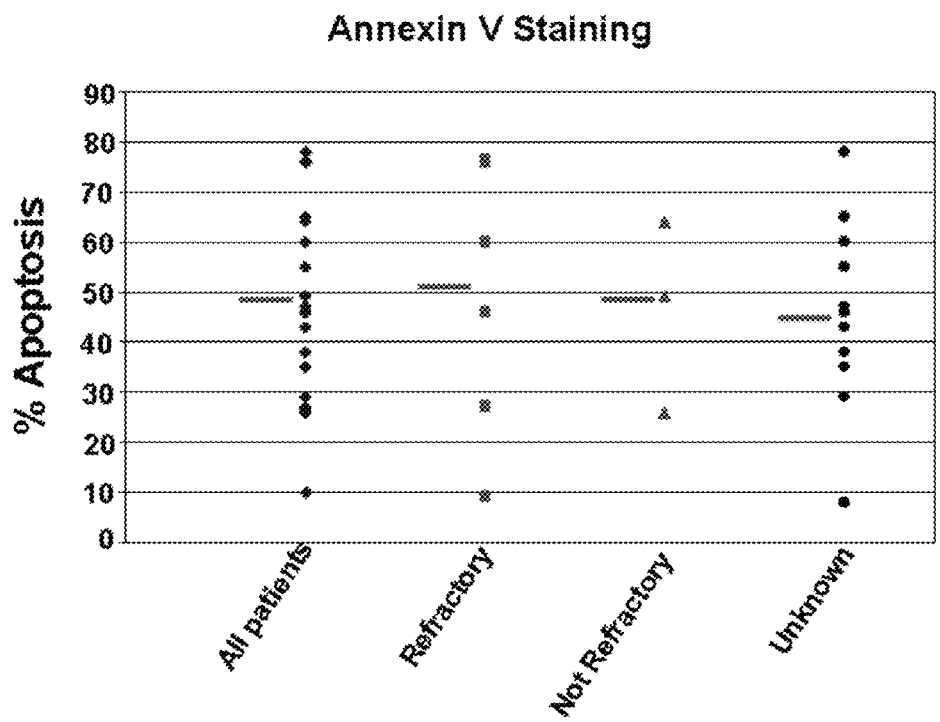
FIG. 20 shows increased apoptosis of Chronic Lymphocytic Leukemia (CLL) cells from refractory/relapsed patients caused by exposure to the compound of formula I.

Compound I induced apoptosis was seen in CLL cells from poor prognosis patients, as the data indicates in FIG. 19.

Compound I induced apoptosis was also seen to be effective in CLL cells from refractory/relapsed patients as shown in FIG. 20.

EXAMPLE 4

Effect of Compound in ALL Cell Lines

This example demonstrates the compound of formula I results in a reduction of Akt phosphorylation and a decrease in cellular proliferation accompanied by cell death in both T-ALL and B-ALL (Acute Lymphoblastic Leukemia) leukemic cell lines. Viability assays of cell lines were performed using the AlamarBlue assay (Invitrogen). Cells (1×10$^6$ per well) in a volume of 100 μL were placed in a 96-well flat-bottom plate and the compound of formula I (100 μL per well at 2× final concentration) or medium alone was added to the plates. All were performed in quadruplicate. Cells were incubated for fixed times (48 hours). After the incubation, 10 μL AlamarBlue® was added to each well. Cells were incubated for 4 hours and the optical density at 530-560 nm was obtained using a SpectraMax® M5 plate reader 2001. Cell viability was expressed as a percentage of absorption between treated cells/control sample. These results are summarized in the table shown in FIG. 4. Exposure to compound I result in substantial reduction in cellular viability in a variety ALL cell lines as well as reduction in Akt phosphorylation.

EXAMPLE 5

Effect of Compound on ALL Cell Cycle

Figure 5:
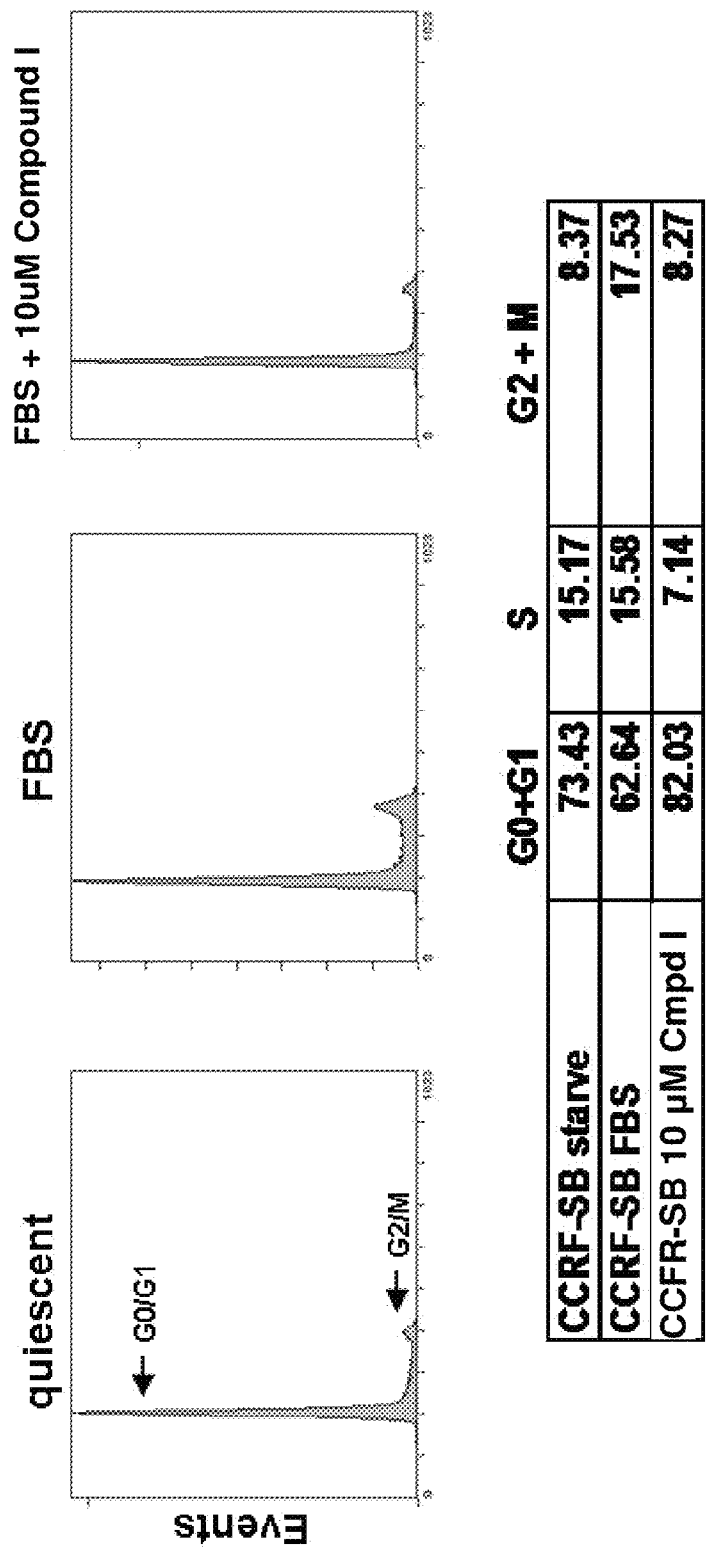
FIG. 5 shows a summary of the effect of compound I on the cell cycle of acute lymphoblastic leukemia (ALL) cell lines.

This example demonstrates treatment of the acute lymphoblastic leukemia (ALL) cell line CCRF-SB with the compound of formula I results in G0/G1 cell cycle arrest. Representative fluorescence-activated cell sorting (FACS) analysis of propidium iodide-stained CCRF-SB cells under normal growth conditions, and growth in the presence of the compound of formula I. The average percentage of cells in $G_0$-$G_1$, S, and $G_2$-M phases is calculated in the table below the histographs. Results are shown in FIG. 5.

EXAMPLE 6

Inhibition of Proliferation of Breast Cancer Cells

This example demonstrates the compound of formula I inhibits proliferation of breast cancer cell lines. T47D and HS-578T cell lines were grown in the presence of serum plus the indicated concentrations of the compound of formula I. Proliferation was measured in triplicate wells by Alamar-Blue® assay (Invitrogen) 96-well plates. Results of proliferation assays are expressed as the mean cellular percentage values and shown in FIG. 6.

EXAMPLE 7

Inhibition of Proliferation of Ovarian Cancer Cell Lines

Figure 7:
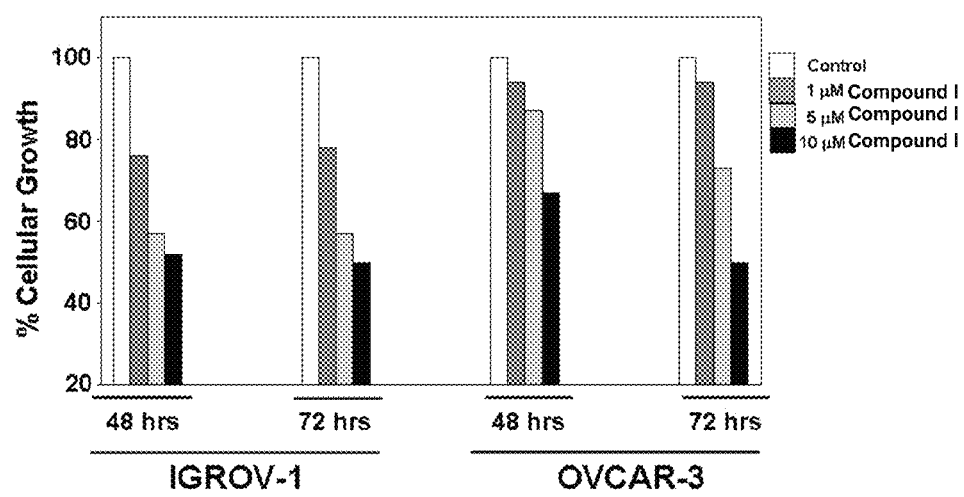
FIG. 7 shows a graphical summary of the effect of varying concentrations of compound I on cellular growth of ovarian IGROV-1 and OVCAR-3 cell lines at 48 hrs and 72 hrs.

This example demonstrates the compound of formula I inhibits proliferation of ovarian cancer cell lines. IGROV-1 and OVCAR-3 cell lines were grown in the presence of serum plus the indicated concentrations of the compound of formula I. Proliferation was measured in triplicate wells by AlamarBlue assay (Invitrogen) 96-well plates. Results of proliferation assays are expressed as the mean cellular percentage values and are shown in FIG. 7.

EXAMPLE 8

Reduction of Akt Phosphorylation

This example demonstrates the compound of formula I reduces constitutive Akt phosphorylation in hematopoietic tumor cell lines that exhibited constitutive Akt phosphorylation. A large panel of leukemia and lymphoma cell lines was assessed for constitutive Akt phosphorylation. These cell lines represent B-lymphoma, T-lymphoma, ALL, Malignant histiocytosis, DLBCL and AML. Cell lines that demonstrated serum independent Akt phosphorylation were treated with the compound of formula I for 2 hours. Thereafter, cell were lysed, size-fractioned and immunoblotted with antibodies directed against phospho-Akt(Ser473). Results are shown in FIG. 8. Reduction in Akt(Ser473) was achieved for all cell lines after exposure to compound I.

EXAMPLE 9

Compound I Effective in DLBCL

Figure 26:
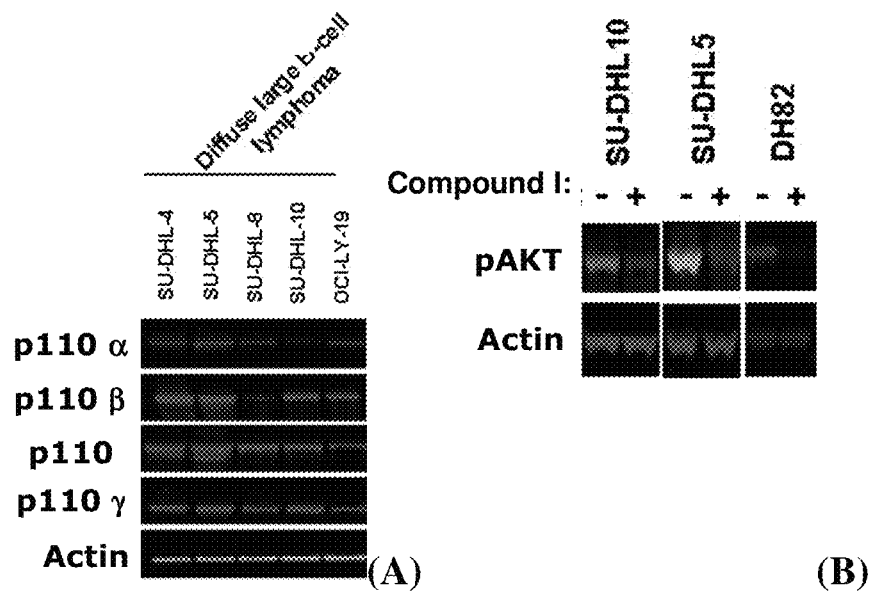
FIG. 26 B shows an SDS-PAGE image of pAkt in DLBCL cell lines in the presence or absence of compound I.

This example provides evidence that compound I blocks PI3K signaling and induces apoptosis in diffuse large B-cell lymphoma cells. P110δ is expressed in DLBCL cell lines as shown in FIG. 26A. FIG. 26B shows that exposure to compound I reduces pAKT levels in several DLBCL cell lines.

EXAMPLE 10

Inducement of Apoptosis in Breast Cancer Cells

This example demonstrates the compound of formula I induces apoptosis in breast cancer cell lines. HS-578T, T47D, and MCF7 cells were treated with the compound of formula I or corresponding DMSO concentrations for 24 h. The percentage of apoptotic cells was determined by Annexin V-FITC/7AAD staining. Bottom left, viable cells (Annexin V-FITC/PI negative); bottom right, early apoptotic cells (Annexin V-FITC positive only); top right, mid-late apoptotic cells (Annexin V-FITC/7AAD double-positive); and top left, late apoptotic/necrotic (7AAD positive only). Percentages of cells in each quadrant are indicated except for the bottom left quadrant (viable cells). One experiment representative of three different experiments that gave similar results is shown in FIG. 10.

EXAMPLE 11

Steady State Blood Levels on Day 7 in Healthy Volunteers

Figure 11:
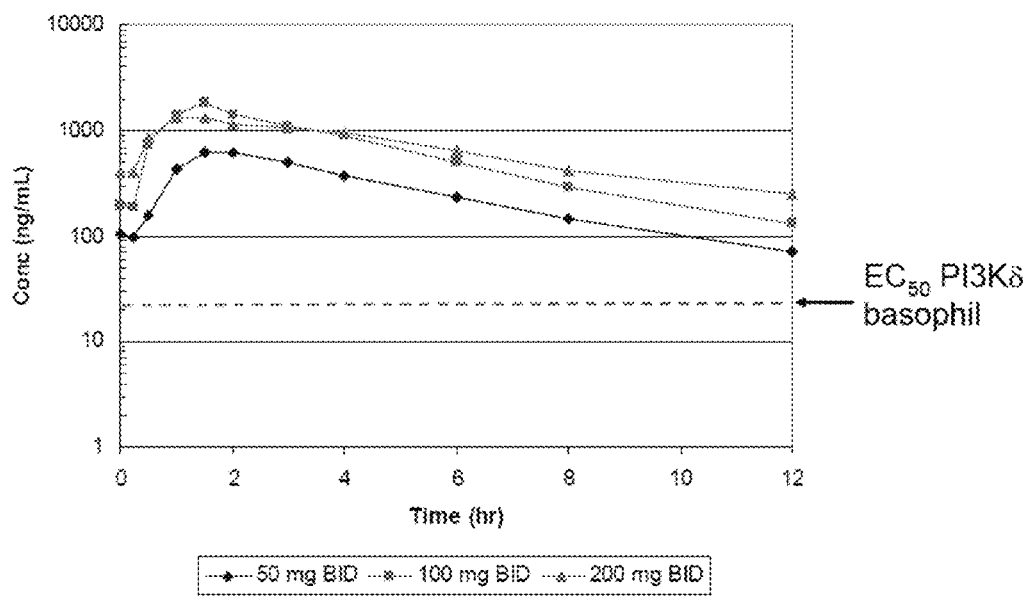
FIG. 11 shows the concentration of compound I in the blood of a healthy human subject over 12 hours after oral administration of 50, 100 and 200 mg doses of said compound.

This example provides data relating to the concentration of the compound of formula I in the blood of a healthy human subject on day 7. The concentration was monitored over a period of 12 hours, after oral administration of 50, 100, or 200 mg BID of the compound of formula I on day 7 of the study. FIG. 11 follows the plasma concentration of the drug over a period of 12 hours from administration. The maximum concentration of drug is achieved within two hours for all doses. Administration of 50, 100 or 200 mg BID of said compound results in a concentration level that exceeds the PI3Kδ $EC_{50}$ concentration in basophil for at least 12 hours.

Figure 24:
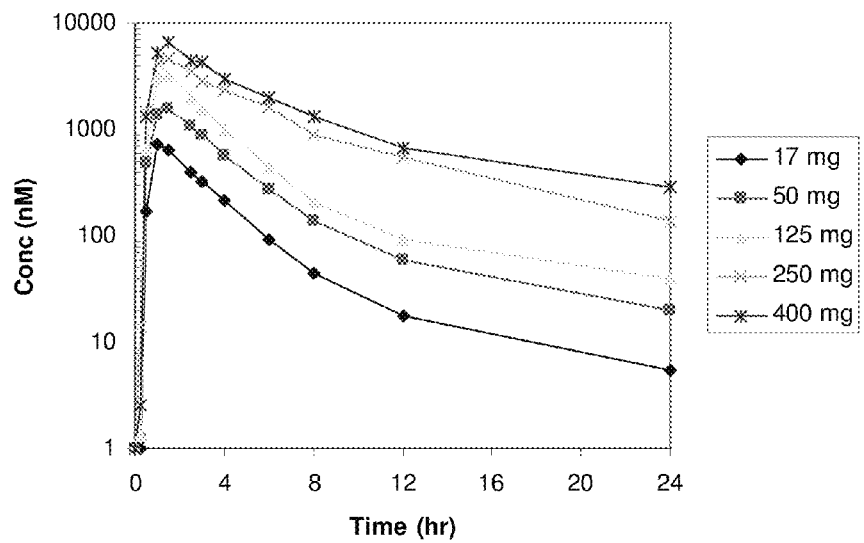
FIG. 24 shows pharmacokinetic data of (A) single dose administration of compound I at different dose amounts in healthy volunteers, and (B) a pharmacokinetic profile that maintains an effective dosage over a 12 hour period.
Figure 24:
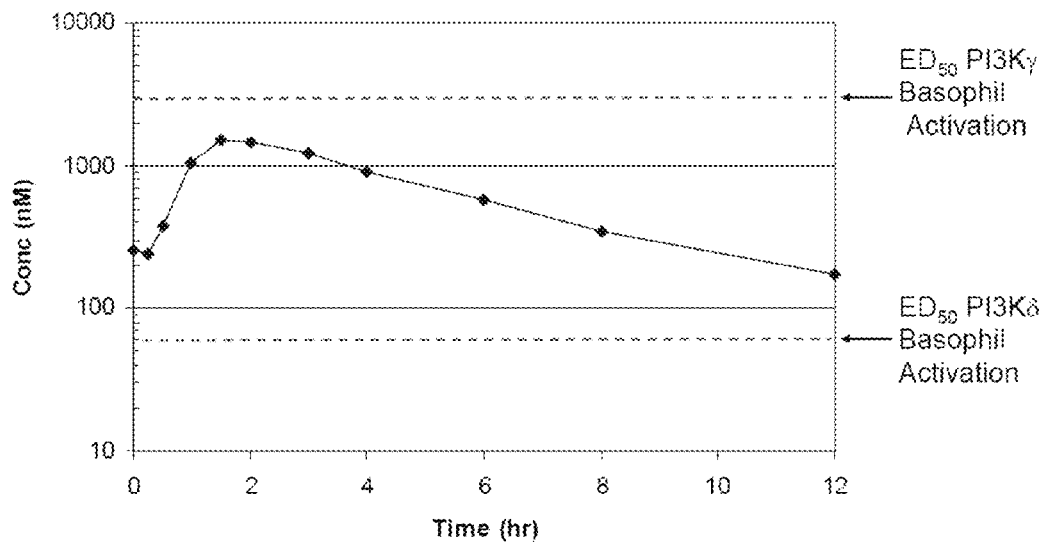

In addition, single dose studies wherein 17-400 mg of the compound of formula I was administered in healthy volunteers was carried out. Concentration of the compound in the blood was measured over 24 hours from administration and results are shown in FIG. 24A. At about 6 hours, the concentration of compound I in the blood for all administered doses is at least about 100 nM. At about 12 hours, the concentration of compound I in the blood for doses 50 mg and higher is over 50 nM. The maximum concentration of compound I in the blood is achieved within 2 hours of administration.

In another experiment, the mean compound I concentration was measured on the 7th day of 50 mg BID dosing in healthy volunteers (N=6). The mean trough concentration was higher than the EC50 for PI3Kδ and the mean peak concentration was lower than the EC50 for PI3Kγ as determined in the whole blood basophil activation assay, FIG. 24B. This example demonstrates the concentration range of compound I administered at 50 mg BID is at a level that is above the $ED_{50}$ PI3Kδ basophil activation level but lower than the minimum $ED_{50}$ PI3Kγ basophil level activation level in whole blood for at least 12 hours.

Table 1, below, provides an overview of the subjects in the study, wherein either a singe dose (SD) or multiple dose (MD) of the compound of formula I is administered to a subject at varying amounts. The "n" values refer to the number of subjects in each group.

TABLE 1

| Cohort | Regimen | Compound I | Placebo |
| --- | --- | --- | --- |
| 1 (n = 8) | SD | 17 mg (n = 6) | Placebo (n = 2) |
| 2 (n = 8) | SD | 50 mg (n = 6) | Placebo (n = 2) |
| 3 (n = 8) | SD | 125 mg (n = 6) | Placebo (n = 2) |
| 4 (n = 8) | SD | 250 mg (n = 6) | Placebo (n = 2) |
| 5 (n = 8) | SD | 400 mg (n = 6) | Placebo (n = 2) |

TABLE 1-continued

| Cohort | Regimen | Compound I | Placebo |
|---|---|---|---|
| 6 (n = 8) | MD | 50 mg BID × 7 d (n = 6) | Placebo BID × 7 d (n = 2) |
| 7 (n = 8) | MD | 100 mg BID × 7 d (n = 6) | Placebo BID × 7 d (n = 2) |
| 8 (n = 8) | MD | 200 mg BID × 7 d (n = 6) | Placebo BID × 7 d (n = 2) |

EXAMPLE 12

Effect on Lesions in a Patient with Mantle Cell Lymphoma

This example provides data relating to the area of lesions of a patient with mantle cell lymphoma after 1 cycle of treatment (28 days) with the compound of formula I. The area of 6 lesions was measured prior to treatment and after a cycle of treatment. The response to 28 days of oral administration of 50 mg BID of the compound of formula I, results in a decrease of lesion area compared to area prior to treatment and represents a 44% decrease in tumor burden. The results are summarized in a bar graph found in FIG. 12.

EXAMPLE 13

Response of a Patient with CLL to Treatment

This example provides data relating to the concentration of absolute lymphocyte count (ALC) in the blood of a patient with CLL after 1 cycle (28 days) of treatment with oral administration of the compound of formula I. The blood ALC concentration was measured over a period of 4 weeks after completion of one cycle of treatment. A 55% decrease in lymphocytosis and a 38% decrease in lymphadenopathy as a result of treatment were observed. A marked decrease in ALC concentration is observed between week 1 and week 2, FIG. 13.

EXAMPLE 14

Comparison of Lymphoma Patient to Healthy Volunteer

This example provides data comparing the concentration of the compound of formula I in a lymphoma patient to normal healthy volunteers. On the 28$^{th}$ day of oral administration of 50 mg BID of compound in a patient with mantle cell lymphoma, the concentration of the compound in the blood was measured over a period of 6 hours after administration. The concentration of 50 and 100 mg oral administration in normal healthy volunteers on day 7 of administration was also observed. The results are summarized in FIG. 14. Thus, the compound does not build up excessively over the course of a cycle of treatment, nor does the patient become tolerant by increased metabolism over the course of the treatment cycle.

EXAMPLE 15

Activity of Compound I in Various Kinases

This example shows the $IC_{50}$ profile of compound I across classes of kinases as summarized in Table 2. While especially active on p110δ, Compound I was also active on p110γ and even active enough to be therapeutically useful at non-toxic doses against p110β, due to the demonstrated high NOAEL level of the compound; while exhibiting little activity on Class II-V phosphoinositide kinases. Thus while being delta-selective, the compounds can exhibit sufficient activity on p110γ to be clinically useful, i.e., to be effective on a cancer that relies upon p110γ for signaling, because a plasma level above the effective dosage for inhibition of p110γ can be achieved while still being selective relative to other isoforms, particularly the alpha isoform.

TABLE 2

| | Class I PI3Ks, $IC_{50}$ (nM) | | | | Class II PI3K, $IC_{50}$ (nM) | Class III PI3K, $IC_{50}$ (nM) | Class IV PI3K, $IC_{50}$ (nM) | | Other Phosphoinositide kinases | |
|---|---|---|---|---|---|---|---|---|---|---|
| Compound | p110α | p110β | p110δ | p110γ | CIIbeta | hVPS34 | DNA-PK | mTOR | PIP5Kα | PIP5Kβ |
| I | 435 | 128 | 1 | 14 | >10$^3$ | 978 | 6,729 | >10$^3$ | >10$^3$ | >10$^3$ |
| NVP-BEZ-235 Novartis | 19 | 293 | 63 | 267 | 3 | 6 | 1 | 2 | ND* | ND |

InvitroGen Adapta assay
*ND = not determined

EXAMPLE 16

No Off-Target Activity of Compound I in Kinome-Wide Protein Kinase Screen

This example demonstrates that compound I has little or no off target activity in a kinome-wide protein kinase screen. Using Ambit KINOMEscan™ a genome wide screen of over 350 protein kinases failed to detect any activity at 10 μM. Examples of some kinases in the screen are shown below in Table 3.

TABLE 3

| Examples of Relevant Kinases in Screen | | | | |
|---|---|---|---|---|
| ABL | FGFR1 | JAK1 | P38MAPK | S6K |
| AKT | VEGFR1 | JAK2 | PDGFR | SLK |
| ALK | FLT3 | JNK1 | PIM | SRC |
| BLK | FRK | KIT | PKA | SYK |
| BRAF | FYN | LCK | PKC | TAK |
| BTK | HCK | LYN | PLK | TIE |
| CDK | HER2 | MAPK | RAF | TRK |
| CSF1R | ICK | MEK | RET | TYK |
| EGFR | IGF1-R | MET | ROCK | YES |
| EPH | ITK | MLK | ROS | ZAP70 |

EXAMPLE 17

Selectivity of Compound I for p110δ

This example demonstrates that compound I is selective for p110δ as measured in isoform specific cell-based assays.

Swiss-3T3 fibroblasts and RAW-264 were seeded on a 96-well tissue culture plate and allowed to reach at least 90% confluency. Cells were starved and treated with either vehicle or serial dilutions of compound I for 2 hrs and stimulated with PDGF or C5a respectively. Akt phosphorylation and total AKT was detected by ELISA. Purified B-cells were treated with either vehicle or serial dilutions of compound I for 30 minutes at room temperature before the addition of purified goat anti-human IgM. Results are expressed as relative [$^3$H] thymidine incorporation induced by IgM crosslinking.

TABLE 4

| PI3Kα $EC_{50}$ (nM) | PI3Kδ $EC_{50}$ (nM) | PI3Kγ $EC_{50}$ (nM) |
|---|---|---|
| Fibroblast Cell Line PDGF induced pAKT | Primary B Cell BCR mediated proliferaton | Monocyte Cell Line C5a induced pAKT |
| >20,000 | 6 | 3,894 |
| (n = 12) | (n = 6) | (n = 11) |

EXAMPLE 18

Expression of p110δ in Leukemia and Lymphoma Cell Lines

This example demonstrates that PI3K p110δ is highly expressed in a broad range of leukemia and lymphoma cell lines.

PI3K p110δ promotes proliferation and survival in a wide range of leukemia and lymphoma cell lines. Among the cell types investigated are MCL, DLBCL, AML, ALL, and CML.

Figure 15:
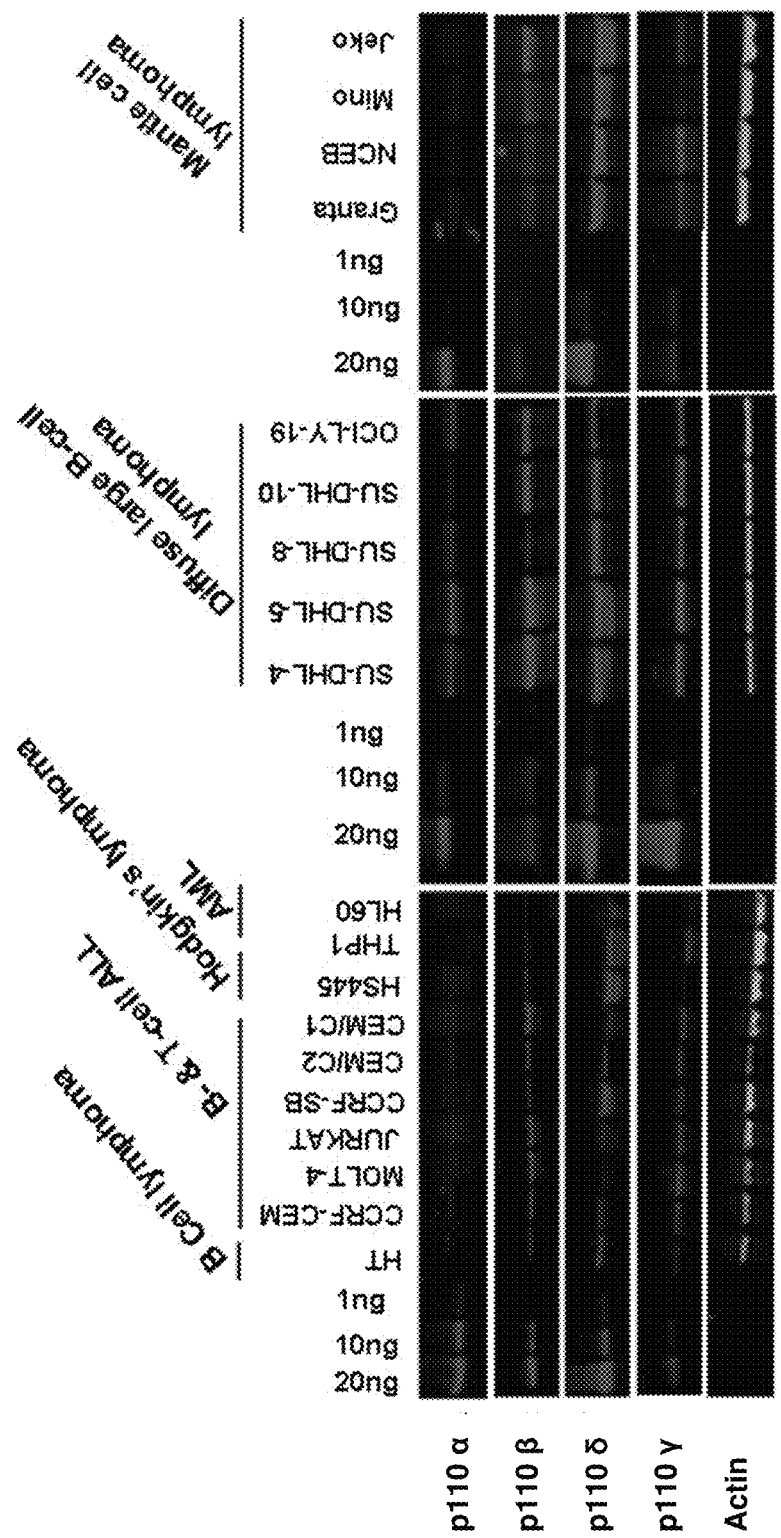
FIG. 15 shows PI3K isoform expression in a panel of lymphoma and leukemia cell lines.
Figure 16:
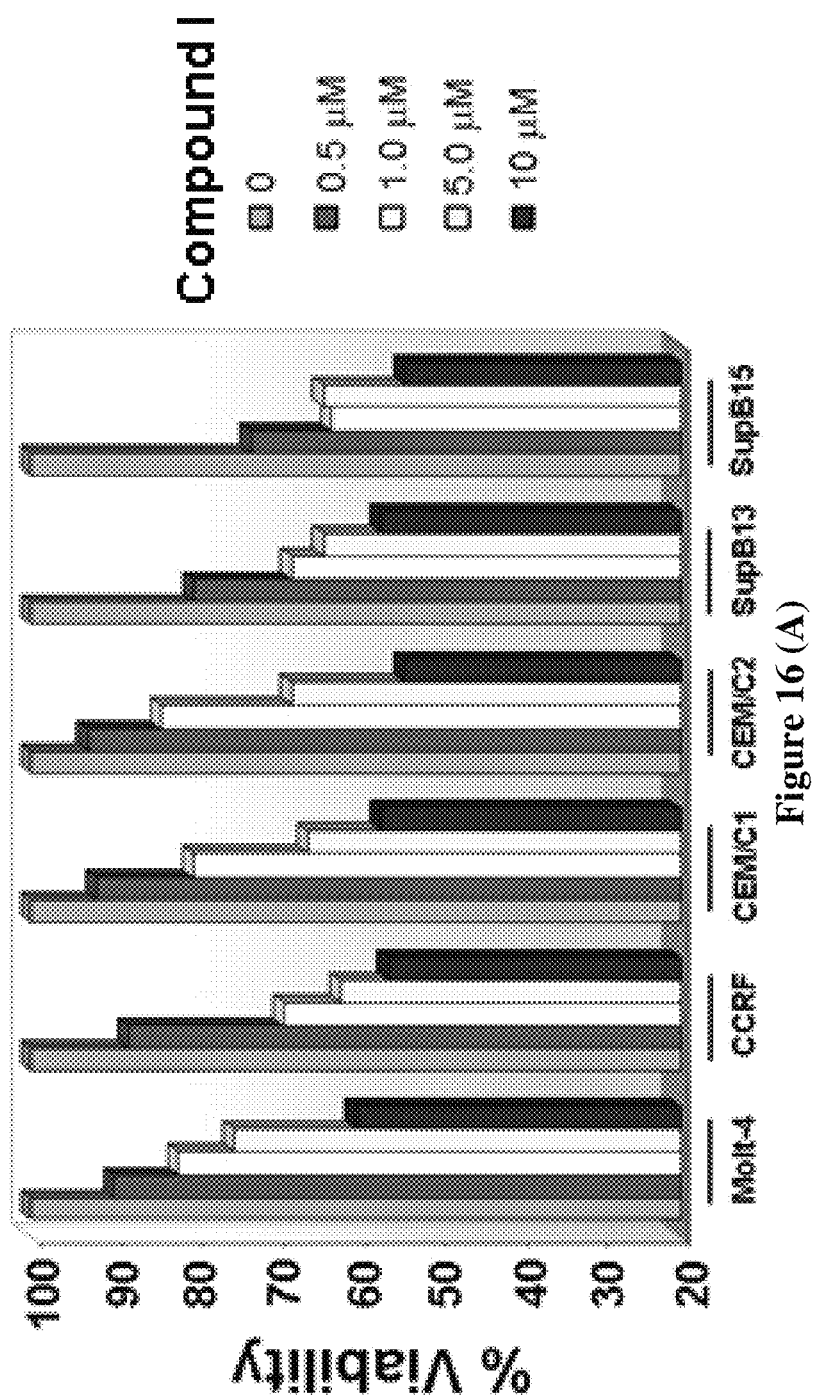
FIG. 16A shows cell viability and apoptosis data in leukemia cell lines exposed to Compound I.
In FIG. 16B the Annexin staining indicates an increase in apoptosis in the treated cells.
Figure 16:
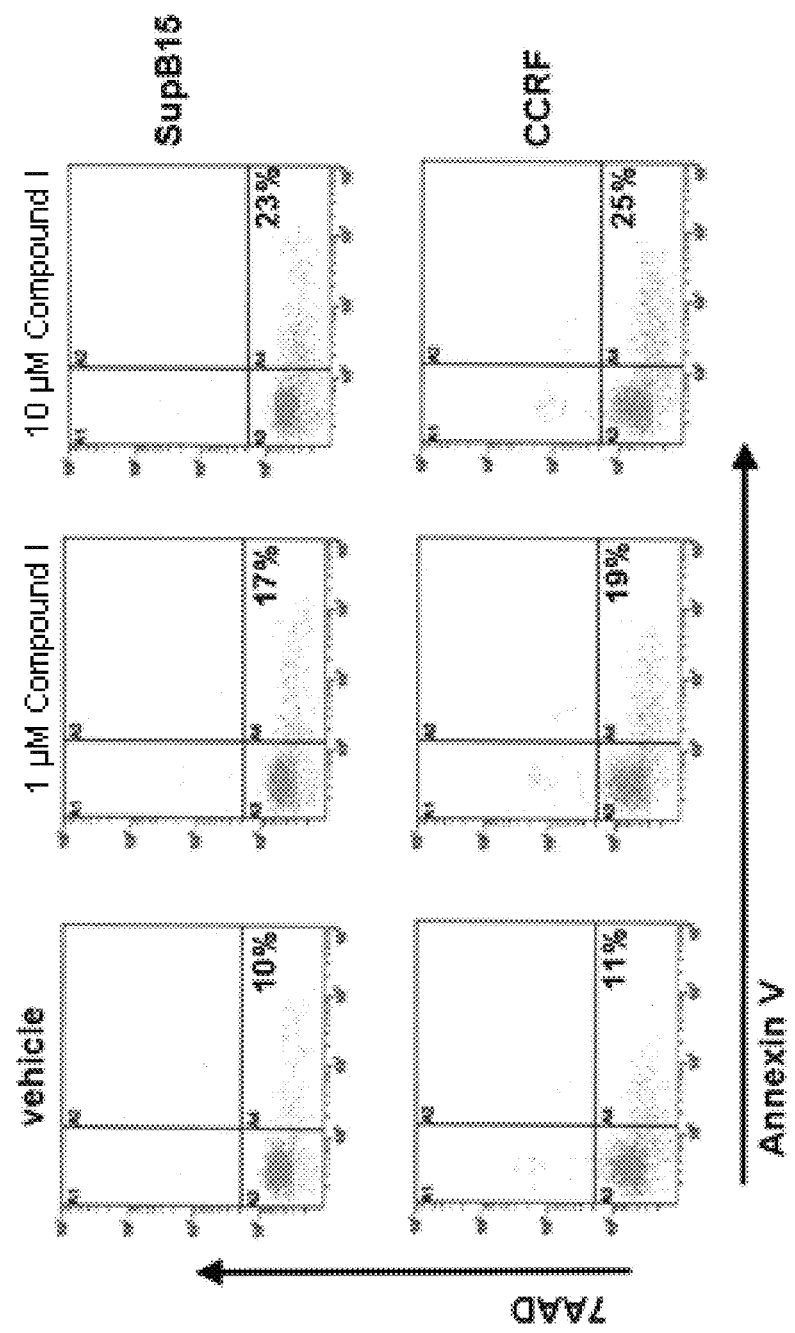
Figure 17:
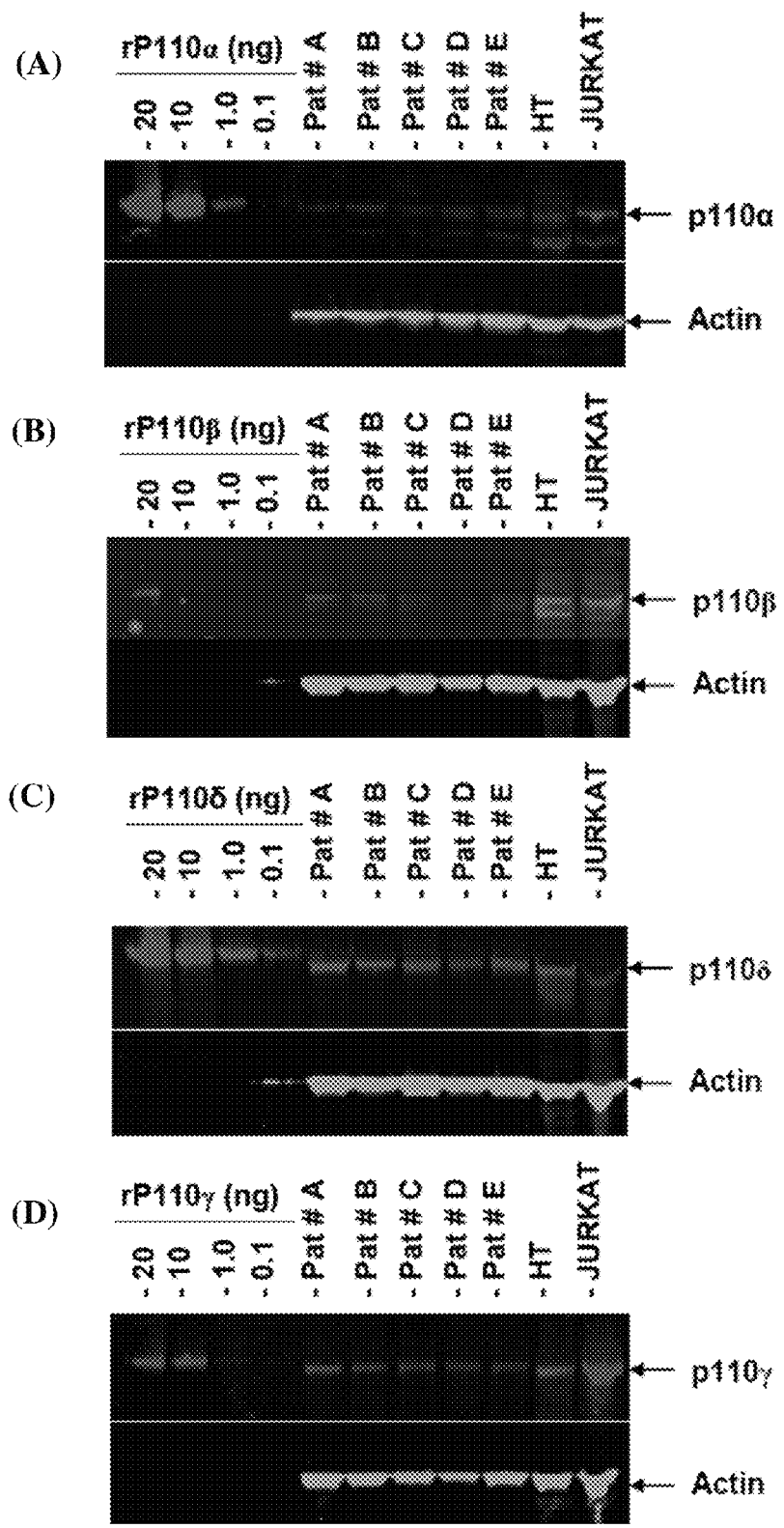
FIGS. 17A-D shows PAGE results of different PI3K isoform expression in CLL patient cells.

Expression of PI3K p110 α, β, γ and δ in a panel of lymphoma and leukemia cell lines is demonstrated in FIG. 15. Proteins from $10^6$ cells were separated by SDS-PAGE and analyzed by Western blot using antibodies specific for the α, β, γ and δ isoforms. Purified recombinant p110 proteins were used as controls. Anti-actin antibodies were used to assess equal loading of the samples. p110δ was consistently expressed at a high level while other p110 isoforms were highly variable. PI3K p110δ is known to be uniformly expressed in patient AML cells as discussed by Sujobert, et al., *Blood* 2005 106(3), 1063-1066.

EXAMPLE 19

Inhibitory Effect of Compound I on p110δ

Example 19 shows compound I inhibition of p110δ blocks PI3K signaling in leukemia and lymphoma cell lines with constitutive pathway activation.

The PI3K pathway is frequently deregulated in leukemia and lymphoma cell lines. 48% of cell lines, or 13 out of 27, were found to have constitutive p-AKT. In addition, PI3K pathway activation is dependent on p110δ. Compound I was found to inhibit constitutive AKT phosphorylation in 13 out of 13 cell lines.

Figure 27:
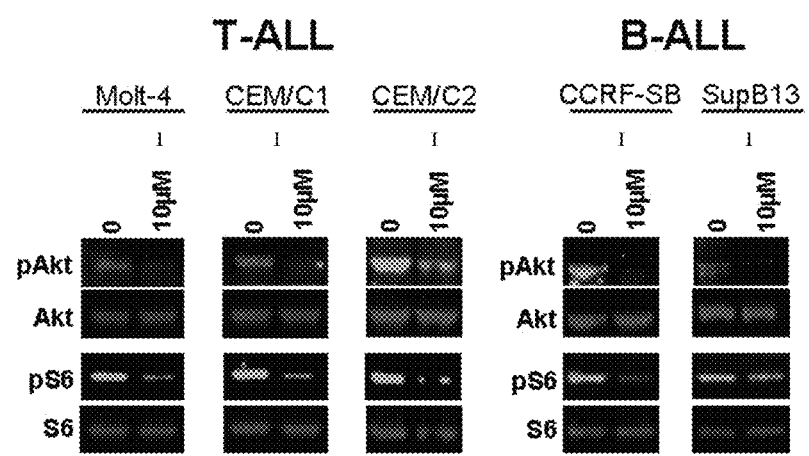
FIG. 27 shows the effects of a 10 μM concentration of compound I on the phosphorylation of Akt and S6 in ALL cell lines in SDS-PAGE.
Figure 28:
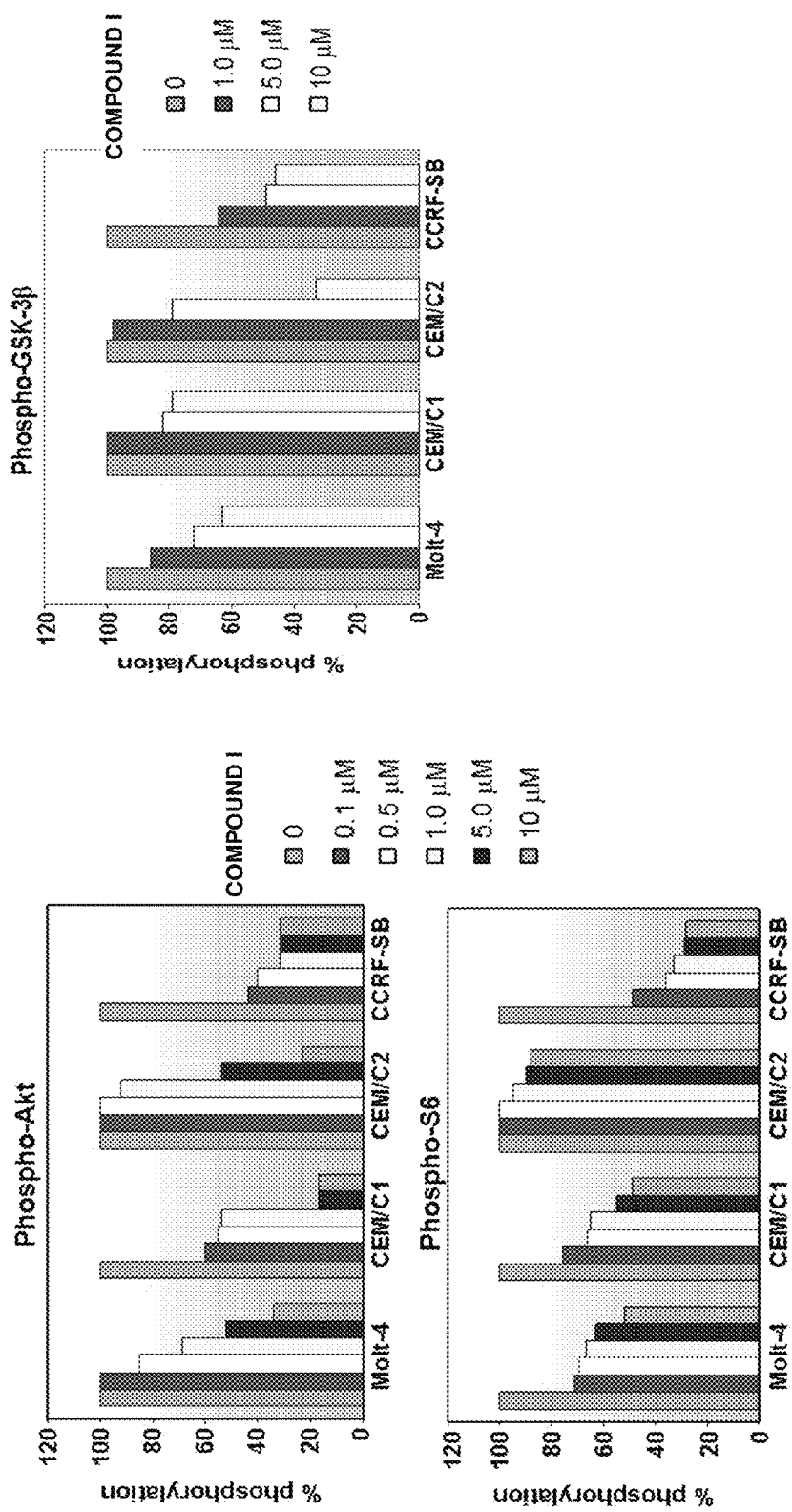
FIG. 28 shows a dose dependent reduction of phosphorylation of Akt, S6, and GSK-3β after treatment with a series of compound I dilutions.

PAGE results of FIG. 9 demonstrates that constitutive AKT phosphorylation was inhibited by the presence of compound I in each of 11 cell lines, including B-cell and T-cell lymphomas. Cells were incubated for 2 hrs with 10 μM compound I. Cell lysates were run on SDS-PAGE and transferred onto PDVF membrane and probed with appropriate antibodies. Compound I was found to inhibit constitutive AKT phosphorylation in 11 out of 11 cell lines. Additional cell line data for T-ALL and B-ALL cell lines is shown in FIG. 27. A decrease in Akt and S6 phosphorylation after exposure to a range concentrations of compound I (0.1 μM to 10 μM), was quantitated by densitometry, expressed as the percent change, FIG. 28.

EXAMPLE 20

Compound I Inhibits Proliferation and Apoptosis in Leukemia Cell Lines

Example 20 demonstrates that compound I inhibits proliferation and induces apoptosis in leukemia cell lines. FIGS. 16A-B show that treatment with compound I for 24 hours reduces cellular viability in a dose dependent manner.

Proliferation assays (AlamarBlue®) on ALL cell lines grown in the presence of 10% FBS serum and measurements were taken at 24 hrs. Proliferation was measured in triplicate wells in 96-well plates. The inhibition of PI3K signaling by compound I resulted in a block of cell cycle progression, and/or cell death. In each of six leukemia cell lines, viability was reduced by 40-50% with 10 micromolar concentrations of Compound I, FIG. 16A.

Induction of apoptosis by compound I. Cells were treated with DMSO (vehicle), 1 μM or 10 μM compound I for 24 hrs. The percentage of apoptotic cells was determined by Annexin V-FITC/7AAD staining. One experiment representative of different experiments that gave similar results is shown in FIG. 16B.

EXAMPLE 21

Expression of p110 Delta in CLL Cells

This example demonstrates PI3K p110δ and p110 δ isoform expression in patient CLL cells.

PI3K mediated signaling pathways have been implicated in CLL. These pathways have a role in cell proliferation, prevention of apoptosis and cell migration. Efforts were made to determine PI3K isoform expression in patient CLL cells.

CLL patient demographics are summarized below in Table 5.

TABLE 5

| CLL Patient Demographics (Total (N = 24)) | |
|---|---|
| I) Cytogenetic abnormalities | |
| 13q14.3 | 58% |
| 11q22.3 | 33% |
| 17p13.1 | 20% |
| Trisomy 12 | 12% |
| II) Treatment History | |
| Fludarabine refractory | 29% |
| Unknown | 54% |
| II) IgVH Status | |
| Mutated | 33% |
| Unmutated | 33% |
| Unknown | 33% |

The PAGE images of FIG. 17A-D compare the expression of p110α, p110δ, p110β, and p110γ in CLL cells of patients A-E. p110δ and p110γ is expressed in each patient compared to the other PI3K isoforms.

EXAMPLE 22

Compound I Induces Cleavage of Caspase 3 and PARP

Figure 18:
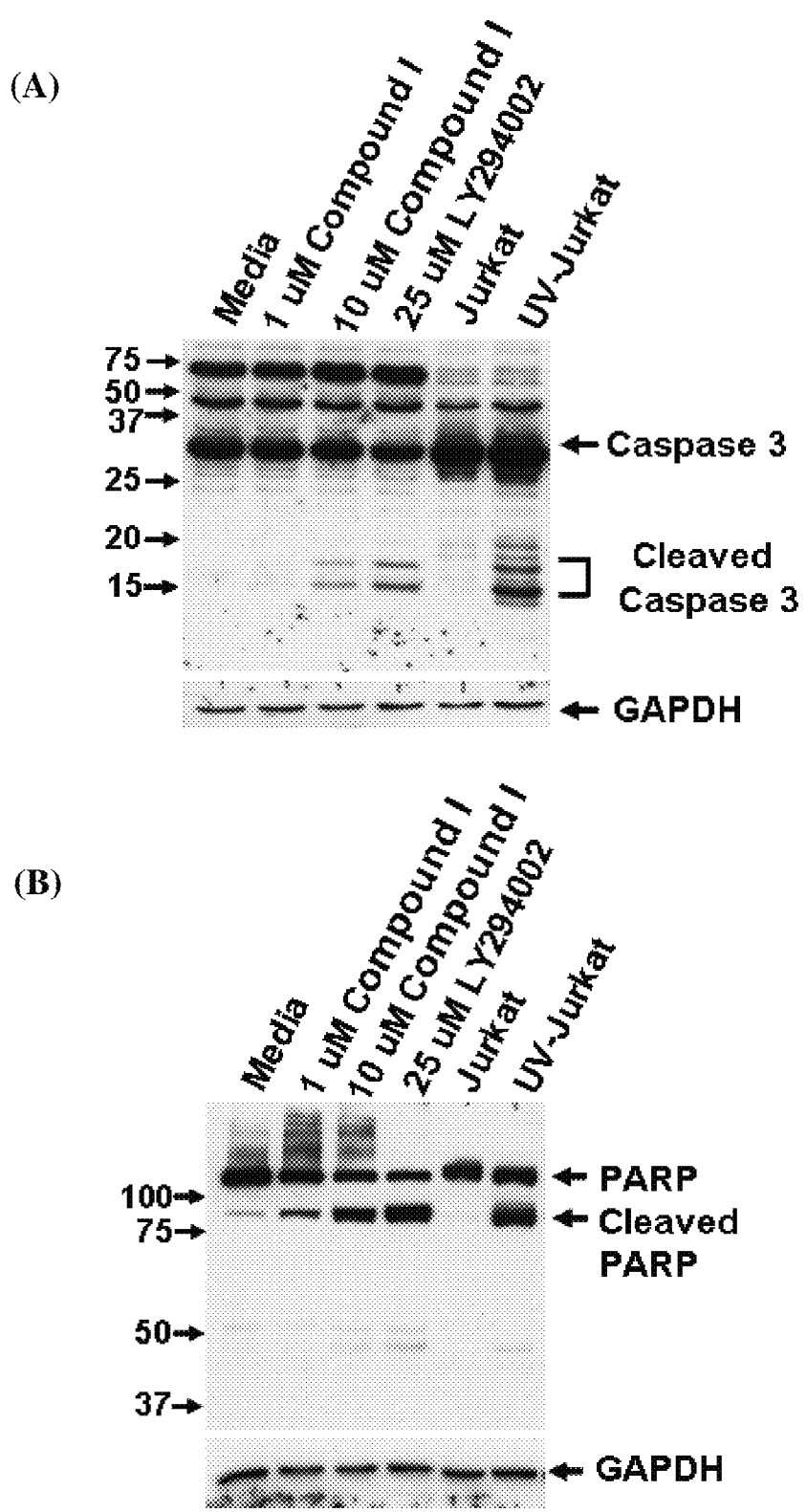
FIG. 18 shows the induction of (A) caspase 3 and (B) PARP cleavage in the presence of compound I.

This example demonstrates that compound I induced the cleavage of caspase 3 and PARP. FIGS. 18A-B show results of caspase 3 and PARP (Poly(ADP) Ribose Polymerase) cleavage in the presence of 1, 10 µM of compound 1 or 25 µM of LY294002.

Figure 29:
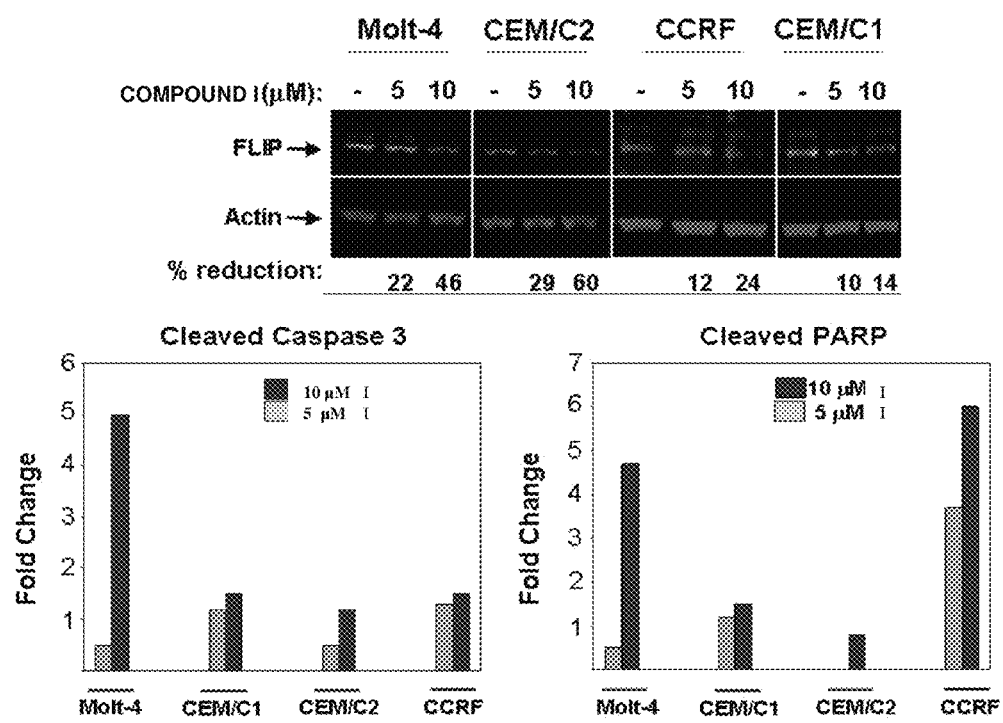
FIG. 29 shows dose dependent effects of compound I on ALL cell lines in the downregulation of cFLIP, cleavage of Caspase 3, and cleavage of PARP.

Further experiments provide evidence of compound I inducing caspase 2 and PARP cleavage. Cells were cultured with compound I or vehicle alone for 24 hrs. Thereafter, cells were lysed and sized-fractionated and immunoblotted with antibody directed against FLIP, FIG. 29. Additionally, whole cell lysates were added to MDS (Meso Scale Diagnostics) multi-spot 96-well 4 spot plates coated with Total caspase-3, cleaved caspase-3, cleaved PARP, and BSA. Proteins were detected with antibodies labeled with SULFO-TAG reagent and quantified. A dose dependent response in the cleavage of caspase 3 and PARP was achieved upon exposure to 5 or 10 µM of compound I.

EXAMPLE 23

Compound I Blocks PI3K Signaling

Figure 21:
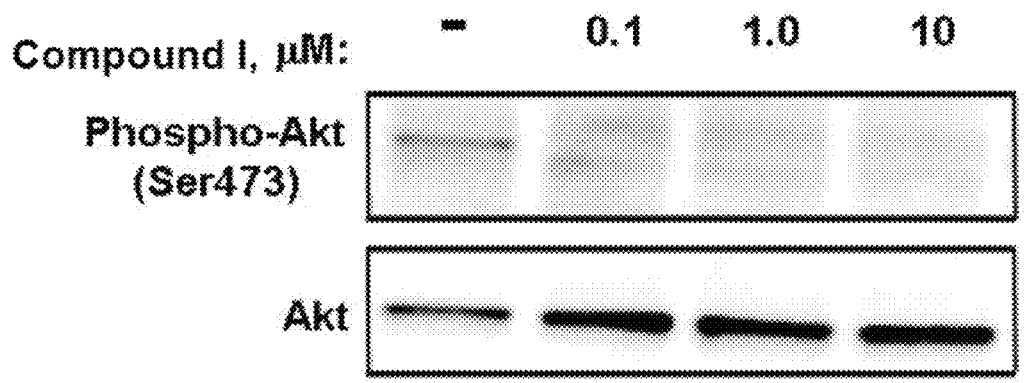
FIG. 21 shows the results of Phospho-Akt production in the absence or presence of 0.1, 1.0, 10 μM of compound I.

This example demonstrates that compound I blocks PI3K signaling in patient AML cells. PI3Kδ is implicated in signaling in AML patient cells. FIG. 21 shows the results of Phospho-Akt production in the absence or presence of 0.1, 1.0, 10 µM of Compound I. This provides evidence that compound I reduces phopsho-Akt production in patient AML cells.

EXAMPLE 24

Measurement of PI3K Signaling in Basophils Founding Whole-Blood

This example demonstrates a whole-blood assay for measurement of PI3K signaling in basophils using flow cytometry by the induction of CD63 surface expression.

Figure 22:
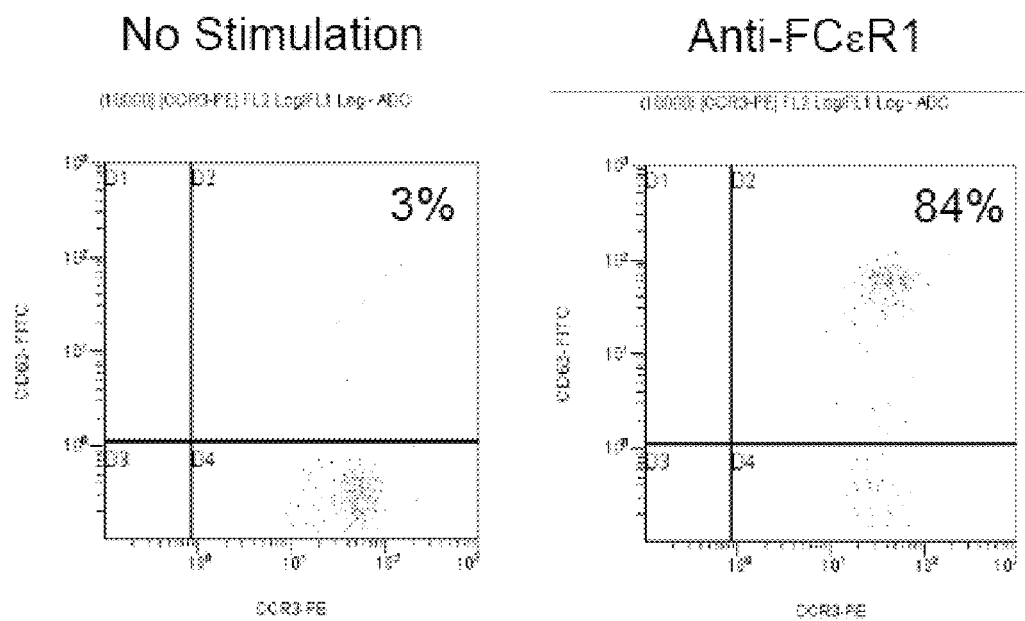
FIG. 22 shows flow cytometry results relating to PI3K signaling in basophils, demonstrating that (B) anti-FCεR1 or (C) fMLP increases CD63 expression compared to no stimulation (A).
Figure 22:
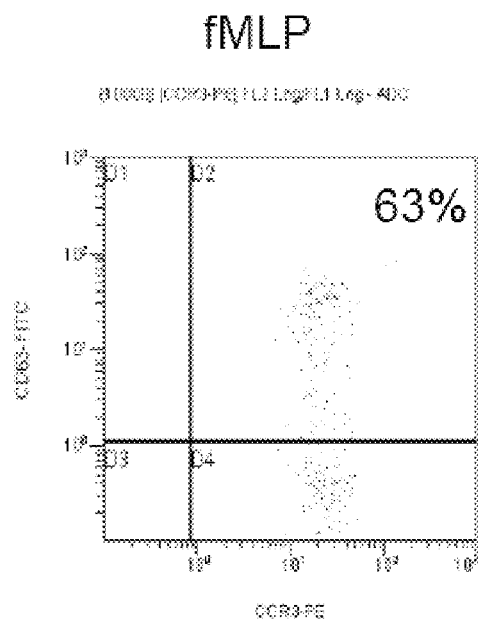

Inhibition of PI3K signaling in basophils permits compound I to be a useful pharmacodynamic marker. PI3K signaling is monitored by CD63 surface expression. In particular, p110δ mediates FCεR1 signaling and p110γ mediates fMLP receptor signaling. The flow cytometry analysis of PI3K mediated CD63 expression on basophils comprises the following sequential steps:
1. Collect peripheral blood
2. Basophil stimulation (fMLP or Anti-FCεR1 Mab)
3. Label basophils (Anti-CCR3-FITC and Anti-CD63-PE)
4. Lyse and fix cells
5. Analysis by flow cytometry FIG. 22A-C compares the results of A) no stimulation, B) stimulation with Anti-FCεR1, or C) stimulation with fMLP.

Figure 23:
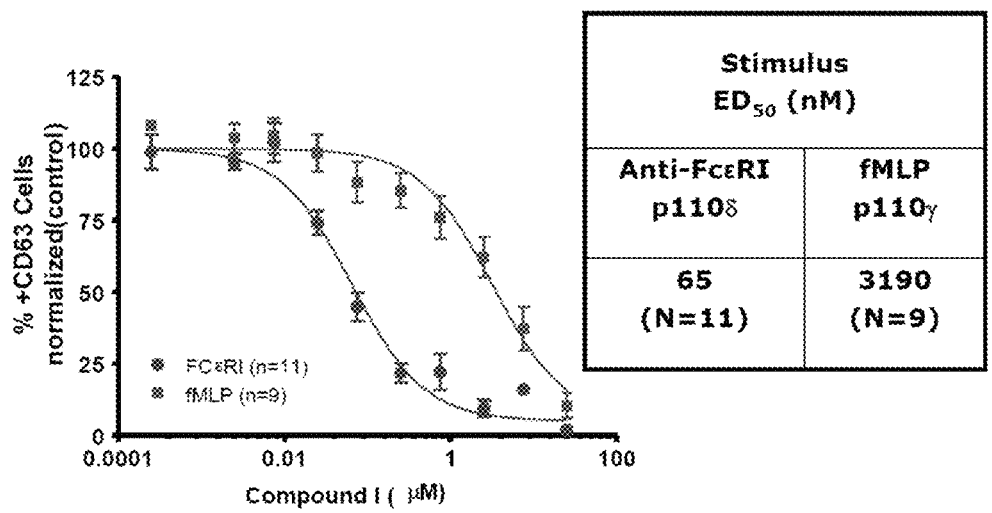
FIG. 23 shows inhibition of PI3K inhibition by compound I in basophils, and demonstrates that Compound I is especially effective at inhibition of CD63 expression induced by a p110δ pathway, but also effective at micromolar concentration to inhibit expression induced by a p110γ pathway.

FIG. 23 shows that Compound I is especially active where p110δ mediated signaling is most important, but is also relatively active where p110γ is utilized: it achieved 50% reduction in SD63 expression at <<1 µM for the p110δ test, and ca. 10 µM for the p110γ test. Basophil activation was measured in human whole blood using the Flow2 CAST® kit. Whole blood samples were treated with either vehicle or serial dilutions of compound I prior to activation of basophils either with anti-FcεRI mAb or fMLP. Cells were stained with the combination of anti-human CD63-FITC and anti-human CCR3-PE mAbs. The percent CD63 positive cells within the gated basophil population were determined in different treatment groups and normalized to the vehicle control.

EXAMPLE 25

Compound I Reduces Lymphadenopathy in CLL Patient

Figure 40:
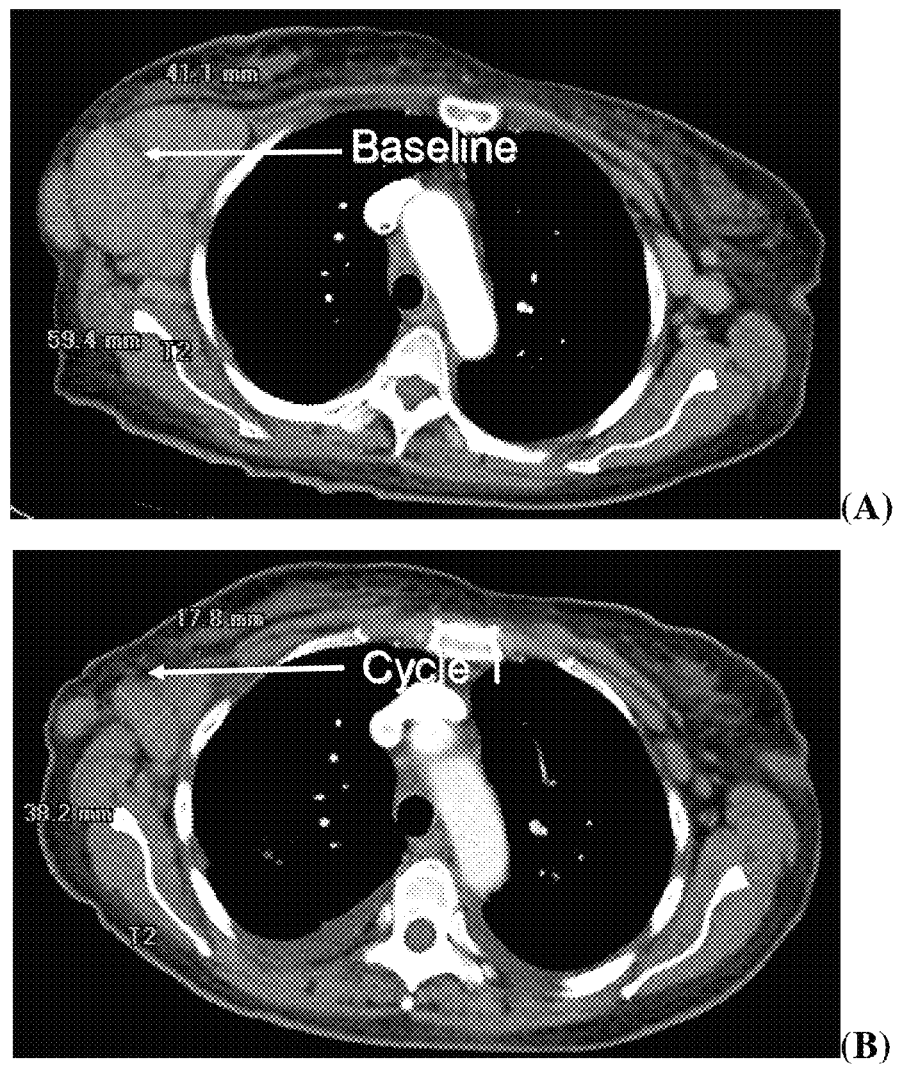
FIG. 40 show a computer tomography axillary image of a bulky lymphadenopathy in a patient with CLL (A) before treatment with compound I and (B) after 1 cycle of treatment with compound I.

This example provides evidence of the reduction in size of a bulky lymphadenopathy in a CLL patient with a del[17p]. A patient with del(17p) had an axillary lymphadenopathy, which was imaged by computed tomography (CT) to provide a baseline measurement of 5.9 cm×4.1 cm, FIG. 40A. After one cycle of treatment with compound I, the lymphadenopathy was reduced to a dimension of 3.8×1.8 cm, FIG. 40B. A cycle treatment was 28 days of continuous oral dosing at either 200 mg BID or 350 mg BID of compound I.

EXAMPLE 26

Limited Effect of Compound I on Glucose and Insulin Levels of a Subject

Figure 25:
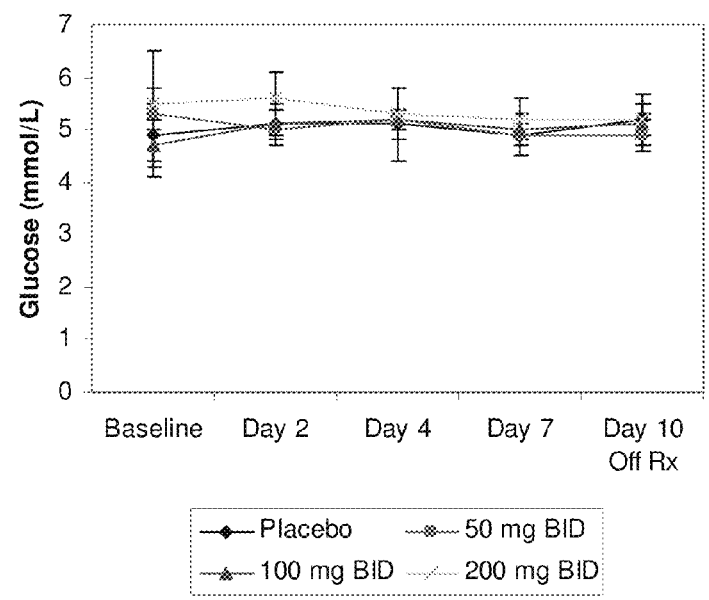
FIG. 25 shows the effects of various doses of compound I on (A) glucose and (B) insulin levels, exhibiting little off-target activity.
Figure 25:
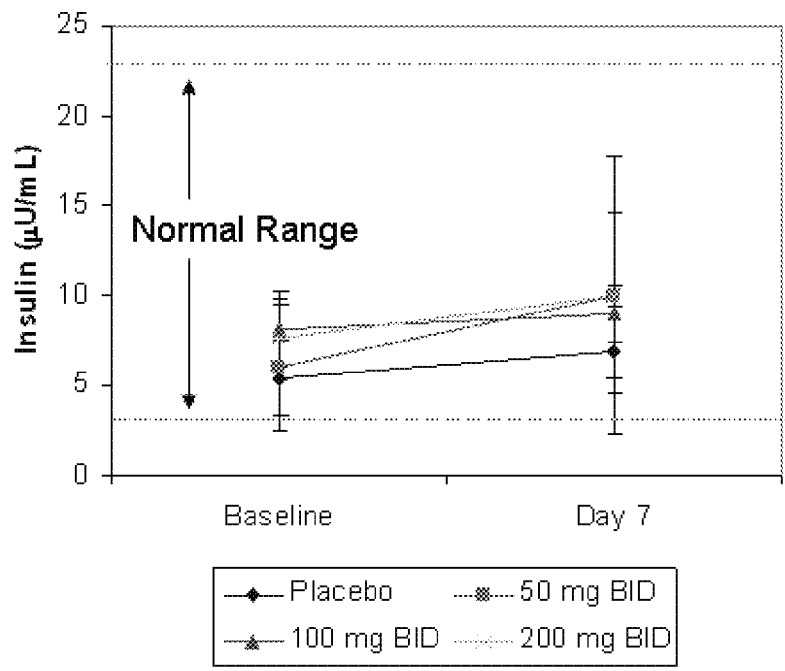

This example demonstrates that treatment with compound I has little or no effect on glucose and insulin levels. Compound I was administered at 50-200 mg amounts BID to a subject over a period of up to 10 days. Blood glucose and insulin concentrations were measured over time and compared to placebo results as shown in FIGS. 25A-B.

Blood glucose concentration remained steady after 10 days of treatment with even the highest dosage amount of compound I. Insulin levels remained within the normal range after 7 days of treatment with compound I. This provides evidence that compound I has little or no effect on glucose and insulin levels.

EXAMPLE 27

Materials and Methods

This example provides information on materials and methods of carrying out the experiments described in Examples 28-35 which relate to the use of compound I in the treatment of multiple myeloma.

Materials p110δ inhibitor compound I and compound II were provided by Calistoga Pharmaceuticals, (Seattle, Wash.). The sample of compound I and II used was over 95% the S enantiomer. Compound I was dissolved in Dimethyl sulphoxide at 10 mM and stored at −20° C. for in vitro study. Compound II was dissolved in 1% carboxyl methylcellulose (CMC)/0.5% Tween 80 and stored at 4° C. for in vivo study. Recombinant human P110α, β, γ, and δ were reconstituted with sterile phosphate-buffered saline (PBS) containing 0.1% BSA. bortezomib was provided by Millennium Pharmaceuticals (Cambridge, Mass.). 3-Methyladenine was purchased from Sigma-Aldrich (St. Louis, Mo.).

Cell Culture

Dex-sensitive (MM.1S) and resistant (MM.1R) human MM cell lines were kindly provided by Dr. Steven Rosen (Northwestern University, Chicago, Ill.). H929, RPMI8226, and U266 human MM cell lines were obtained from American Type Culture Collection (Manassas, Va.). Melphalan-resistant RPMI-LR5 and Doxorubicin (Dox)-resistant RPMI-Dox40 cell lines were kindly provided by Dr. William Dalton (Lee Moffitt Cancer Center, Tampa, Fla.). OPM1 plasma cell leukemia cells were provided by Dr. Edward Thompson (University of Texas Medical Branch, Galveston). IL-6-dependent human MM cell line INA-6 was provided by Dr. Renate Burger (University of Kiel, Kiel, Germany). LB human MM cell line was established in the laboratory. Phenotypic analysis revealed no cytogenetic abnormalities. Phenotypic analysis is shown in table 6. CD expression profile of LB cell line, defined by flow-cytometric analysis.

TABLE 6

| LB expression | |
|---|---|
| CD marker | % expression |
| CD3 | 5.5% |
| CD19 | 61.7% |
| CD20 | 97.2% |
| CD38 | 54.1% |
| CD40 | 96.8% |
| CD49e | 5.9% |
| CD70 | 98.0% |
| CD138 | 96.3% |

All MM cell lines were cultured in RPMI1640 medium. Bone marrow stromal cells (BMSCs) were cultured in Dulbecco's modification of Eagle's medium (DMEM) (Sigma) containing 15% fetal bovine serum, 2 mM L-glutamine (Life Technologies), 100 U/mL penicillin, and 100 µg/mL streptomycin (Life Technologies). Blood samples collected from healthy volunteers were processed by Ficoll-Paque™ gradient to obtain peripheral blood mononuclear cells (PBMNCs). Patient MM and BM cells were obtained from BM samples after informed consent was obtained per the Declaration of Helsinki and approval by the Institutional Review Board of the Dana-Farber Cancer Institute (Boston, Mass.). BM mononuclear cells were separated using Ficoll-Paque™ density sedimentation, and plasma cells were purified (>95% CD138+) by positive selection with anti-CD138 magnetic activated cell separation micro beads (Miltenyi Biotec, Auburn, Calif.). Tumor cells were also purified from the BM of MM patients using the RosetteSep negative selection system (StemCell Technologies, Vancouver, BC, Canada).

Growth Inhibition Assay

The growth inhibitory effect of compound I on growth of MM cell lines, PBMCs, and BMSCs was assessed by measuring 3-(4,5-dimethylthiazol-2-yl)-2,5-diphenyl tetrasodium bromide (MTT; Chemicon International, Temecula, Calif.) dye absorbance.

Effect Of Compound I on Paracrine MM Cell Growth in the BM

MM cells (2×104 cells/well) were cultured for 48 h in BMSC coated 96-well plates (Costar, Cambridge, Mass.), in the presence or absence of drug. DNA synthesis was measured by [3H]-thymidine (Perkin-Elmer, Boston, Mass.) uptake, with [3H]-thymidine (0.5 µCi/well) added during the last 8 h of 48 h cultures. All experiments were performed in quadruplicate.

Transient Knockdown of P110δ Expression

INA-6 cells and LB cells were transiently transfected with siRNA ON-TARGET plus SMART pool P110δ or nonspecific control duplex (Dharmacon Lafayette, Co) using Cell Line Nucleofector Kit V (Amaxa Blosystems Gaitherburg, Md.).

Immunofluorescence

Viable MM cells (2.5×104) were pelleted on glass slides by centrifugation at 500 rpm for 5 minutes using a cytospin system (Thermo Shandon, Pittsburgh, Pa.). Cells were fixed in cold absolute acetone and methanol for 10 min. Following fixation, cells were washed in phosphate-buffered saline (PBS) and then blocked for 60 min with 5% EBS in PBS. Slides were then incubated with anti-CD138 antibody (Santa Cruz Biotechnology, Santa Cruz, Calif.) at 4° C. for 24 h, washed in PBS, incubated with goat anti-mouse IgG for 1 h at 4° C., and analyzed using Nikon E800 fluorescence microscopy.

Detection And Quantification of Acidic Vesicular Organelles (AVO) with Acridine Orange Staining.

Autophagy was characterized by sequestration of cytoplasmic proteins and development of AVOs. To detect and quantify AVOs in compound 1 or 3MA-treated cells, vital staining was performed for 15 min with acridine orange at a final concentration of 1 µg/ml. Samples were examined under a fluorescence microscope.

Angiogenesis Assay

The anti-angiogenic activity of compound I was determined using an in vitro Angiogenesis Assay Kit (Chemicon, Temecula, Calif.). HUVEC and endothelial growth media were obtained from Lonza (Walkersville, Md., USA). HUVEC were cultured with compound I on polymerized matrix gel at 37° C. After 8 h, tube formation was evaluated using Leika DM IL microscopy (Leica Microsystems, Wetzlar, Germany) and analyzed with IM50 software (Leica Microsystems Imaging Solutions, Cambridge, UK). HUVEC cell migration and rearrangement was visualized, and the number of branching points counted.

Western Blotting

MM cells were cultured with or without compound I; harvested; washed; and lysed using radioimmuno precipitation assay (RIPA) buffer, 2 mM $Na_3VO_4$, 5 m M NaF, 1 mM phenylmethylsulfonyl fluoride (5 mg/ml). Whole-cell lysates were subjected to sodium dodecyl sulfate-polyacrylamide gel electrophoresis (SDS-PAGE) separation, transferred to Pure Nitrocellulose membranes (Bio-Rad Laboratories, Hercules, Calif.), and immunoblotted with anti-AKT, phospho(p)-AKT (Ser473, Thr 308), ERK1/2, P-ERK1/2, P-PDK1, STAT, P-STAT, P-FKRHL, P-70S6K, LC3, and PI3K/p110 α Abs (Cell Signaling Danvers, Mass.); anti-p110β, PI3K/p110δ, Glyceraldehyde 3-phosphate dehydrogenase (GAPDH), α-tubulin, and actin Abs (Santa Cruz Biotechnology, Calif.); and anti-p110γ Ab (Alexis, San Diego, Calif.): and anti-LC3 Ab (Abgent, San Diego, Calif.).

ELISA

Cytokine secretion by human BMSCs cocultured with MM cells was assessed by ELISA. BMSCs were cultured in 96-well plates with varying concentrations of compound I, with or without INA-6 cells. After 48 h, supernatants were harvested and stored at −80° C. Cytokines were measured using Duo set ELISA Development Kits (R&D Systems, Minneapolis, Minn.). All measurements were carried out in triplicate.

Human Cytokine Array

The cytokine levels in culture supernatants were assessed using Proteome Profiler Antibody Arrays Panel A (R&D Systems, Minneapolis, Minn.), Supernatants from co-cultures with BMSCs were incubated for 4 hours with membranes arrayed with Abs against 37 cytokines, according to manufacturer's instructions.

Murine Xenograft Models of Human MM

CB17 SCID mice (48-54 days old) were purchased from Charles River Laboratories (Wilmington, Mass.). All animal studies were conducted according to protocols approved by the Animal Ethics Committee of the Dana-Farber Cancer Institute. Mice were inoculated subcutaneously in the right flank with 3×106 LB cells in 100 μL RPMI-1640. When tumors were palpable, mice were assigned into the treatment groups receiving 10 mg/kg or 30 mg/kg gavages twice daily; and 7 mice in the control group receiving vehicle alone. Caliper measurements of the longest perpendicular tumor diameters were performed every alternate day to estimate the tumor volume using the following formula representing the 3D volume of an ellipse: 4/3×(width/2)2×(length/2). Animals were sacrificed when tumors reached 2 cm or the mice appeared moribund. Survival was evaluated from the first day of treatment until death. Tumor growth was evaluated using caliper measurements from the first day of treatment until day of first sacrifice, which was day 12 for the control group and days 17 and 19 for the treatment groups. The images were captured with a canon IXY digital 700 camera. Ex vivo analysis of tumor images was captured with a LEICA DM IL microscope and LEICA DFC300 FX camera at 40u/0.60 (Leica, Heidelberg, Germany).

Human fetal bone grafts were implanted into CB17 SCID-mice (SCID-hu). Four weeks following bone implantation, 2.5×106 INA-6 cells were injected directly into the human BM cavity in the graft in a final volume of 100 μl of RPMI-1640 medium. An increase in the levels of soluble human IL-6 receptor (shuIL-6R) from INA-6 cells was used as an indicator of MM cell growth and burden of disease in SCID-hu mice. Mice developed measurable serum shuIL-6R approximately 4 weeks following INA-6 cell injection, and then received either 10 or 30 mg/kg drug or vehicle alone daily for 7 weeks. Blood samples were collected and assessed for shuIL-6R levels using an enzyme-linked immunosorbent assay (ELISA, R&D Systems. Minneapolis Minn.).

Statistical Analysis

Statistical significance was determined by Dunn's multiple comparison tests. The minimal level of significance was p<0.05. Survival was assessed using Kaplan-Meier curves and log-rank analysis. The combined effect of compound I and bortezomib was analyzed by isobologram analysis using the CalcuSyn software program (Biosoft, Ferguson, Mo.); a combination index (CI)<0.7 indicates a synergistic effect.

EXAMPLE 28

Expression of p110 Delta in MM Cells

Figure 30A:
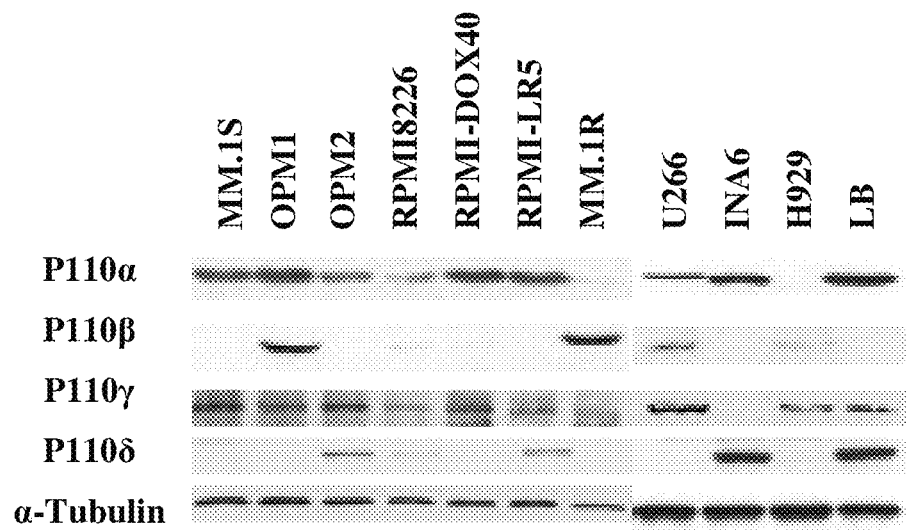
FIG. 30 shows expression of p110 delta in A) MM cell lines and B) patient MM cells; and C) in MM.1S and LB cells.
Figure 30B:
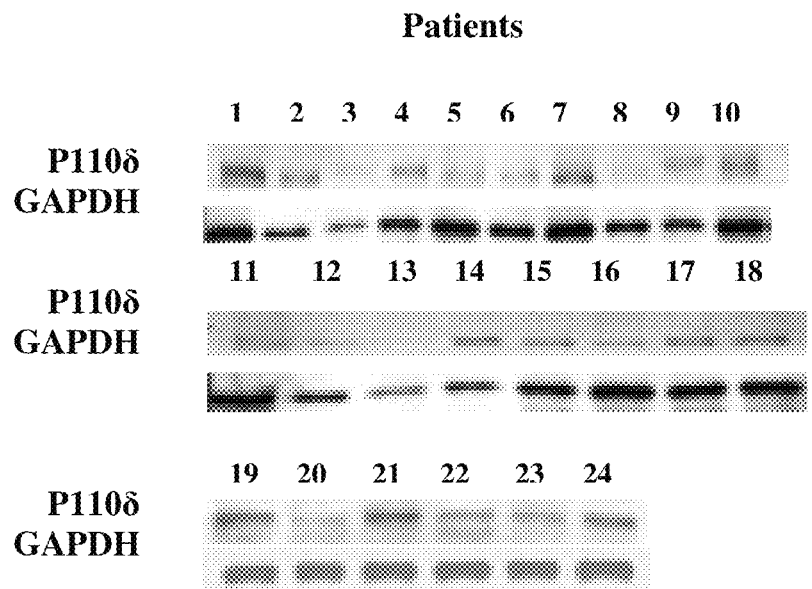

This example demonstrates that p110 delta is highly expressed in patient MM cells. To assess PI3K/p110 expression, Abs was used against recombinant human PI3K/p110α, β, γ, and δ proteins with specific immunoreactivity against these isoforms. The expression of p110δ in 11 mM cell lines (MM.1S, OPM1, OPM2, RPMI8226, DOX40, LR5, MM.1R, U266, INA-6, H929, and LB), as well as 24 patient MM samples were evaluated and immunoblots shown in FIGS. 30A and 30B. FIG. 30A shows expression of p110-α, -β, -γ, and δ in MM cell lines detected by immunoblotting using specific antibodies. Anti-α-Tubulin MAb served as a loading control. p110δ in patient MM cells was detected by immunoblotting using anti-P110δ Ab (FIG. 30B).

Figure 30C:
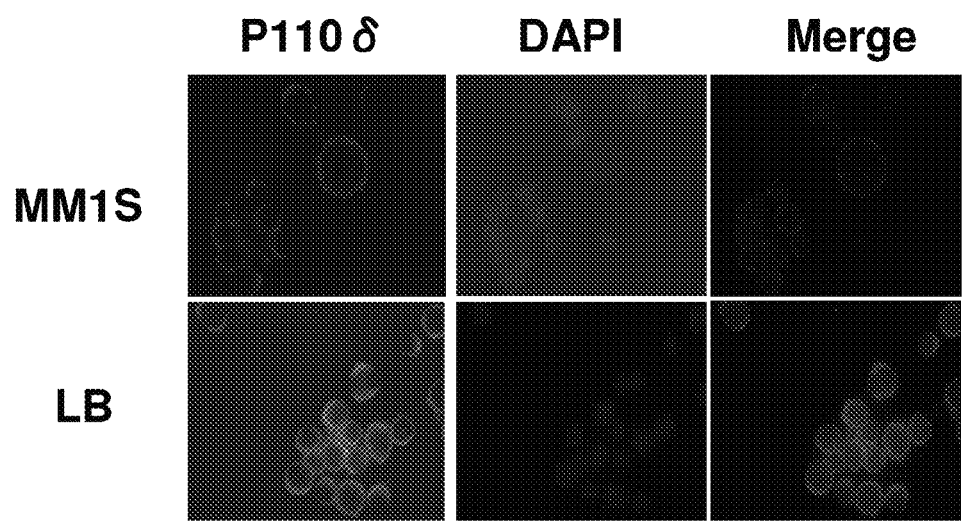

Anti-GAPDH MAb served as a loading control. INA-6 and LB cells strongly expressed p110δ, whereas MM.1S, OPM1, MM.1R, Dox40, U266 or H929 lacked p110δ expression (FIG. 30A).

p110δ expression in MM.1S and LB cells was confirmed by immunofluorescence analysis (FIG. 30C). Human recombinant P110-α, -β, -γ, -δ proteins in SDS sample buffer were heated for 3 min prior to loading on gel. (10-20 μg per lane.) Recombinant human P110-α, -β, -γ, -δ proteins were detected by Immunoblot analysis. Levels of P110 δ were measured in MM1S and LB cells using P110 δ specific FITC conjugated secondary antibodies. P110δ stained green, and nucleic acids (DAPI) stained blue.

Western blotting revealed no correlation of between p110δ expression and expression of the other isoforms (α, β and γ). Importantly, all patient MM cells also expressed p110δ, (FIG. 30B).

EXAMPLE 29

Cytotoxicity of Compound I on MM Cells

This example demonstrates that compound I has selective cytotoxicity against cells with p110δ. Specifically, compound I potently induced cytotoxicity in p110 delta positive MM cells as well as in primary patient MM cells without cytotoxicity in peripheral blood mononuclear cells from healthy donors, suggesting a favorable therapeutic index.

The growth inhibitory effect of p110δ knockdown in MM cells was evaluated. LB and INA-6 cells were transfected with P110δ siRNA (Si) or control siRNA (Mock). After 24 h, expression of P110 δ was determined by western blot analysis, see FIG. 31A. INA-6 cells were transfected with p110δ siRNA or control siRNA, and then cultured for 72 hours. Cell growth was assessed by MTT assay, see FIG. 31B. Data indicates mean±SD of triplicate cultures, expressed as fold of control. Transfection with p110δ siRNA, but not mock siRNA, down-regulated p110δ and inhibited MM cell growth at 72 h (FIGS. 31A and 31B). The growth inhibitory effect of p110δ specific small molecule inhibitor compound I in MM cell lines, PBMCs, and patient MM cells was evaluated.

Compound I induced cytotoxicity against LB and INA-6 mM cells (p110δ-positive) in a dose- and time-dependent fashion; in contrast, minimal cytotoxicity was noted in p110δ-negative cell lines (FIG. 31C). The legend for FIG. 31C: LB (□), INA-6 (Δ), RPMI 8226(○), OPM2 (◇), H929 (●), U266 (◆), RPMI-LR5 (▲) and OPM1 (■) MM cells were cultured with or without compound I for 48 h.

Importantly, compound I also induced cytotoxicity against patient MM cells (FIG. 31D), without cytotoxicity in PBMCs from 4 healthy volunteers at concentrations up to 20 μM (FIG. 31E). Patients MM cells isolated from BM by negative selection were cultured with compound I for 48 h. Peripheral blood mononuclear cells isolated from healthy donors were cultured with compound I for 72 h. Data represent mean±SD viability, assessed by MTT assay of triplicate cultures, expressed as percentage of untreated controls. These results strongly suggest that sensitivity to compound I is associated with P110δ expression, and suggest a favorable therapeutic window.

To determine whether the cytotoxicity induced by compound I is via apoptosis, the cleavage of caspases and PARP by western blot analysis was examined. INA-6 cells were cultured with compound I (0-5 μM) for 120 h. Total cell lysates were subjected to immunoblotting using anti-caspase-3, -8, -9, PARP, and α-tubulin Abs. FL indicates full-length protein, and CL indicates cleaved protein. Significantly increased cleavage of caspase-8, caspase-9, caspase-3, and PARP was observed in INA-6 mM cells treated with compound I for 120 h (FIG. 31F). These results indicate that cytotoxicity triggered by compound I is mediated, at least in part, via caspase-dependent (both intrinsic and extrinsic) apoptosis.

EXAMPLE 30

Inhibition of AKT and ERK Phosphorylation by Compound I

This example demonstrates the Inhibition of AKT and ERK phosphorylation by compound I.

An important downstream effector of PI3K is the serine/threonine protein kinase AKT, which is activated by phosphorylation of Thr308 in the activation loop of the kinase domain and Ser473 in the C-terminal tail. Phosphorylation of both sites requires an interaction between the N-terminal pleckstrin homology domain of AKT and membrane phosphoinositide generated by PI3K. It was shown that compound I inhibits both domains, suggesting that P110δ is the predominant isoform responsible for PI3K signaling in MM cell lines.

Inhibition of AKT and ERK pathways in INA-6 cells by compound I was examined. INA-6 cells were cultured with Compound I or LY294002 for 12 h, FIG. 32A. Actin Ab was used as a loading control. INA-6 and MM.1S cells were cultured with Compound I (0, 0.25, 1.0, 5.0 μM) for 6 hours, FIG. 32B. LB and INA-6 cells were cultured with compound I for 0-6 hours, FIG. 32C. Whole cell lysates were subjected to immunoblotting using AKT, P-AKT (Ser473 and Thr308), ERK1/2, P-ERK1/2, P-PDK1, and P-FKRHL antibodies. α-tubulin is used as a loading control.

Compound I significantly blocked phosphorylation of AKT and ERK1/2 in p110δ positive INA-6 cells (FIG. 32A), but did not affect phosphorylation of AKT or ERK in MM.1S cells with low expression of P110δ (FIG. 32B). Compound I also significantly inhibited phosphorylation of upstream PDK-1 and downstream FKHRL in INA-6 and LB MM cells in a time- and dose-dependent fashion (FIG. 32C), further confirming inhibition of a both PI3K/AKT and ERK pathways in these cells.

EXAMPLE 31

Compound I Induces AVO Development and Autophagy

This example demonstrates the ability of compound I to trigger both apoptosis and autophagy.

AKT regulates autophagy, thus investigation of compound I in inducing autophagy in LB and INA-6 mM cells was carried out.

INA-6 and LB MM cells were treated with 5 μM Compound I for 6 h. Compound I treatment induced LC3 accumulation in LB and INA-6 cells, evidenced by fluorescence microscopy or transmission electron microscopy. Autophagosome formation was defined by the accumulation of LC3; arrows indicate autophagosomes, FIG. 33A.

INA-6 cells were treated with 5 μM Compound I or serum starvation for 6 h, stained with 1 μg/mL acridine orange for 15 min, and analyzed by fluorescence microscopy, FIG. 33B.

Figure 33C:
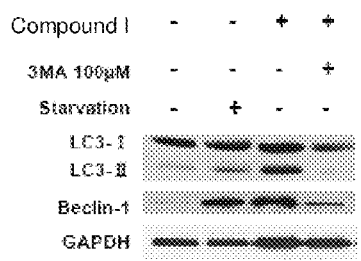
FIG. 33C shows immunoblots of LC3 and beclin-1 protein levels from INA-6 cells treated with or without compound 1 and 3-MA (3-methyl adenine, a known inhibitor of autophagy).

LC3 and beclin-1 protein levels were determined by western blotting using LC3 and beclin-1 antibodies of lysates from INA-6 cells treated with Compound I, with or without 3-MA, FIG. 33C. GAPDH served as a loading control.

Immunofluorescence analysis showed markedly increased LC 3 staining in INA-6 and LB cells triggered by compound I (5 μM, 6 h) treatment (FIG. 33A). Electron microscopic analysis also showed increased autophagic vacuoles (arrows) in MM cells treated with compound I. Since autophagy is characterized as acidic vesicular organelle (AVO) development, acridine orange staining was carried out. As shown in FIG. 33B, vital staining with acridine orange revealed development of AVOs in compound I—treated LB and INA-6 cells. Moreover, markedly increased LC3-II and Beclin1 protein were detected in INA-6 mM cells after 6 h treatment with compound I, which was blocked by 3-MA autophagic inhibitor (FIG. 33C).

Figure 33D:
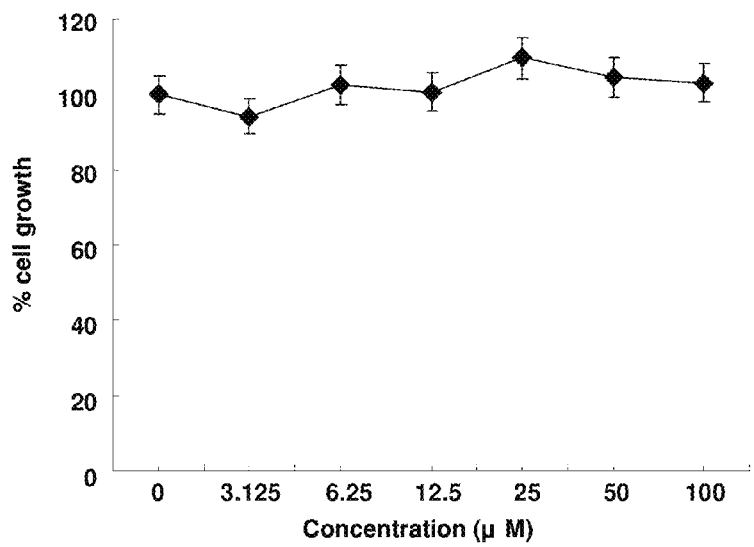
FIG. 33D shows % growth of p110δ positive LB cells after treatment with up to 100 μM of 3-MA for 24 hours.

No cytotoxicity in INA-6 and LB cells was induced by 3-MA at concentrations up to 100 μM, FIG. 33D. P110 δ positive LB cells (♦) were treated with 3-MA (0-100 μM) for 24 h. Data represent means (±SD) of triplicate cultures.

These results indicate that compound I induces development of AVOs and autophagy at earlier time points than induction of caspase/PARP cleavage.

Autophagy degrades cellular components, recycles cellular constituents, and responds to various cellular stress. In this example, LC3-II, a hallmark of autophagy, is induced by compound I treatment in p110 δ positive MM cell lines. Importantly, compound I treatment resulted in a marked increase in autophagy, evidenced by the presence of autophagic vacuoles in the cytoplasm, formation of AVOs, membrane association of microtubule-associated protein I of LC3 with autophagosomes, and a marked induction of LC3-II protein. Electron microscopic analysis confirmed that compound I induced autophagosomes. LC3-II was expressed through LC3-I conversion. Conversely, autophagy induced by compound I was suppressed by 3-MA, a specific inhibitor of autophagy. These studies suggest that early cytotoxic effects of compound I are associated with autophagy.

EXAMPLE 32

Compound I Inhibits Cell Growth in the Presence of BMSC

This example demonstrates the ability of compound I to inhibit paracrine MM cell growth with BMSCs.

Figure 34A:
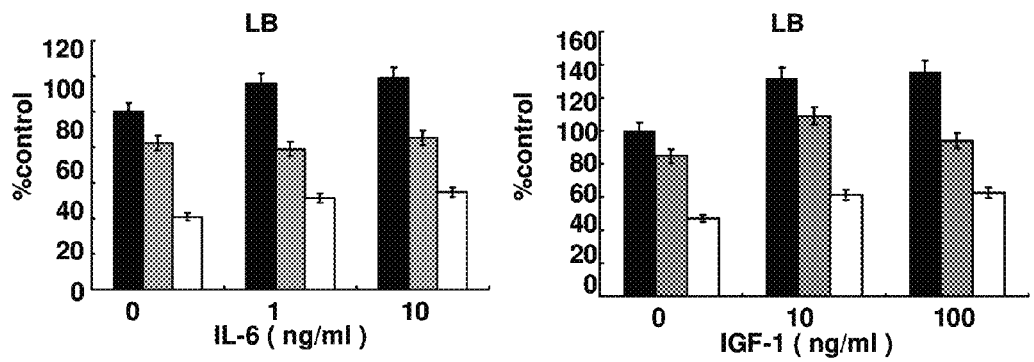
FIG. 34 shows the levels of growth inhibition of A) LB or B) INA-6 cells co-cultured with 0, 5, and 10 μM of compound I in the presence or absence of varying amounts of IL-6 or IGF-1; Legend: control media (■); compound I at 5.0 μM (▨) or 10 μM (□).
FIGS. 34C and 34D show MM cell growth inhibition in the presence of BMSC. Legend for 34C only: control media (□), Compound I 2.5 μM (▨), 5 μM (▨), and 10 μM (■).
FIG. 34F shows immunoblots of AKT and ERK expression profiles in INA-6 cells treated with compound I cultured with our without BMSCs.
FIG. 34G shows % BMSC cell growth in two different patients after culturing with compound I for 48 hours.
Figure 34B:
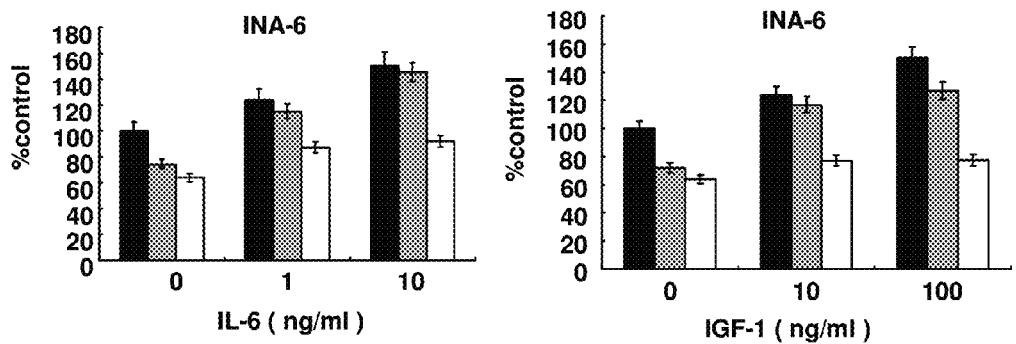

Since IL-6 and IGF-1 induces growth and anti-apoptosis in MM cells, compound I was examined in overcoming the effects of these cytokines in INA-6 and LB MM cells. LB and INA-6 cells were cultured for 48 h with control media (■); or with compound I at 5.0 μM (▨) or 10 μM (□), in the presence or absence of IL-6 (1 and 10 ng/ml), FIG. 34A, or IGF-1 (10 and 100 ng/mL), FIG. 34B. DNA synthesis was determined by measuring [3H]-thymidine incorporation during the last 8 h of 72 h cultures. Data represent means (±SD) of triplicate cultures. Neither IL-6 nor IGF-1 protected against the growth inhibition induced by compound I (FIGS. 34A and 34B).

The BM microenvironment confers proliferation and drug-resistance in MM, thus MM cell growth inhibitory effect of compound I in the presence of BMSCs was examined.

Figure 34C:
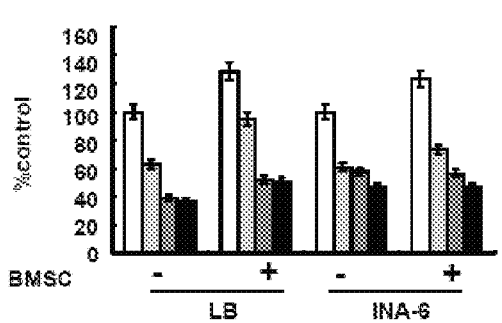

LB and INA-6 mM cells were cultured for 48 h with control media (□), and with 2.5 μM (▨), 5 μM (▨), and 10

μM (■) of Compound I, in the presence or absence of BMSCs, FIG. 34C. DNA synthesis was determined by [3H]-thymidine incorporation. Data represent means (±SD) of triplicate cultures.

Figure 34D:
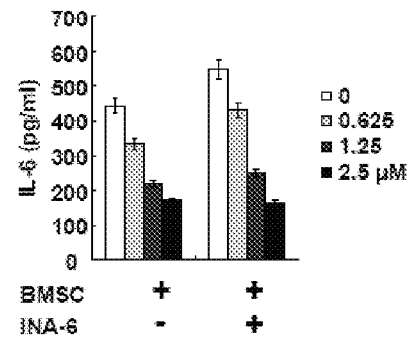

IL-6 in culture supernatants from BMSCs treated with compound I (0-2.5 μM) was measured by ELISA, FIG. 34D. Error bars indicate SD (±).

Figure 34E:
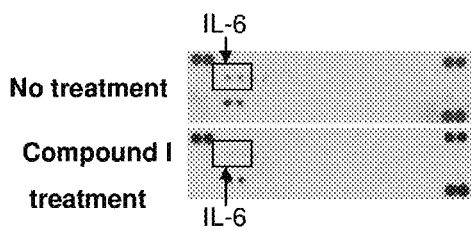

BMSCs were cultured with 1.0 μM compound I or control media for 48 h; cytokines in culture supernatants were detected using cytokine arrays, FIG. 34E.

Figure 34F:
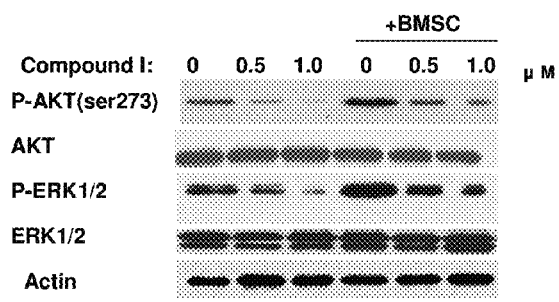

INA-6 cells cultured with or without BMSCs were treated with compound for 48 h. Total cell lysates were subjected to immunoblotting using indicated antibodies, FIG. 34F. Actin was used as a loading control.

BMSCs from 2 different patients (□, ◇) were cultured with compound I (0-20 μM) for 48 h. Cell viability was assessed by MTT assay, FIG. 34G. Values represent mean±SD of triplicate cultures.

Figure 34G:
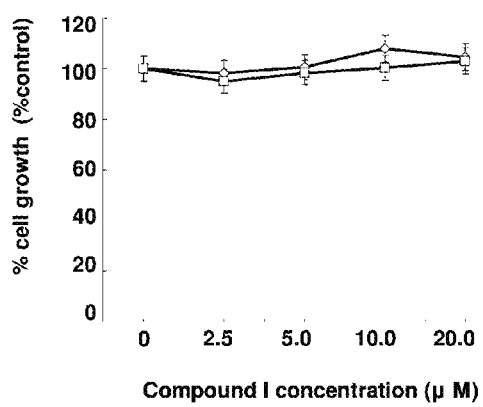

Importantly, compound I inhibited growth and cytokine secretion (FIG. 34C-E), as well as phosphorylation of AKT and ERK (FIG. 34F), induced by BMSCs. In contrast, no significant growth inhibition in BMSCs was noted (FIG. 34G). These results indicate that compound I blocks paracrine MM cell growth in the context of the BM microenvironment.

EXAMPLE 33

Compound I Inhibits Angiogenic HuVEC Tubule Formation

This example demonstrates the ability of Compound I to inhibit HuVEC tubule formation. The role of PI3K, specifically p110 isoform, in angiogenesis was investigated. Endothelial cells are an essential regulator of angiogenesis for tumor growth. Both Akt and ERK pathways are associated with endothelial cell growth and regulation of angiogenesis; and importantly, endothelial cells express p110δ. This example also demonstrates that compound I blocks in vitro capillary-like tube formation, associated with down regulation of Akt phosphorylation.

Figure 35A:
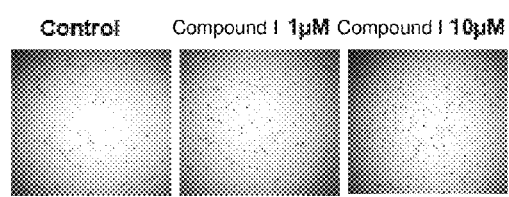
FIG. 35A shows microscopic images of HuVECs (human umbilical vein endothelial cells) cultured with 0, 1 and 10 μM of compound I for 8 hours and microtubule formation assessed.
Figure 35B:
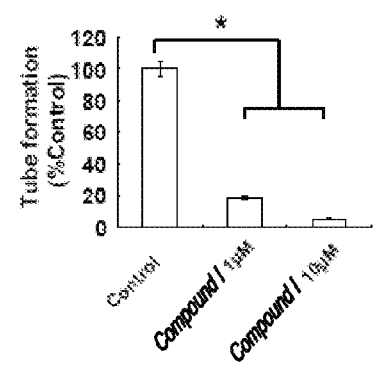
FIG. 35B shows a bar chart summarizing endothelial cell tube formation in HuVEC cells treated with compound I.

The effect of P110 δ inhibition on angiogenesis was investigated. HuVECs were treated with 0, 1.0, or 10 μM of compound I for 8 h, and tube formation by endothelial cells was evaluated (FIG. 35A). HuVEC cells were plated on Matrigel-coated surfaces and allowed to form tubules for 8 h, in the presence or absence of Compound I. Endothelial cell tube formation was measured by microscopic analysis, FIG. 35B. *$P<0.005$.

Figure 35C:
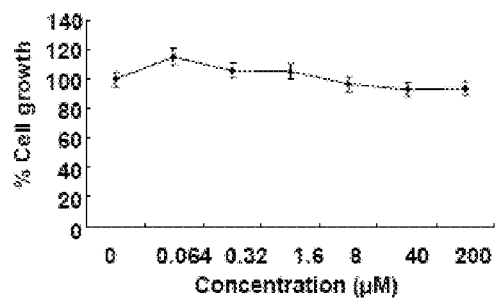
FIG. 35 C shows a graph charting % cell growth of HuVECs as a function of the increasing culture concentration of compound I.

HuVECs were cultured with Compound I (0-20 μM) 48 h, and viability was assessed by MTT assay, FIG. 35C. Data shown are mean±SE of triplicate wells from a representative experiment. Thus, compound I inhibited capillary-like tube formation in a dose-dependent fashion ($p<0.05$) (FIG. 35B), without associated cytotoxicity (FIG. 35C).

Figure 35D:
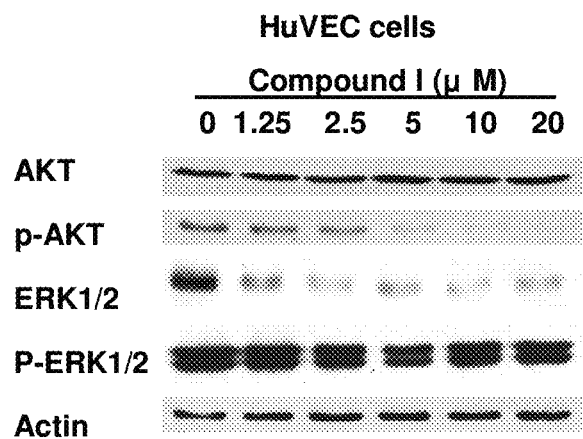

Phosphorylation and expression of AKT and ERK1/2 was markedly down regulated in HuVEC cells by compound I treatment. HuVECs were cultured with compound I (0-200 μM) for 8 h, and cell lysates were analyzed by immunoblotting using the indicated antibodies, FIG. 35D. Actin was used as a loading control.

These findings suggest that compound I can inhibit angiogenesis, associated with down regulation of AKT and ERK activity.

EXAMPLE 34

Compound II Inhibits MM Cell Growth In vivo

This example demonstrates the ability of compound II to inhibit human MM cell growth in vivo.

The in vivo efficacy of P110δ inhibitor was evaluated in a xenograft model in which SCID mice are injected subcutaneously with human MM cells.

Mice injected with $5\times10^6$ LB cells were treated orally twice a day with control vehicle (●), and compound II 10 mg/kg (□) or 30 mg/kg (○). Mean tumor volume was calculated as in Materials and Methods, FIG. 36A. Error bars represent SD (±).

Figure 36A:
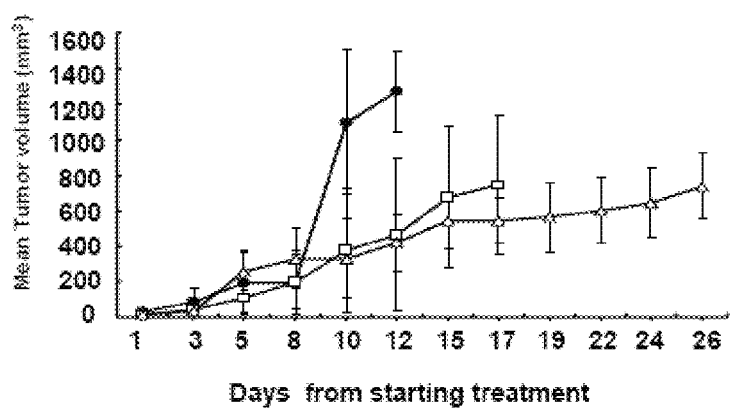
FIG. 36A charts the tumor volume in SCID mice with human MM xenografts treated with 0, 10 mg/kg or 30 mg/kg of compound II as a function of time, showing strong in vivo activity on the human xenograft tumor FIG. 36 B shows a photograph comparing the tumor from human MM xenografts on a mouse treated with compound II for 12 days to a control mouse.
Figure 36B:
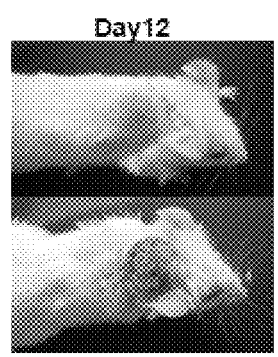
FIG. 36C shows the survival rate of SCID mice with human MM xenografts treated with 0, 10, and 30 mg/kg compound II over time.
FIG. 36D shows images from immuno-histochemistric analysis of tumors harvested from a mouse treated with compound II in comparison to the control; wherein CD31 and P-AKT positive cells are dark brown.
FIG. 36E shows immunoblots detecting PDK-1 and AKT levels from tumor tissues harvested from mice treated with compound II in comparison to a control.
FIG. 36F shows a chart of sIL6R levels measured in mice treated with 0, 10 mg/kg or 30 mg/kg of compound II over a period of 4 weeks of treatment as determined by ELISA.

Representative whole-body images from a mouse treated for 12 d with control vehicle (top panel) or Compound II (30 mg/kg) (bottom panel), FIG. 36B.

Tumors harvested from Compound II (30 mg/kg) treated mouse (right panel) and control mouse (left panel) were subjected to immuno-histochemistric analysis using CD31 and P-AKT Abs. CD31 and P-AKT positive cells are dark brown, FIG. 36D.

Figure 36C:
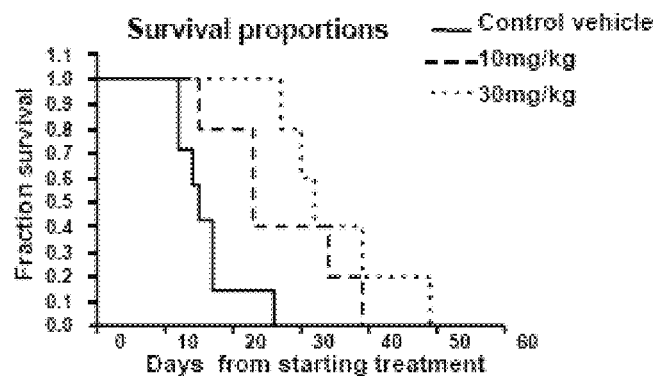

Mice were treated with Compound II 10 mg/kg (- -), 30 mg/kg (. . .) or Control vehicle (-). Survival was evaluated from the first day of treatment until sacrifice using Kaplan-Meier curves, FIG. 36C.

Tumor tissues were harvested from mice treated with control vehicle or Compound II (30 mg/kg). Protein levels of phosphorylated of PDK-1 and AKT (Ser473) were determined by western blotting of cell lysates, FIG. 36E. Actin was used as a loading control.

Growth of INA-6 cells engrafted in human bone chips in SCID mice was monitored by serial serum measurements of shuIL-6R. Mice were treated with Compound II 10 mg/kg (□), 30 mg/kg (Δ) or control vehicle (●), and shuIL-6R levels were determined weekly by ELISA, FIG. 36F. Error bars indicate SD (±).

Figure 36D:
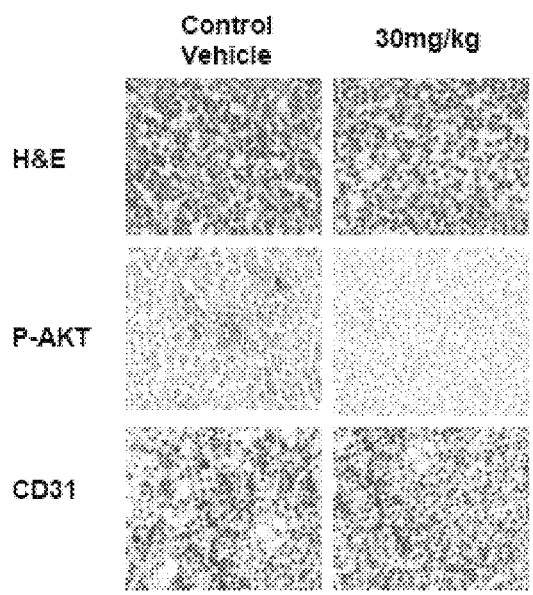
Figure 36E:
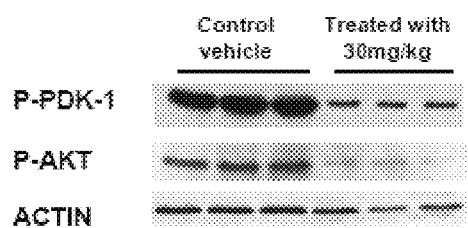

Compound II (p110 δ inhibitor) significantly reduced MM tumor growth in the treatment group (n=7) compared with control mice (n=7). Comparison of tumor volumes showed statistically significant differences between control versus treatment groups (vs 10 mg/kg, $P<0.05$; vs 30 mg/kg, $P<0.01$) (FIG. 36A). Marked decrease in tumor growth in treated versus in control mice was observed at day 12. (FIG. 36B) Kaplan-Meier curves and log-rank analysis showed a mean Overall Survival (OS) of 15 days (95% confidence interval, 12-17 days) in control mice versus 23 days (95% CI, 15-34 days) and 32 days (95% CI, 27-49 days) in the 10 mg/kg and 30 mg/kg compound II treated groups, respectively. Statistically significant prolongation in mean OS compared with control mice was also observed in treatment groups (vs 10 mg/kg, $P=0.086$; vs 30 mg/kg, $P=0.056$) (FIG. 36C) Importantly, treatment with either the vehicle alone or compound II did not affect body weight. In addition, immunohistochemical (FIG. 36D) and immunoblot (FIG. 36E) analysis confirmed that compound II treatment (30 mg/kg) significantly inhibited p-Akt and p-PDK-1, as well as significantly decreased CD31 positive cells and microvessel density ($p<0.01$) (FIG. 36D). This suggests that compound II can inhibit angiogenesis in vivo via suppression of the Akt pathway.

Figure 36F:
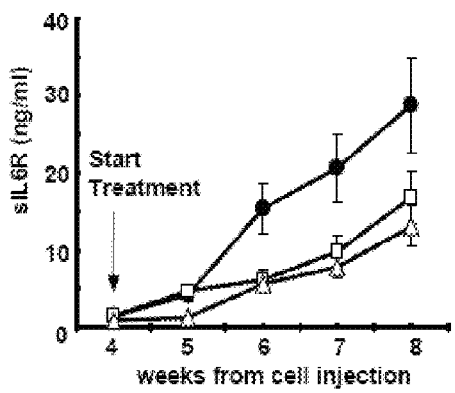

In order to examine the activity of compound II on MM cell growth in the context of the human BM microenvironment in vivo, a SCID-hu model was used in which IL-6 dependent INA-6 cells are directly injected into a human bone chip implanted subcutaneously in SCID-mice. This model recapitulates the human BM microenvironment with human IL-6/BMSC-dependent growth of INA-6 human MM cells. These SCID-hu mice were treated with compound II or vehicle alone daily for 4 weeks, and serum shuIL-6R monitored as a marker tumor burden. As shown in FIG. 36F, compound II treatment significantly inhibited tumor growth compared with vehicle control. Significant tumor growth inhibition in this model was observed, evidenced by decreased serum shuIL-6R levels released by INA-6 cells, confirming that p110δ inhibition blocks the MM growth promoting activity of the BM microenvironment in vivo. Taken together, these data demonstrate that inhibition of p110δ by compound II significantly inhibits MM growth in vivo and prolongs survival.

EXAMPLE 35

Compound I in Combination with Bortezomib Exhibits Synergistic Cytotoxicity

This example demonstrates the effect of Compound I in combination with bortezomib to mediate synergistic MM cytotoxicity.

The effects of combining compound I with bortezomib in inducing synergistic MM cytotoxicity was investigated. LB and INA-6 mM cells were cultured with medium (■) and with compound I, 1.25 µM (▨), 2.5 µM (▨), or 5.0 µM (□), in the presence or absence of bortezomib (0-5 nM). Cytotoxicity was assessed by MTT assay; data represent the mean±SD of quadruplicate-cultures, FIG. 37A.

INA-6 cells were treated with Compound I (5 µM) and/or bortezomib (5 nM) for 6 h. Phosphorylation of AKT was determined by western blotting of cell lysates using phospho-AKT (ser473) antibody, FIG. 37B. Actin served as a loading control.

Figure 37A:
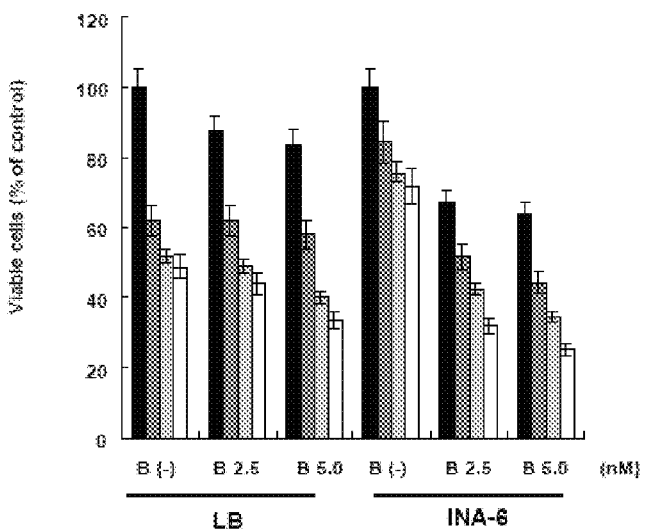
FIG. 37A show the % of viable LB or INA-6 mM cells after treatment with compound I with varying amounts of bortezomib (B); Legend: medium (■), compound I 1.25 μM (▨), 2.5 μM (▨), or 5.0 μM (□).
Figure 37B:
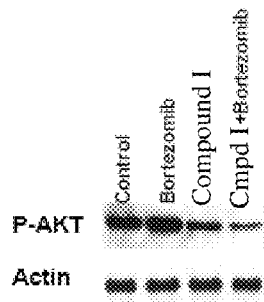
FIG. 37B shows immunoblots comparing levels of phosphorylation of AKT in INA-6 cells treated for 6 hours with compound I and/or bortezomib.

Compound I enhances cytotoxicity of bortezomib. Increasing concentrations of compound I (1.5-5.0 µM) added to bortezomib (2.5, 5.0 nM) triggered synergistic cytotoxicity in LB and INA-6 mM cells (FIG. 37A and Table 7). Importantly, induction of phospho-Akt by bortezomib treatment was inhibited in the presence of compound I (FIG. 37B).

TABLE 7

| | Combinatian index (CI) | | | |
|---|---|---|---|---|
| | Bortezoinib (nM) | Compound I (µM) | Fa | CI |
| LB | 2.5 | 1.25 | 0.39 | 0.57 |
| | 2.5 | 2.5 | 0.52 | 0.58 |
| | 2.5 | 5 | 0.57 | 0.67 |
| | 5 | 1.25 | 0.42 | 0.88 |
| | 5 | 2.5 | 0.60 | 0.25 |
| | 5 | 5 | 0.67 | 0.22 |
| INA-6 | 2.5 | 1.25 | 0.49 | 0.31 |
| | 2.5 | 2.5 | 0.58 | 0.48 |
| | 2.5 | 5 | 0.69 | 0.54 |
| | 5 | 1.25 | 0.56 | 0.73 |
| | 5 | 2.5 | 0.66 | 0.42 |
| | 5 | 5 | 0.75 | 0.31 |

EXAMPLE 36

Compound I Effective in Follicular Lymphoma Cell Lines

Figure 38:
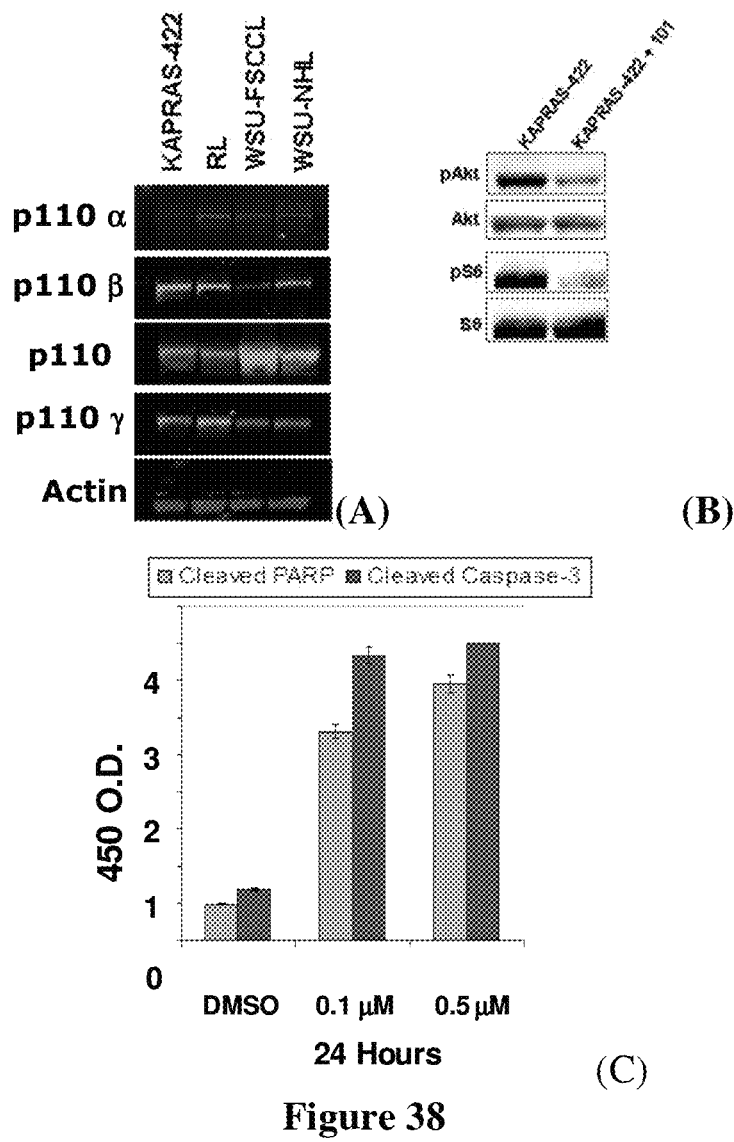
FIG. 38 shows (A) PI3K isoform expression in a panel of follicular lymphoma cell lines; (B) reduction in the expression of pAkt, Akt, pS6 and S6 after exposure to compound I; and (C) Increase in PARP and caspase-3 cleavage after exposure to compound I in a dose-dependent manner.

This example provides evidence that compound I blocks PI3K signaling and induces apoptosis in follicular lymphoma cells. P110δ is expressed in FL cell lines as shown in FIG. 38A. Certain cell lines show reduction in the production of pAkt, Akt, pS6 and S6 when the cell is exposed to compound I, FIG. 38B. Cleavage of PARP and Caspase-3 is observed after exposure to compound I in a dose dependent fashion after 24 hours at 0.1 µM and 0.5 µM, FIG. 38C.

EXAMPLE 37

Compound I Effective in Primary MCL Cells

Figure 39:
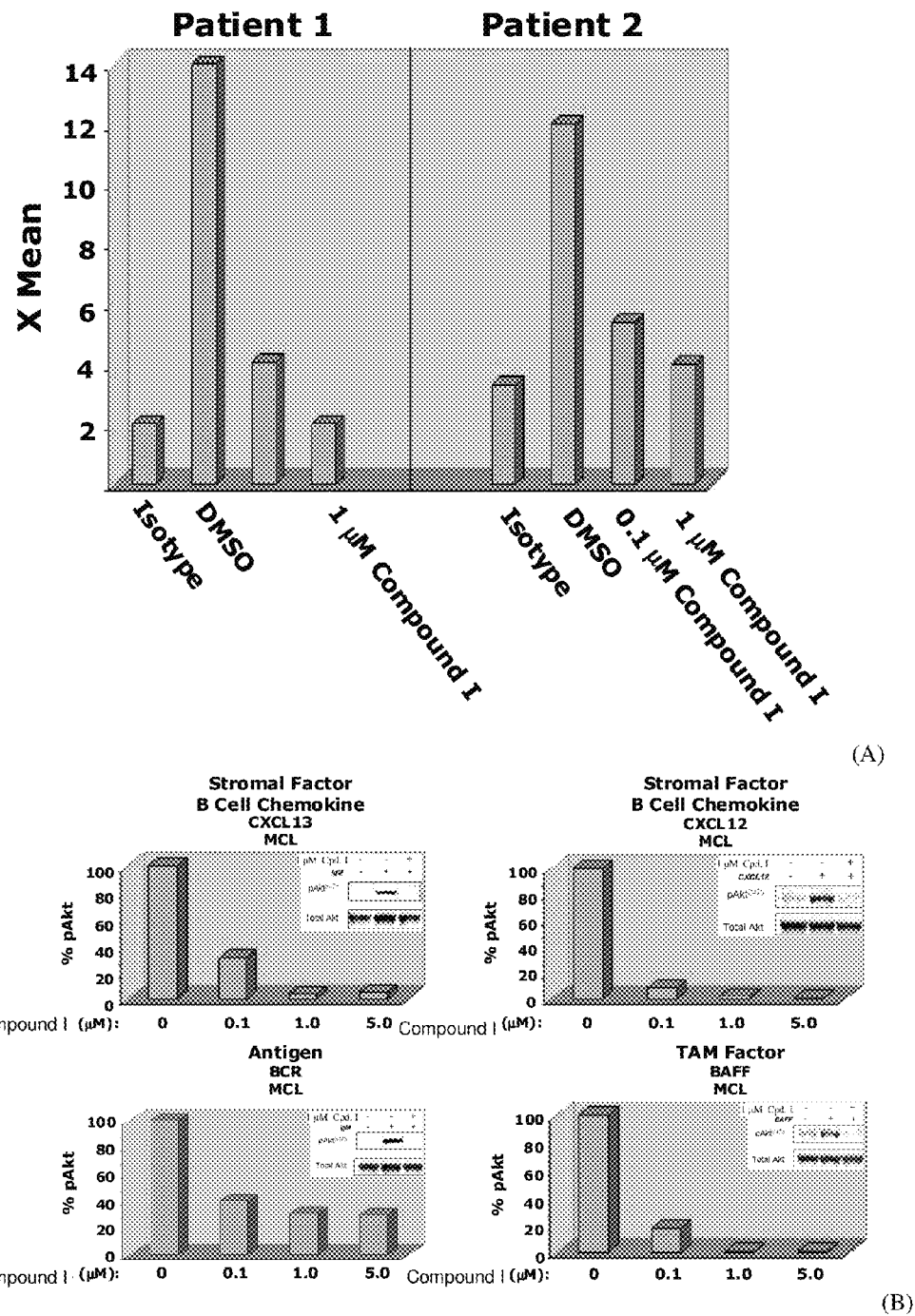
FIG. 39 shows (A) amounts of constitutive PI3K signaling in primary MCL cells in various amounts of compound I; (B) reduction in pAkt production in MCL cell lines containing a survival factor and varying amounts of compound I.

This example demonstrates that compound I is effective against MCL. Compound I was found to block constitutive PI3K signaling in primary MCL cells of two patients in a dose dependent manner when exposed to 0.1 µM or 1 µM of compound I, FIG. 39A. Compound I is also observed to inhibit survival factor and chemokine signaling in MCL cell lines. FIG. 39B shows a significant reduction of pAkt in MCL lines exposed to different survival factors in the presence of compound I.

EXAMPLE 38

Effect of Compound in Combination with Ofatumumab in CLL

This example summarizes the Phase 1-2 study of repeated cycles (28 days/cycle) of compound I in combination with ofatumumab for the treatment of patients who had previously been treated for CLL.

Compound I (150 mg 2 times per day [BID]) was co-administered continuously with 12 infusions of ofatumumab given over 24 weeks. Ofatumumab was administered with an initial dose of 300 mg on either Day 1 or Day 2 (relative to the first dose of compound I). One week later, ofatumumab was administered at 1,000 mg every week for 7 doses, then at 1,000 mg every 4 weeks for 4 doses. After completion of the ofatumumab treatment, each subject continued to receive compound I as a single agent at a dose of 150 mg BID as long as the subject was benefitting.

From the entire cohort of 21 patients, demographic and preliminary efficacy data from 11 patients were available. The median [range] age was 63 [54-76] years. The majority (9/11; 82%) of patients had bulky adenopathy (≥1 lymph node measuring ≥5 cm in longest dimension). The median [range] number of prior therapies was 3 [1-6], including prior exposure to alkylating agents (10/11; 90%), rituximab (9/11; 82%), purine analogs (8/11; 72%), alemtuzumab (3/11; 28%) and/or ofatumumab (2/11; 18%). At the data cutoff, the median [range] treatment duration was 5 [0-7] cycles. Almost all subjects (9/11; 82%) experienced marked and rapid reductions in lymphadenopathy within the first 2 cycles. Among the 11 patients, 10 were evaluable for response assessment at the end of Cycle 2 or later. Eight patients (80%) met criteria for a response as judged by the investigator based on the criteria published in Hallek M, et al. (Guidelines for the diagnosis and treatment of chronic lymphocytic leukemia: a report from the International Workshop on Chronic Lymphocytic Leukemia updating the National Cancer Institute-Working Group 1996 guidelines. Blood. 2008 Jun. 15; 111(12):5446-56). One patient had reduced lymphadenopathy meeting criteria for stable disease, and one patient had disease progression. The transient increase in the peripheral lymphocyte counts that was expected with single-agent PI3Kδ inhibition was reduced in magnitude and duration. The reduction of the transient lymphocytosis was induced by the combination of compound I and oftatumumab.

Preliminary safety data show that the combination treatment had a favorable safety profile and lacked myelosuppression. In addition, pharmacodynamic data revealed that elevated baseline levels of CLL-associated chemokines and cytokines (CCL3, CCL4, CXCL13, and TNFα) were reduced after 28 days of treatment. The results suggest that the combination of compound I with ofatumumab provides a well-tolerated, non-cytotoxic treatment regimen in patients with previously treated CLL.

EXAMPLE 39

Effect of Compound in Combination with BCL-2 antagonists in CLL

This example shows the effect of compound I in combination with BCL-2 antagonists ABT-737 and ABT-263 on the stroma-exposed CLL cells.

CLL Cell Purification: Peripheral blood, bone marrow, and lymph node were obtained from consent patients fulfilling diagnostic and immunophenotypic criteria for CLL. Peripheral blood mononuclear cells (PBMCs) were isolated from blood and tissue samples using the Ficoll-Paque (GE Healthcare, Waukesha, Wis.) density gradient centrifugation. Samples were either analyzed fresh or viably frozen in 10% dimethyl sulfoxide (DMSO; Sigma-Aldrich, St. Louis, Mo.) in fetal bovine serum (BD Biosciences, San Diego, Calif.) and stored in liquid nitrogen and later thawed for analysis. Single cell suspensions were prepared for analysis on a fluorescence activated cell sorting (FACS) machine, and CD19+CLL cells generally accounted for >85% of analyzed cells.

Cell Lines: Murine CD154+ L cell line was maintained in RPMI 1640 medium supplemented with 10% FBS, 2.05 mM L-glutamine (HyClone, Logan, Utah), and penicillin-streptomycin (Cellgro, Manassas, Va.). The human stromal cell line StromaNKTert was purchased from the Riken cell bank (Tsukuba, Japan) and maintained in alpha-MEM supplemented with 1 μg/mL hydrocortisone, 10% FBS, 10% human serum (Invitrogen, Grand Island, N.Y.), 2.05-mM L-glutamine, and penicillin-streptomycin. Nurse-like cells (NLCs) were established by suspending PBMC from patients with CLL in complete RPMI 1640 medium with 10% FBS and penicillin-streptomycin-glutamine to a concentration of $10^7$ cells/mL (2 mL total). Cells were grown for 14 days in 24-well plates (Corning Life Sciences).

CLL Cell and Stromal Cell Co-Cultures: CLL cells were cultured under standardized conditions on stromal cell lines or primary NLC. Briefly, stromal cells were seeded one day prior to each experiment onto 24-well plates (Corning Life Sciences) at a concentration of $3 \times 10^5$ cells/mL/well and incubated at 37° C. in 5% $CO_2$. Stromal cell confluence was confirmed by phase contrast microscopy, and CLL cells were then added onto the stromal cell layer at a concentration of $3 \times 10^6$ cells/mL. Cultures were then treated with compounds for the specified time periods. CLL cells were removed for analysis by gentle pipetting with media, and were then washed in PBS prior to analysis. A 24-hour co-culture time point was used unless otherwise indicated.

Cell Viability Testing and Reagents: CLL cell viability was determined by analysis of Annexin V-FITC (BD Biosciences, San Diego, Calif.) and Propidium Iodine (PI) (Sigma) by FACS. ABT-737, ABT-263, and compound I were stored in DMSO at −20° C. until use.

BH3 Profiling: CLL patient peripheral blood, bone marrow, and lymph node samples were analyzed by either the plate-based fluorimetry or FACS method. Briefly, PBMCs from CLL patients were made into single cell suspensions and gently permeabilized using digitonin (0.002%). For the fluorimtery-based method, 100 μM JC-1 (Invitrogen) was added at this time and cells were then loaded onto a 384-well plate, with individual wells containing individual BH3-only peptides. The JC1-BH3 assays were then conducted in triplicate on a Tecan Safire 2 with Ex 545+/−20 nM and Em 590+/−20 nm with a three-hour time course. For the FACS-based method, single cell suspensions from CLL patient PBMCs were stained using human Fc Block (BD Pharmingen) followed by anti-CD19-V450 (BD Pharmingen) and anti-CXCR4-APC (BD Pharmingen). Cells were washed in PBS and then added into individual FACS tubes, each of which contained an individual BH3-only peptide. Samples were incubated at room temperature for 30 minutes, 100 μM JC-1 was added to each tube, and the samples were incubated for an additional 30 minutes. FACS measurements were conducted on a BD FACS Canto II with lasers at 407, 488, and 633 nm JC-1 was measured from the 488-nm laser using a 530/30-nm filter (FITC) and a 585/42-nm filter (PE), and the degree of mitochondrial depolarization was calculated using the surrogate of the change in the median of PE signal. The mitochondrial depolarization reported in response to each BH3 peptide is normalized relative to the median percentage change in PE fluorescence of the JC-1 dye with a negative control, dimethyl sulfoxide (DMSO) (0%) and a positive control, the mitochondrial uncoupling agent carbonyl cyanide 4-(trifluoromethoxy)-phenylhydrazone (FCCP) (100%).

Calcein-Based Adhesion Assay: a confluent monolayer of CD154+L or StromaNKTert cells was generated by plating $1 \times 10^4$ cells/well in 96-well plates for 24 hours. Single cell suspensions of CLL cells at $0.5 \times 10^6$ cells/ml were then labeled with 1 μg/mL Calcein-AM (Invitrogen) for 1 hour. Cells were then spun down and treated with compound or vehicle for 1 to 24 hours. Non-adherent cells were washed off by aspiration. CLL cell adhesion was quantified by fluorimetry (Ex/Em=485/520 nm), and visualized directly using the Nikon TE2000 inverted live-cell imaging system.

Data Analysis and Statistics: Results are shown with standard error of mean and number of replicates as described in each figure. Student's paired or unpaired t-tests, Mann-Whitney U test, or linear regression analyses were used for statistical comparisons. Analyses were performed with GraphPad Prism 5 software for PC (GraphPad Software, San Diego, Calif.). Flow cytometry data were analyzed using FACS Diva version 6.1.1 (BD Pharmingen). Clinical response was assessed using 2008 IW-CLL criteria with responders defined as patients achieving a complete or partial response as best response, and non-responders as patients with stable disease, refractory disease, or progressive disease within 6 months of finishing first therapy. A two-tailed p-value<0.05 was considered statistically significant unless otherwise indicated.

Currently, many patients receiving the first-line traditional CLL therapy often relapse and develop resistant to their treatment. Because CLL cells exposed to various stroma are resistant to treatment with both cytotoxic chemotherapy (Kurtova A V et al. Diverse marrow stromal cells protect CLL cells from spontaneous and drug-induced apoptosis: development of a reliable and reproducible system to assess stromal cell adhesion-mediated drug resistance. *Blood.* 2009; 114(20):4441-4450) and BH3-mimetics such as ABT-737 or ABT-263 (Vogler M et al. Concurrent up-regulation of BCL-XL and BCL2A1 induces approximately 1000-fold resistance to ABT-737 in chronic lymphocytic leukemia. *Blood.* 2009; 113(18):4403-4413), CLL cells in the stromal microenvironment may receive proliferative or anti-apoptotic signals from stroma and become protected from cell apoptosis. Thus, agents that antagonize the interactions may reduce the stroma-mediated resistance in CLL.

The compound of formula I may modulate the stromal microenvironment. In clinical studies, most patients treated with compound I and other agents targeting the BCR pathway exhibited a rapid and transient lymphocytosis. Without being bound to any theory, compound I may modulate the stromal microenvironment by inhibiting CLL cell chemotaxis towards CXCL12/13, reducing CLL cell migration beneath stromal cells, down-regulating chemokine secretion, or inhibiting phosphorylation of other downstream targets such as AKT and ERK. To characterize whether compound I modulate the CLL-stroma interaction by increasing mitochondrial apoptosis or priming, the BH3 profiling was used to measure the permeabilization of mitochondria induced by peptides derived from the pro-death BH3 domains of pro-death BCL-2 family proteins.

Figure 41A:
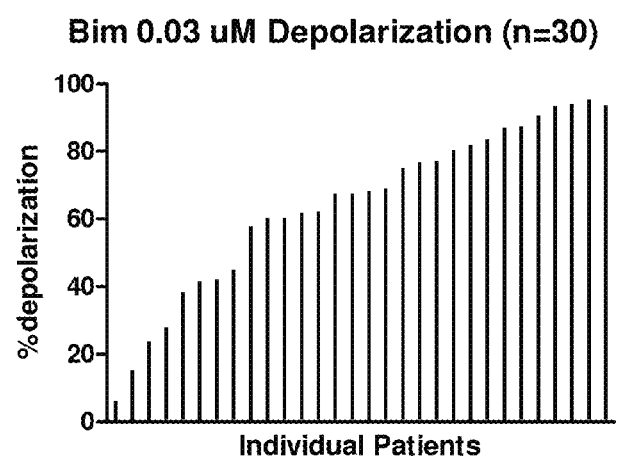
FIG. 41A shows a graph quantifying mitochondrial depolarization induced by the BIM BH3 peptide at 0.03 μM final concentration in peripheral blood CLL cells that were BH3 profiled by FACS (n=30).
Figure 41B:
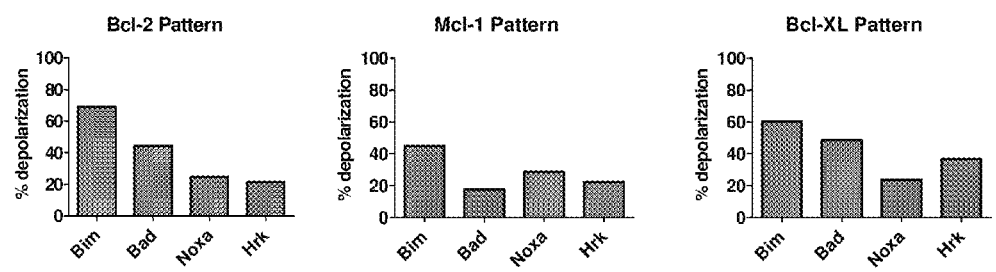
FIG. 41B shows BH3 profiles from three individual patients showing pattern of predominant dependence on BCL2, Mcl-1, and Bcl-XL.
Figure 41C:
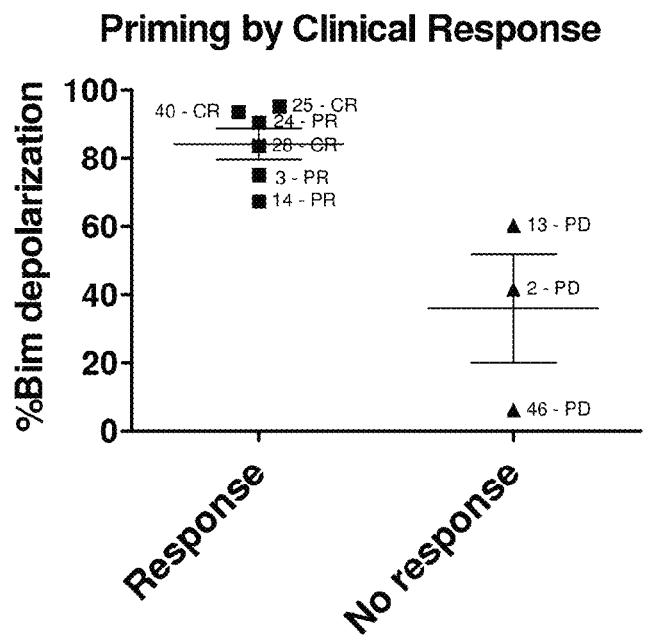
FIG. 41C is a graph showing BIM depolarization in treatment-naïve patients achieving a partial response (PR) or complete response (CR) by 2008 IW-CLL criteria compared to patients with progressive disease (PD) during or within six months of completing frontline CLL therapy (p=0.024).
Figure 41D:
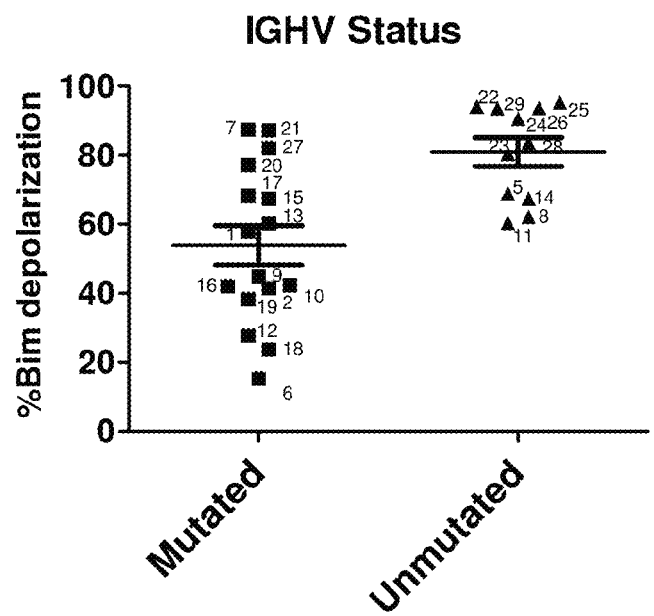
FIG. 41D is a graph showing BIM depolarization in patients with unmutated IGHV status (n=7) compared to patients with mutated IGHV status (n=18) (p=0.0026).
Figure 41E:
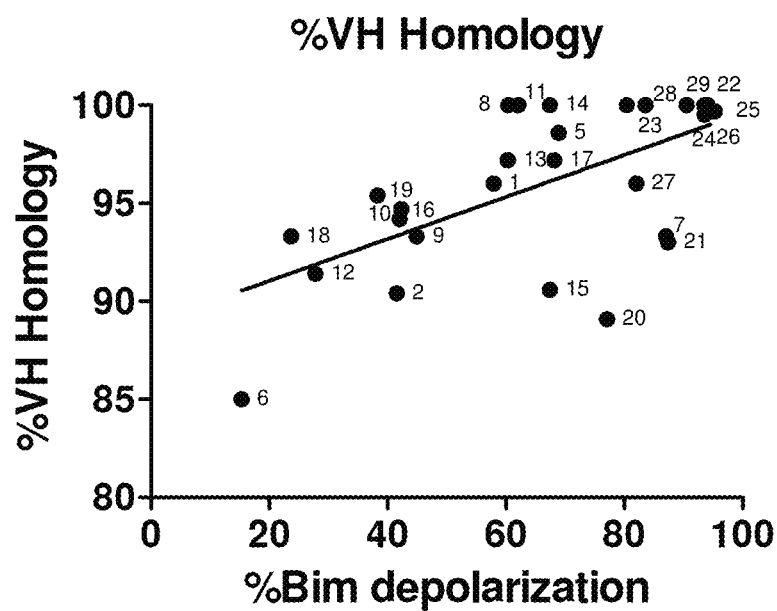
FIG. 41E is a graph showing the correlation between percentage of VH homology to germline with level of priming (p=0.0043).

First, CLL cells from the peripheral blood of 30 patients were examined. Most patients had not been treated previously, and none had received therapy. At a final concentration of 0.03 µM in the BH3 profiling, BIM BH3 peptide induced a significant amount of depolarization in most patient samples, with 22/30 (73.3%) of samples having >50% depolarization by 1 hour. As shown in FIG. 41A, CLL cells were highly primed for apoptosis. Also, the results of BH3 profiling showed that most CLL patient samples showed relatively increased depolarization from BAD BH3 peptide, suggesting primary dependence on BCL-2 (n=23). As shown in FIG. 41B, some samples were observed to be more dependent on MCL-1 (n=5), or BCL-XL (n=2). As shown in FIG. 41C, pre-treatment samples from treatment-naïve patients achieving a partial response (PR) or complete response (CR) by 2008 IW-CLL criteria were observed to be more primed than samples from patients with progressive disease (PD) during or within 6 months of completing frontline CLL therapy (p=0.024). As shown in FIG. 41D, BH3 profiling shows that patients with unmutated IGHV status (n=7) were significantly more primed than patients with mutated IGHV status (n=18) (p=0.0026). As shown in FIG. 41E, percentage of VH homology to germline was observed to be positively correlated with level of priming (p=0.0043). Thus, it was observed that CLL cells were highly primed for apoptosis, that CLL cells were usually BCL-2 dependent, and that increased priming was associated with improved clinical response and unmutated IGHV.

Figure 42A:
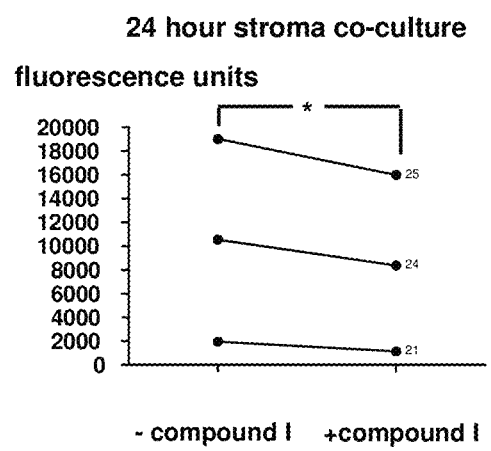
FIGS. 42A and 42B show graphs depicting CLL cell adherence quantified by whole well fluorimetry at 24 hours and 1 hour, respectively (one-tailed p=0.045 and 0.032, respectively).
Figure 42B:
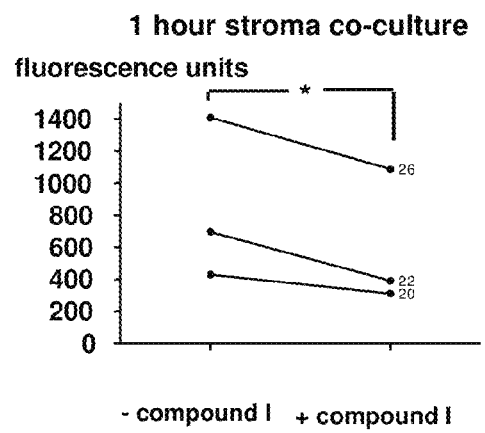
Figure 42C:
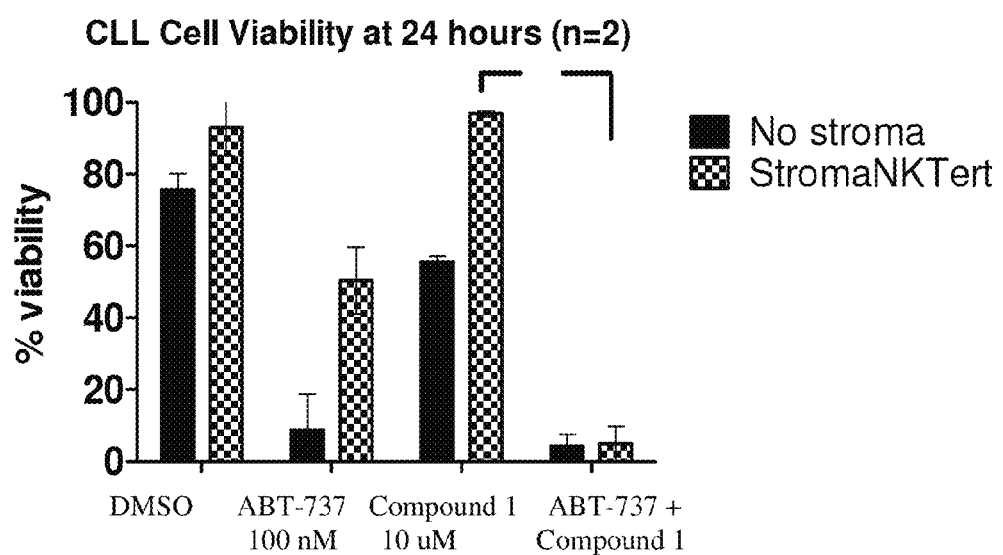
FIG. 42C shows a graph depicting CLL cell viability as assessed by Annexin V/PI of PB-derived CLL cells co-cultured in the presence or absence of StromaNK-Tert for 24 hours, with drug treatments as depicted in the graph.
Figure 42D:
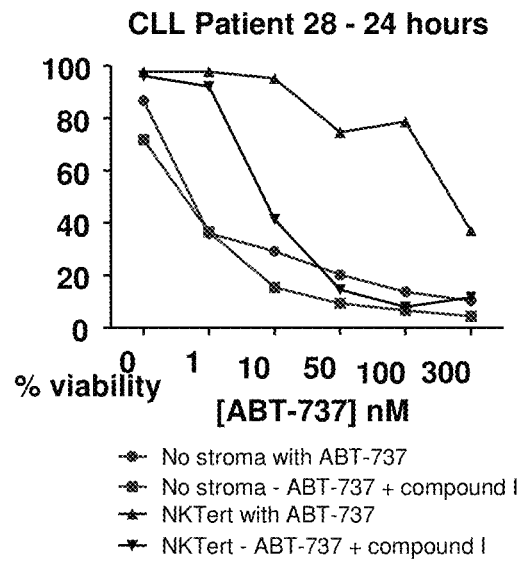
FIG. 42D shows dose response curves for CLL cells cultured in the presence of ABT-737 for 24 hours with or without StromaNKTert and with or without compound I.

Next, the effects of compound I on the adhesion, viability, and priming of the stroma-exposed CLL cells in vitro were evaluated. FIGS. 42A-E generally show that compound I was observed to release CLL cells sequestered in stroma to overcome stroma-mediated resistance. Peripheral blood-derived CLL cells were labeled with calcein-AM and co-cultured on stromaNKTert for 24 hours with or without compound I (10 µM), rinsed by gentle pipetting, and visualized by wide-field microscopy. As shown in FIG. 42A, CLL cells co-cultured with stromaNKTert and treated with compound I exhibited less adherent at 24 hours. Also, FIG. 42B showed that the reduced adherence of CLL cells was detectable even after only one hour treatment of compound I, which was before CLL cell death would occur. Moreover, FIG. 42C showed that the de-adherence of CLL cells from stroma in response to compound I resulted in enhanced killing of CLL cells. In particular, mean percent viability for two patients was depicted along with SEM in FIG. 42C, and both of these patients demonstrated profound stroma-mediated resistance to either ABT-737 at 100 nM or compound I at 10 µM alone. This resistance was observed to be overcome by the combination of the two compounds.

Figure 42E:
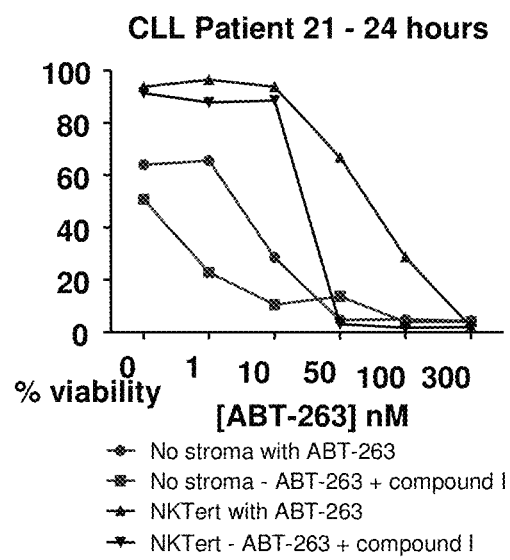
FIG. 42E shows dose response curves for CLL cells cultured in the presence of ABT-263 with or without StromaNKTert and with or without compound I.

To avoid examine the direct killing of CLL cells by compound I, two CLL patient samples that were resistant to both ABT-737 and compound I were treated in the presence of stroma. In both samples, compound I restored sensitivity of CLL cells to ABT-737 in the presence of stroma. In addition, stroma-exposed CLL cells treated with compound I (10 µM) in combination of various doses of ABT-737 and its oral analogue ABT-263 showed that stroma-exposed CLL cells exhibited a dose-dependent increase in killing with either BH3 mimetic. In particular, with reference to FIG. 42D, resistance to ABT-737 was observed in the presence of StromaNKTert, but may be overcome with concentrations of ABT-737 as low as 10 nM. With reference to FIG. 42E, ABT-263 had a similar dose-response curve.

Figure 43A:
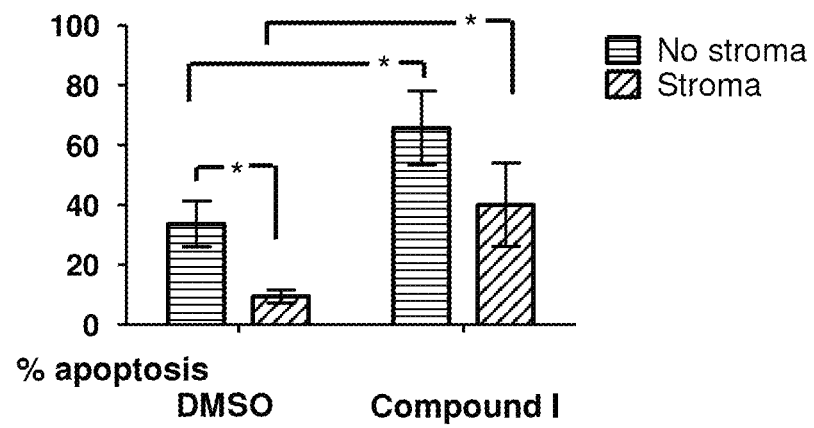
FIG. 43A shows aggregate CLL cell % apoptosis as measured by AnnexinV/PI for all four patient samples.

To determine whether PI3K inhibition increased the sensitivity of stroma-exposed CLL cells by increasing priming, PB-derived CLL cells cultured with or without StromaNKTert cells for 24 hours and were examined using Annexin-P1 and BH3 profiling. Untreated CLL cells generally exhibited apoptosis in ex vivo culture over 24 hours (Collins R J et al. Spontaneous programmed death (apoptosis) of B-chronic lymphocytic leukaemia cells following their culture in vitro. *British journal of haematology.* 1989; 71(3):343-350). Stromal co-culture of four CLL patient samples led to protection from apoptosis in untreated cells. In particular, with reference to FIG. 43A, a two-way ANOVA analysis showed that stroma provided protection from apoptosis in the absence of compound I. In the absence of stroma, compound I was observed to induce more apoptosis than the control. In the presence of stroma, compound I was observed to induce significantly more apoptosis than the control. Thus, no significant difference was observed between killing by compound I in the presence or absence of stroma.

Figure 43B:
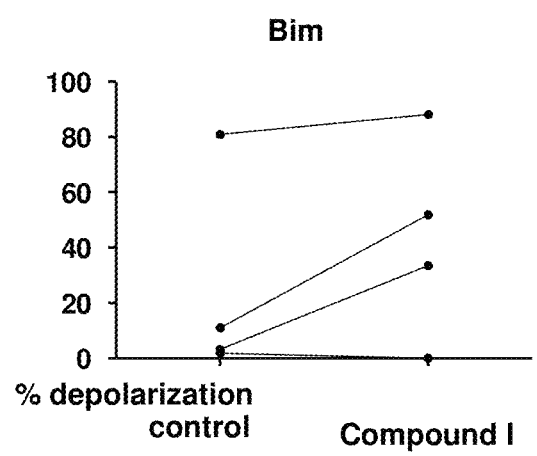
FIG. 43B shows a graph depicting mitochondrial depolarization in stroma-exposed CLL cells treated with compound I when compared to controls (one-tailed p=0.0749).
Figure 43C:
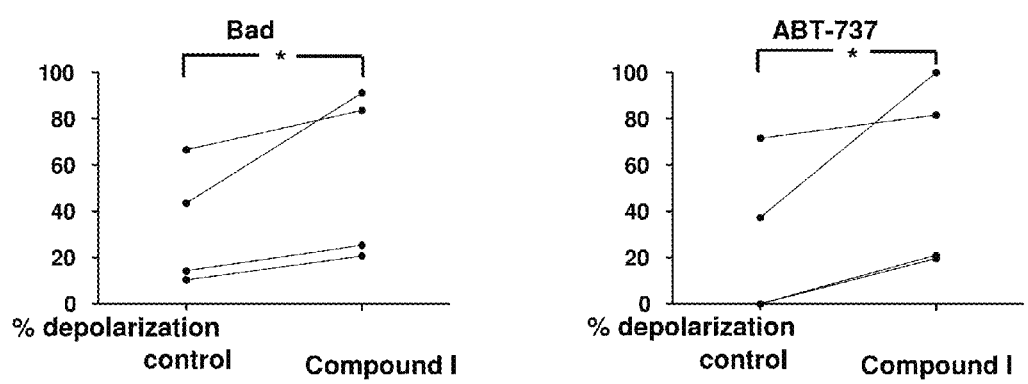
FIG. 43C shows a graph depicting mitochondrial depolarization in stroma-exposed CLL cells treated with BAD BH3 peptide and ABT-737 with compound I when compared to controls (one-tailed p=0.0462 and 0.0468, respectively).

However, the resistance or protection from apoptosis was reversed by compound I. More than 40% of apoptosis were detected in stroma-exposed CLL cells treated with compound I (10 µM) compared to less than 10% of apoptosis in untreated stroma-exposed CLL cells. Also, as shown in FIG. 43B, the BH3 profiling showed that stroma-exposed CLL cells treated with compound I exhibited an increased mitochondrial priming at 24 hours compared to untreated cells (p=0.075). As shown in FIG. 43C, both BAD BH3 peptide and ABT-737 used as a peptide induced significantly more mitochondrial depolarization in CLL cells treated with compound I (p=0.046 and p=0.047, respectively). This suggests that the treatment with compound I results in de-adherence of CLL from stroma, accompanied by increased mitochondrial priming and increased sensitivity to BCL-2 antagonism.

Overall, this example suggested that PI3K inhibition antagonized the protection of CLL cells by stroma, and that compound I was effective at reversing the effects of stroma on CLL cells: adhesion, decreased mitochondrial priming, and decreased sensitivity to therapies that inhibit BCL-2. Also, the efficicay of compound I may be associated with lymphocyte redistribution in patients. By releasing CLL cells from stroma, compound I likely allowed CLL cells to emerge from the anti-apoptotic stromal milieu, thereby increasing their mitochondrial priming and being susceptible to apoptosis. This example also suggested the combinations of PI3K inhibition with BCL-2 inhibition increase the responses to BCL-2 inhibition.

The invention claimed is:

1. A method to treat acute lymphocytic leukemia (ALL), acute myeloid leukemia (AML), chronic lymphocytic leukemia (CLL) or small lymphocytic lymphoma (SLL), comprising administering to a human in need of such treatment, an effective amount of a compound of formula I or formula II:

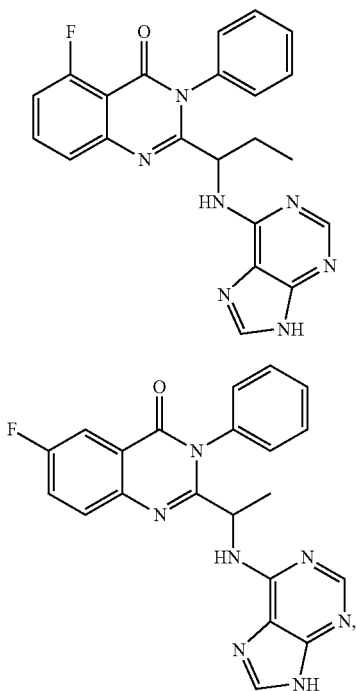

or a pharmaceutically acceptable salt thereof; and
optionally a pharmaceutically acceptable excipient;
and administering a monoclonal antibody,
wherein the human is refractory to chemotherapy treatment or in relapse after treatment with chemotherapy.

2. The method according to claim 1, wherein the compound of formula I or formula II or a pharmaceutically acceptable salt thereof is predominantly the S-enantiomer.

3. The method according to claim 1, wherein the compound of formula I is

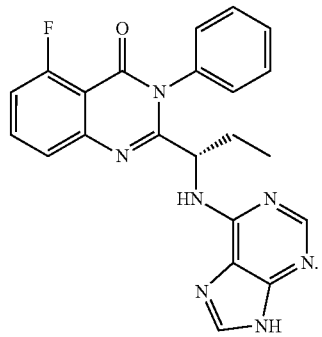

or a pharmaceutically acceptable salt thereof.

4. The method according to claim 1, wherein the compound of formula II is

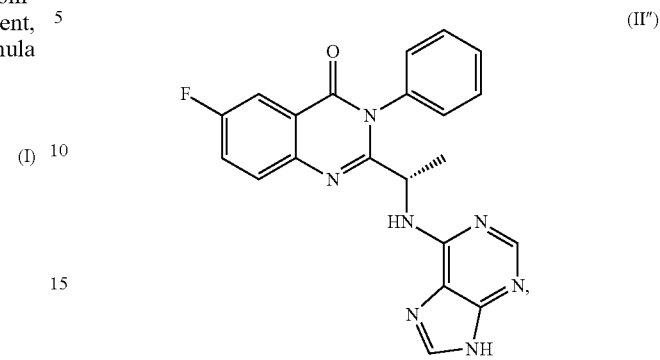

or a pharmaceutically acceptable salt thereof.

5. The method according to claim 1, wherein the acute lymphocytic leukemia (ALL) is B-cell ALL or T-cell ALL.

6. The method according to claim 1, wherein the monoclonal antibody is selected from the group consisting of rituximab and ofatumumab.

7. The method according to claim 1, wherein the compound of formula I or formula II or a pharmaceutically acceptable salt thereof is administered with a group of agents selected from the group consisting of a-j:
a) R-CHOP (rituximab-CHOP);
b) R-hyperCVAD (rituximab-hyperCVAD);
c) R-FCM (rituximab, fludarabine, cyclophosphamide, mitoxantrone);
d) bortezomib and rituximab;
e) temsirolimus and rituximab;
f) Iodine-131 tositumomab)(Bexxar®) and CHOP;
g) R-CVP (rituximab-CVP);
h) R-ICE (rituximab-ICE);
i) FCR (fludarabine, cyclophospharnide, rituximab); and
j) FR (fludarabine, rituximab).

8. The method according to claim 1, wherein the compound of formula I or formula I or a pharmaceutically acceptable salt thereof maintains an average blood plasma concentration in the human between 100 nM and 1100 nM over a period of at least 12 hours from compound administration.

9. The method according to claim 1, wherein 50 mg to 150 tug of the compound of formula I or formula II or pharmaceutically acceptable salt thereof is administered to the human twice a day.

10. The method according to claim 1, wherein the compound of formula I or formula II or a pharmaceutically acceptable salt thereof and the monoclonal antibody are formulated for separate, sequential, or simultaneous administration to the human.

11. The method according to claim 1, wherein the monoclonal antibody is an anti-CD20 monoclonal antibody.

12. The method of claim 1, wherein the method is to treat chronic lymphocytic leukemia (CLL).

13. The method of claim 1, wherein the monoclonal antibody is rituximab.

14. The method according to claim 13, wherein the chemotherapy treatment comprises treatment with an alkylating agent.

15. A method to treat chronic lymphocytic leukemia (CLL), comprising administering to a human in need of such treatment, an effective amount of a compound of formula I:

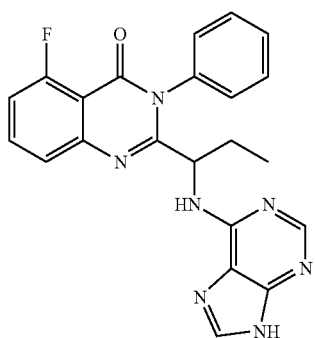

(I)

or a pharmaceutically acceptable salt thereof; and
optionally a pharmaceutically acceptable excipient;
and administering rituximab,
wherein the human is refractory to chemotherapy treatment or in relapse after treatment with chemotherapy.

16. The method according to claim 15, wherein the compound of formula I is

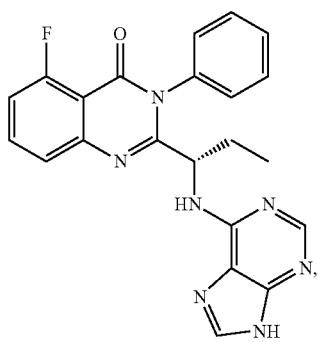

(I″)

or a pharmaceutically acceptable salt thereof.

* * * * *